US008343939B2

(12) United States Patent
Madsen et al.

(10) Patent No.: US 8,343,939 B2

(45) Date of Patent: Jan. 1, 2013

(54) METHODS OF MODULATING ANGIOGENESIS

(75) Inventors: Christian Rask Madsen, Newton, MA (US); George Liang King, Dover, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 116 days.

(21) Appl. No.: 12/510,201

(22) Filed: Jul. 27, 2009

(65) Prior Publication Data

US 2010/0135995 A1 Jun. 3, 2010

Related U.S. Application Data

(63) Continuation of application No. PCT/US2008/052350, filed on Jan. 29, 2008.

(60) Provisional application No. 60/898,085, filed on Jan. 29, 2007.

(51) Int. Cl.
*A61K 48/00* (2006.01)
*C07H 21/02* (2006.01)
*C07H 21/04* (2006.01)

(52) U.S. Cl. ......................... 514/44; 536/23.1; 536/24.5

(58) Field of Classification Search ........................ None
See application file for complete search history.

(56) References Cited

U.S. PATENT DOCUMENTS 5,783,405 A 7/1998 Mochly-Rosen et al.
6,506,559 B1 * 1/2003 Fire et al. ..................... 435/6.16
6,537,973 B1 3/2003 Bennett et al.
7,101,707 B2 * 9/2006 Castellon ...................... 435/375
2003/0134774 A1 * 7/2003 Steinberg et al. ................. 514/1
2008/0263689 A1 * 10/2008 Biden et al. ..................... 800/14

OTHER PUBLICATIONS

Pan et al. (Cancer Res, 2006, 66, 19, 2006, pp. 9379-9384).*
Gardner et al. (The Journal of Biological Chemistry, vol. 278, No. 17, pp. 15421-15428, 2003).*
Rask-Madsen, C., et al., Differential Regulation of VEGF Signaling PKC-α and PKC-ϵ in Endothelial Cells, AHA Journal, 2008, 919-924.
Yoon, Y., et al., Therapeutic myocardial angiogenesis with vascular endothelial growth factors, Molecular and Cellular Biochemistry, 2004, vol. 264, 63-74.
Kleiman, N., et al., Evolving Revascularization Approaches for Myocardial Ischemia, American Journal of Cardiology, 2003, vol. 92 (9B), 9N-17N.
Grines, C., et al., Angiogenic Gene Therapy (AGENT) Trial in Patients With Stable Angina Pectoris, Circulation, 2002, vol. 105, 1291-1297.
Grines, C., et al., A Randomized, Double-Blind, Placebo-Controlled Trial of Ad5FGF-4 Gene Therapy and its Effect on Myocardial Perfusion in Patients with Stable Angina, Journal of American College of Cardiology, 2003, vol. 42, No. 8, 1339-1347.
Rissanen, T., et al., Gene Transfer for Therapeutic Vascular Growth in Myocardial and Peripheral Ischemia, Advances in Genetics, 2004, vol. 52, 117-164.
Norrby, K., In vivo models of angiogenesis, Journal of Cellular and Molecular Medicine, 2006, vol. 10, No. 3, 588-612.
IPRP for PCT/US08/52350, 2008.

* cited by examiner

*Primary Examiner* — Amy Bowman

(74) *Attorney, Agent, or Firm* — Pierce Atwood LLP; Joseph M. Maraia; Kevin M. Farrell

(57) ABSTRACT

The present inventors discovered that PKCϵ is necessary for VEGF signaling through PI3K/Akt-dependent pathways and is involved in MAPK-dependent pathways, thus regulating eNOS activity and DNA synthesis, respectively. Thus differential manipulation of PKCϵ activity can be used to modify VEGF effects in conditions in which modulation of angiogenesis is desirable (e.g., for treatment of diabetic proliferative retinopathy or to enhance angiogenesis for treatment of peripheral and myocardial ischemia).

3 Claims, 19 Drawing Sheets

| | | | | | | |
|---|---|---|---|---|---|---|
| PMA | − | + | − | + | − | + |
| Insulin | − | − | + | + | − | − |
| VEGF | − | − | − | − | + | + |

| | | | | | | |
|---|---|---|---|---|---|---|
| PMA | − | + | − | + | − | + |
| Insulin | − | − | + | + | − | − |
| VEGF | − | − | − | − | + | + |

SEQUENCE LISTING

```
<160> NUMBER OF SEQ ID NOS: 29

<210> SEQ ID NO 1
<211> LENGTH: 5537
<212> TYPE: DNA
<213> ORGANISM: Homo sapiens

<400> SEQUENCE: 1

caacccggcg aggaaataca tgcactggct gagaatcgcc cgcgccaggg cgcaacgcca      60

caaggtgtag ggagtgtgcg gggtggggcg aaaggggacc caagagtccc tgtggctcgg     120

agtgccgggc cgtcggttct tcattcctgc cctcggggca gacggagtga ccccggcccc     180

cactccccgc cccgaccatg gtagtgttca atggccttct taagatcaaa atctgcgagg     240
```

-continued

```
ccgtgagctt gaagcccaca gcctggtcgc tgcgccatgc ggtgggaccc cggccgcaga    300
ctttccttct cgacccctac attgccctca atgtggacga ctcgcgcatc ggccaaacgg    360
ccaccaagca gaagaccaac agcccggcct ggcacgacga gttcgtcacc gatgtgtgca    420
acggacgcaa gatcgagctg gctgtctttc acgatgcccc cataggctac gacgacttcg    480
tggccaactg caccatccag tttgaggagc tgctgcagaa cgggagccgc cacttcgagg    540
actggattga tctggagcca gaaggaagag tgtatgtgat catcgatctc tcagggtcgt    600
cgggtgaagc ccctaaagac aatgaagagc gtgtgttcag ggaacgcatg cggccgagga    660
agcggcaggg ggccgtcagg cgcagggtcc atcaggtcaa cggccacaag ttcatggcca    720
cctatcttcg gcagcccacc tactgctccc attgcagaga cttcatctgg ggtgtcatag    780
gaaagcaggg ataccagtgt caagtctgca cctgcgtggt ccacaagcgg tgccacgagc    840
tcataatcac aaagtgtgct gggttaaaga agcaggagac ccccgaccag gtgggctccc    900
agcggttcag cgtcaacatg ccccacaagt tcggtatcca caactacaag gtccctacct    960
tctgcgatca ctgtgggtcc ctgctctggg gactcttgcg gcagggtttg cagtgtaaag   1020
tctgcaaaat gaatgttcac cgtcgatgtg agaccaacgt ggctcccaac tgtggagtgg   1080
atgccagagg aatcgccaaa gtactggccg acctgggcgt taccccagac aaaatcacca   1140
acagcggcca gagaaggaaa aagctcattg ctggtgccga gtccccgcag cctgcttctg   1200
gaagctcacc atctgaggaa gatcgatcca agtcagcacc cacctcccct tgtgaccagg   1260
aaataaaaga acttgagaac aacattcgga aagccttgtc atttgacaac cgaggagagg   1320
agcaccgggc agcatcgtct cctgatggcc agctgatgag ccccggtgag aatggcgaag   1380
tccggcaagg ccaggccaag cgcctgggcc tggatgagtt caacttcatc aaggtgttgg   1440
gcaaaggcag ctttggcaag gtcatgttgg cagaactcaa gggcaaagat gaagtatatg   1500
ctgtgaaggt cttaaagaag gacgtcatcc ttcaggatga tgacgtggac tgcacaatga   1560
cagagaagag gattttggct ctggcacgga aacacccgta ccttacccaa ctctactgct   1620
gcttccagac caaggaccgc ctctttttcg tcatggaata tgtaaatggt ggagacctca   1680
tgtttcagat tcagcgctcc cgaaaattcg acgagcctcg ttcacggttc tatgctgcag   1740
aggtcacatc ggccctcatg ttcctccacc agcatggagt catctacagg gatttgaaac   1800
tggacaacat ccttctggat gcagaaggtc actgcaagct ggctgacttc gggatgtgca   1860
aggaagggat tctgaatggt gtgacgacca ccacgttctg tgggactcct gactacatag   1920
ctcctgagat cctgcaggag ttggagtatg gcccctccgt ggactggtgg gccctggggg   1980
tgctgatgta cgagatgatg gctggacagc ctccctttga ggccgacaat gaggacgacc   2040
tatttgagtc catcctccat gacgacgtgc tgtacccagt ctggctcagc aaggaggctg   2100
tcagcatctt gaaagctttc atgacgaaga atccccacaa gcgcctgggc tgtgtggcat   2160
cgcagaatgg cgaggacgcc atcaagcagc acccattctt caaagagatt gactgggtgc   2220
tcctggagca gaagaagatc aagccaccct tcaaaccacg cattaaaacc aaaagagacg   2280
tcaataattt tgaccaagac tttacccggg aagagccggt actcaccctt gtggacgaag   2340
caattgtaaa gcagatcaac caggaggaat tcaaaggttt ctcctacttt ggtgaagacc   2400
tgatgccctg agagcccact gcagttggac tttgccgatg ctgcaagaag ggtgcagag    2460
aagactcctg tgttggagac actcagcagg tcttgaacta cttctcctcc tcggagcccc   2520
agtcccatgt ccactgtcta tttattgcat tcccttgccc caggccacct cctcccccctc  2580
ccacctggtg accagaaggc gctctcggtt cttgtctcac cagtaatgca gactcattgg   2640
```

-continued

```
gtcagcaatt agctgtatac actgccgtgt ttggaccatt ggcaagcctg gttccactcc   2700
tcaggggctc ctggcagtga agcaacttca gttcttttac tgcaaagaac agaaaaaaga   2760
aagaaagcaa acaagaagac tccggctctg ctatcggaca cagatcctga tccctcttgc   2820
ttcttttccc tcctgcaccg cagcttgcca tccctgccct tctgtcctgg agaagagact   2880
ggtgcttctc cgcacacacg agggagggcg cccttgaggc atgccctctg agggagggag   2940
accagagatg cagggattgg ccagctgggt tggtttgctc tggaatggct aactcttgcc   3000
tgctttggtt ttagcttttc agcatgccaa agtcatgtaa gtttgtgtct tgtggaagaa   3060
atcctctttg tggaaaaaga aacagggttt tgaactctgt taacatttga aaaatatatt   3120
ttcaaattca ctttctaatt ggccaaaaga gatgagttcc agtctgaata caggtagata   3180
ttaaagggct aataaaaaat gagaaaccgg tcgtccaagg tggatgctgt caatgcccga   3240
gtgacacatg agagctgtat gaattgagag aaaaggcaac aagtagcatt cttcatcatt   3300
caagttctac ctggacacaa aggcgaggac cctggggttc caacaaagct cagctcccag   3360
attctctttc cagtttcatc ctaagttcct agcataaaca ctatttattt tctgcagcag   3420
tgtgttattt ttgcgcactt atacaaaatg gtagtactac tgtgttgtgg tttttaaaca   3480
ttaaacatgt aaagttatat acgaaatatc tgcttttgga ataagcagaa tgaggctaaa   3540
catgggttat acaaagggta tctggaaact gaagagcaac ttgttagaaa actgacaatg   3600
tcgcaagatg tactcagttt tgtttctgtg tgacatgcaa tggcaactca tgtggacact   3660
attgaaggga tgtgacatta cctcctgtag atatgctaac agtgttattc tttcatttcc   3720
aagggttctc tgtggctttg tgtatatgtt tcccagaggt catttgatta cctaatttac   3780
tgaactgatt tagcagggaa tggaatccat tccaactatt gcacgtggat ttcccagctg   3840
cccctaaata tatatacttg tgagtggcaa agtggcacta atgaagcttt tgccttttgt   3900
acatttgaga tttttgtata tagtgtttgc tgcaaggcct gtggaattaa ttcgttgcat   3960
atagaggtat caactgctgc atgttcaggc atattataaa actttagtct atgaaagaat   4020
aattataata atgtccaggt gcaatactct gtaagtctat tggttcaagt taccgagaga   4080
taggtgtgtt cctttatggg ggatgggggg gtgtgttggg gattctttgt attgtttatt   4140
tcattttggt ttattttaaa agatgtaaac atatattaag ctatattaaa tctcacatac   4200
agttcttctg tgctctatta taccctgata gagatggggg agagaaagga atgtttttga   4260
tggtggtttc aaagctcgga cagtaactat cttgagccca ttagagagtc tgtgtccata   4320
tttgcatctg gctggtcata gcctttgtta ctaatgatga cattcagttc tcttttgttt   4380
ttatttttta aaaactcagg tgtaattatt atctgttctt aagataattg caaatattaa   4440
atattatgat atatcaattc atgtgtttgg cataccagtg aatgatgaag aacatgagat   4500
taatttaatt tatcttcggt aacttgacat tctggagaga gactatcttc tggagttgag   4560
tacaagcaca gaaacatctt tacggtggca tcatctcatt ttttaggaag acatgataat   4620
actgcccatc atattcatgt gtaactactg ttctttcttc tgctttcttc accataataa   4680
actttggaca accaagcaag ctctaaccgc aatgccagat ggccttgtcc gagggcctag   4740
tgtttgcacg gcagtgggaa ctgggccttt cctacaggac aactggcaag tttgctggga   4800
agtcaaataa tacattccac ctggcagctg aaggcagcca gtcagtctgt cccagaaagg   4860
gcccttttca gcacccaaag ctgggctggc tgggatgcct ctggctggtg aagttctcac   4920
ataggctgat ttaaatccag caaaggtcta tagaaaaagg cttgcgtgtt cgttgagtaa   4980
tcattgtttc attttcattt ttacgagagt ttgaaaatag acacactgtt aacacttctg   5040
```

-continued

```
ccagtttttt ctgatctttc cagccccacc ccctttctct ttctctctct ctctcaaaga   5100

aaaaaaaaat gggagtgcaa aaaaaacaaa gccaaaaaat atatgaagga tagctgttct   5160

tctgtgttct ctcattatgg actttgtgaa gtagaaacat aatttttttt cctccaaagg   5220

tgaaaaaaca atgcattctt gctttaaaaa aaaaaaagaa ggctaaaaaa ttacctcttt   5280

ttaaattatg tgcaaaataa ttctggctaa ctgtaaaatg tattcaattt taggattttt   5340

tttttttgta ttgtgatgct ttatttgtac attttttttcc tttctggatg taattttaat   5400

ctcttgccat tcattagtgt tatttcattg taaacgttat tgtgccaaat gtactgtatt   5460

caaaaggatg tgaatgtgta ttgtttcaga acctaataaa tacaatgacg ttaagtctta   5520

aaaaaaaaaa aaaaaaa                                                 5537
```

<210> SEQ ID NO 2
<211> LENGTH: 737
<212> TYPE: PRT
<213> ORGANISM: Homo sapiens

<400> SEQUENCE: 2

```
Met Val Val Phe Asn Gly Leu Leu Lys Ile Lys Ile Cys Glu Ala Val
 1               5                  10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Arg Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220

Lys Gln Glu Thr Pro Asp Gln Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
        275                 280                 285
```

-continued

```
Ala Pro Asn Cys Gly Val Asp Ala Arg Gly Ile Ala Lys Val Leu Ala
    290                 295                 300

Asp Leu Gly Val Thr Pro Asp Lys Ile Thr Asn Ser Gly Gln Arg Arg
305                 310                 315                 320

Lys Lys Leu Ile Ala Gly Ala Glu Ser Pro Gln Pro Ala Ser Gly Ser
                325                 330                 335

Ser Pro Ser Glu Glu Asp Arg Ser Lys Ser Ala Pro Thr Ser Pro Cys
            340                 345                 350

Asp Gln Glu Ile Lys Glu Leu Glu Asn Asn Ile Arg Lys Ala Leu Ser
        355                 360                 365

Phe Asp Asn Arg Gly Glu Glu His Arg Ala Ala Ser Ser Pro Asp Gly
    370                 375                 380

Gln Leu Met Ser Pro Gly Glu Asn Gly Glu Val Arg Gln Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
        435                 440                 445

Asp Val Asp Cys Thr Met Thr Glu Lys Arg Ile Leu Ala Leu Ala Arg
    450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
        515                 520                 525

Ile Tyr Arg Asp Leu Lys Leu Asp Asn Ile Leu Leu Asp Ala Glu Gly
    530                 535                 540

His Cys Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
        595                 600                 605

Ala Asp Asn Glu Asp Asp Leu Phe Glu Ser Ile Leu His Asp Asp Val
    610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ser Gln
                645                 650                 655

Asn Gly Glu Asp Ala Ile Lys Gln His Pro Phe Phe Lys Glu Ile Asp
            660                 665                 670

Trp Val Leu Leu Glu Gln Lys Lys Ile Lys Pro Pro Phe Lys Pro Arg
        675                 680                 685

Ile Lys Thr Lys Arg Asp Val Asn Asn Phe Asp Gln Asp Phe Thr Arg
    690                 695                 700

Glu Glu Pro Val Leu Thr Leu Val Asp Glu Ala Ile Val Lys Gln Ile
705                 710                 715                 720
```

Asn Gln Glu Glu Phe Lys Gly Phe Ser Tyr Phe Gly Glu Asp Leu Met
725 730 735

Pro

<210> SEQ ID NO 3
<211> LENGTH: 2235
<212> TYPE: DNA
<213> ORGANISM: Mus musculus

<400> SEQUENCE: 3

```
gaattcacca tggtagtgtt caatggcctt cttaagatca aaatctgcga ggcggtgagc      60
ttgaagccca cagcctggtc gctgcgccat gcggtgggac cccggccaca gacgttcctt     120
ttggacccct acattgccct taacgtggac gactcgcgca tcggccaaac agccaccaag     180
caaaagacca acagcccggc ctggcacgat gagttcgtca ccgatgtgtg caatgggcgc     240
aagatcgagc tggctgtctt tcacgacgct cctatcggct acgacgactt cgtggccaac     300
tgcaccatcc agttcgagga gctgctgcag aatgggagcc gtcacttcga ggactggatt     360
gacctggagc cagaaggaaa agtgtacgtg atcatcgatc tctcgggatc atcgggtgaa     420
gcccctaaag acaatgaaga acgagtgttc agggagcgta tgcggccaag gaagcggcaa     480
ggggctgtca ggcgcagggt ccaccaggtc aatggccaca agttcatggc cacctacttg     540
cggcaaccca cctactgctc ccactgcaga gatttcatct ggggtgtcat aggaaaacag     600
ggatatcaat gtcaagtttg cacttgcgtt gtccacaagc gatgtcatga gctcattatt     660
acaaagtgcg ctgggctgaa gaaacaggaa accccctgacg aggtgggctc ccaacggttc     720
agcgtcaaca tgccccacaa gttcgggatc cacaactaca aggtccccac gttctgtgac     780
cactgtgggt ccctgctctg gggcctcttg cggcagggct tgcagtgtaa agtctgcaaa     840
atgaatgttc accggcgatg tgagaccaat gtggctccca actgtggggt agacgccaga     900
ggaattgcca aagtgctggc tgaccttggt gttactccag acaaaatcac caacagtggc     960
caaaggagga aaaagctcgc tgctggtgct gagtccccac agccggcttc tggaaactcc    1020
ccatctgaag acgaccgatc caagtcagcg cccacctccc cttgtgacca ggaactaaaa    1080
gaacttgaaa acaacattcg gaaggccttg tcatttgaca accgaggaga ggagcaccga    1140
gcgtcgtcgg ccaccgatgg ccagctggca agcccccggag agaacgggga agtccggcca    1200
ggccaggcca agcgcttggg gctggatgag ttcaacttca tcaaggtgtt gggcaaaggc    1260
agctttggca aggtcatgtt ggcggaactc aaaggcaaag atgaagtcta cgctgtgaag    1320
gtcttgaaga aggacgttat cctacaagac gatgatgtgg actgcacaat gacagagaag    1380
aggattttgg ctctggctcg gaaacaccct tatctaaccc aactctattg ctgcttccag    1440
accaaggacc gcctcttctt cgtcatggaa tatgtaaatg gtggagacct catgttccag    1500
attcagcggt cccgaaaatt tgatgagcct cgttctcggt tctatgccgc agaggtcaca    1560
tcagccctca tgtttctcca ccagcacgga gtgatctaca gggatttgaa actggacaac    1620
atccttctag atgcagaagg ccactgcaag ctggctgact ttgggatgtg caaggaaggg    1680
attatgaatg gtgtgacaac taccaccttc tgtgggactc ctgactacat agctccagag    1740
atcctacagg agttggagta cggcccctca gtggactggt gggccctggg ggtgctgatg    1800
tacgagatga tggctgggca gcccccccttt gaagctgaca acgaggacga cttgttcgaa    1860
tccatccttc atgatgatgt tctctatcct gtctggctta gcaaggaagc tgtcagcatc    1920
ctgaaagctt tcatgaccaa gaacccgcac aagcgcctgg gctgtgtggc agcgcagaac    1980
```

-continued

```
ggggaggacg ccatcaagca acatccattc ttcaaggaga ttgactgggt actgctggag   2040

cagaagaaaa tcaagccccc cttcaagccg agaattaaaa ccaaaagaga tgtcaataac   2100

tttgaccaag actttacgcg ggaagagcca atacttacac ttgtggatga agcaatcatt   2160

aagcagatca accaggaaga atttaaaggc ttctcctact ttggtgaaga cctgatgccc   2220

tgagaaactg aattc                                                     2235


<210> SEQ ID NO 4
<211> LENGTH: 737
<212> TYPE: PRT
<213> ORGANISM: Mus musculus

<400> SEQUENCE: 4

Met Val Val Phe Asn Gly Leu Leu Lys Ile Lys Ile Cys Glu Ala Val
 1               5                  10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Lys Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220

Lys Gln Glu Thr Pro Asp Glu Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
        275                 280                 285

Ala Pro Asn Cys Gly Val Asp Ala Arg Gly Ile Ala Lys Val Leu Ala
    290                 295                 300

Asp Leu Gly Val Thr Pro Asp Lys Ile Thr Asn Ser Gly Gln Arg Arg
305                 310                 315                 320

Lys Lys Leu Ala Ala Gly Ala Glu Ser Pro Gln Pro Ala Ser Gly Asn
                325                 330                 335
```

```
Ser Pro Ser Glu Asp Asp Arg Ser Lys Ser Ala Pro Thr Ser Pro Cys
            340                 345                 350

Asp Gln Glu Leu Lys Glu Leu Glu Asn Asn Ile Arg Lys Ala Leu Ser
        355                 360                 365

Phe Asp Asn Arg Gly Glu Glu His Arg Ala Ser Ser Ala Thr Asp Gly
    370                 375                 380

Gln Leu Ala Ser Pro Gly Glu Asn Gly Glu Val Arg Pro Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
        435                 440                 445

Asp Val Asp Cys Thr Met Thr Glu Lys Arg Ile Leu Ala Leu Ala Arg
    450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
        515                 520                 525

Ile Tyr Arg Asp Leu Lys Leu Asp Asn Ile Leu Leu Asp Ala Glu Gly
    530                 535                 540

His Cys Lys Leu Ala Asp Phe Gly Met Cys Lys Glu Gly Ile Met Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
        595                 600                 605

Ala Asp Asn Glu Asp Asp Leu Phe Glu Ser Ile Leu His Asp Asp Val
    610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ala Gln
                645                 650                 655

Asn Gly Glu Asp Ala Ile Lys Gln His Pro Phe Phe Lys Glu Ile Asp
            660                 665                 670

Trp Val Leu Leu Glu Gln Lys Lys Ile Lys Pro Pro Phe Lys Pro Arg
        675                 680                 685

Ile Lys Thr Lys Arg Asp Val Asn Asn Phe Asp Gln Asp Phe Thr Arg
    690                 695                 700

Glu Glu Pro Ile Leu Thr Leu Val Asp Glu Ala Ile Ile Lys Gln Ile
705                 710                 715                 720

Asn Gln Glu Glu Phe Lys Gly Phe Ser Tyr Phe Gly Glu Asp Leu Met
                725                 730                 735

Pro

<210> SEQ ID NO 5
```

<211> LENGTH: 2704
<212> TYPE: DNA
<213> ORGANISM: Rattus norvegicus

<400> SEQUENCE: 5
gaattccgga atccggcgag gaaatacatg cactcgctga gaatcgccgg cgccaggacg 60
cagcgccaca aggtgtagcg agtgagtggg gtggggcaag aggggaccca ggagtccccc 120
caggctccca gcgcgcctgc tcctgctctt caatcctgcc ctcggggcgg acggagtgac 180
ccccgccccg accatggtag tgttcaatgg ccttcttaag atcaaaatct gcgaggccgt 240
gagcttgaag cccacagcct ggtcgctgcg ccatgcggtg ggaccccggc cccagacgtt 300
ccttctggac ccctacattg cccttaacgt ggacgactcg cgcatcggcc aaacagccac 360
caagcagaag accaacagtc cggcctggca cgatgagttc gtcactgatg tgtgcaatgg 420
gcgcaagatc gagctggctg tctttcacga tgctcctatc ggctacgacg acttcgtggc 480
caactgcacc atccagttcg aggagctgct gcagaatggg agccgtcact tcgaggactg 540
gattgatctg gagccagaag gaaaagtcta cgtgatcatc gatctctcgg gatcatcggg 600
cgaagcccct aaagacaatg aagaacgagt gtttagggag cggatgcggc caaggaagcg 660
ccaaggggct gtcaggcgca gggtccacca ggtcaatggc cacaagttca tggccaccta 720
cttgcggcag cccacctact gctcccactg tagggatttc atctggggtg tcataggaaa 780
acagggatat caatgtcaag tttgtacctg cgtcgtccac aaacgatgcc atgagctcat 840
tattacgaag tgcgctgggc taaagaaaca ggaaacccct gacgaggtgg gctcccaacg 900
cttcagcgtc aacatgcccc acaagttcgg gatccacaac tacaaggtcc ccacgttctg 960
tgaccactgt ggctccctgc tctggggcct cttgcggcag ggcctgcagt gtaaagtctg 1020
caaaatgaat gttcaccgtc gatgcgagac caacgtggct cccaattgtg gggtggacgc 1080
cagaggaatt gccaaggtgc tggccgatct tggcgttact ccagacaaaa tcaccaacag 1140
tggccagaga aggaaaaagc tcgctgctgg tgctgagtcc ccacagccgg cttctggaaa 1200
ctccccatca gaagacgacc gatccaagtc agcgcccacc tcccccttgtg accaggaact 1260 aaaagaactt gaaaacaaca tccggaaggc cttgtcattt gacaaccgag gagaggagca 1320
ccgagcctcg tcgtctactg atggccagct ggcaagccct ggcgagaacg gtgaagtccg 1380
gcaaggccag gccaagcgct tgggcctgga tgagttcaac ttcatcaagg tgttaggcaa 1440
aggcagcttt ggcaaggtca tgctggccga gctcaagggt aaggatgaag tctatgctgt 1500
gaaggtctta aagaaggacg tcatcctgca ggatgacgac gtggactgca cgatgacaga 1560
gaagaggatt ttggctctgg cgcggaaaca ccccttatcta acccaactct attgctgctt 1620
ccagaccaag gaccggctct tcttcgtcat ggaatatgta aacggtggag acctcatgtt 1680
ccagattcag cggtcccgaa aattcgatga gcctcgttcc gggttctatg ctgccgaggt 1740
cacatctgct ctcatgtttc tccaccaaca tggagtgatc tacagggatt tgaaactgga 1800
caacatcctt ctagatgcag aaggtcactc caagctggct gactttggga tgtgcaagga 1860
agggattctg aatggcgtga caactaccac cttctgtggg actcctgact acatagctcc 1920
agagatcctg caggagttgg agtacggccc ctcagtggac tggtgggccc tgggcgtgct 1980
gatgtacgag atgatggccg ggcagccccc ctttgaagct gacaacgagg acgacttgtt 2040
tgaatccatc cttcacgatg acgttctcta ccctgtctgg cttagcaagg aggctgtcag 2100
catcctgaaa gctttcatga ccaagaaccc gcacaagcgc ctgggctgcg tggcagcaca 2160
gaacggggaa gatgccatca agcaacatcc attcttcaag gagattgact gggtactgct 2220

-continued

```
ggagcagaag aaaatgaagc ccccccttcaa gccgagaatt aaaaccaaga gagatgtcaa   2280

taactttgac caagacttta cccgggaaga gccaatactt acacttgtgg atgaagcaat   2340

cgtgaagcag atcaaccagg aagaattcaa aggcttctcc tactttggtg aagacctgat   2400

gccctgagaa actgcttcac atggagttag ctcactgcaa ggagggtgtt gagacaatcc   2460

cgtgttgcag aggctcagaa tgtctcgaac tattcgtcct ccccagagcc ccagtcccac   2520

atctgctctc ttatttattg catcccctca tcccaggccc tgtccttccc caccctccca   2580

gtgaccagaa ggccctcttt ggtccagact caccaagatc acagatttga actgcgtctg   2640

ctctgtgtgc agtgctaggt ctggagtagc cgtccaccca caaccctgaa gcagcccgga   2700

attc                                                                2704
```

```
<210> SEQ ID NO 6
<211> LENGTH: 737
<212> TYPE: PRT
<213> ORGANISM: Rattus norvegicus

<400> SEQUENCE: 6

Met Val Val Phe Asn Gly Leu Leu Lys Ile Lys Ile Cys Glu Ala Val
 1               5                  10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Lys Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220

Lys Gln Glu Thr Pro Asp Glu Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
        275                 280                 285
```

-continued

```
Ala Pro Asn Cys Gly Val Asp Ala Arg Gly Ile Ala Lys Val Leu Ala
    290                 295                 300

Asp Leu Gly Val Thr Pro Asp Lys Ile Thr Asn Ser Gly Gln Arg Arg
305                 310                 315                 320

Lys Lys Leu Ala Ala Gly Ala Glu Ser Pro Gln Pro Ala Ser Gly Asn
                325                 330                 335

Ser Pro Ser Glu Asp Asp Arg Ser Lys Ser Ala Pro Thr Ser Pro Cys
            340                 345                 350

Asp Gln Glu Leu Lys Glu Leu Glu Asn Asn Ile Arg Lys Ala Leu Ser
        355                 360                 365

Phe Asp Asn Arg Gly Glu Glu His Arg Ala Ser Ser Ser Thr Asp Gly
    370                 375                 380

Gln Leu Ala Ser Pro Gly Glu Asn Gly Glu Val Arg Gln Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
        435                 440                 445

Asp Val Asp Cys Thr Met Thr Glu Lys Arg Ile Leu Ala Leu Ala Arg
    450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Gly Phe Tyr
            500                 505                 510

Ala Ala Glu Val Thr Ser Ala Leu Met Phe Leu His Gln His Gly Val
        515                 520                 525

Ile Tyr Arg Asp Leu Lys Leu Asp Asn Ile Leu Leu Asp Ala Glu Gly
    530                 535                 540

His Ser Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
        595                 600                 605

Ala Asp Asn Glu Asp Asp Leu Phe Glu Ser Ile Leu His Asp Asp Val
    610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ala Gln
                645                 650                 655

Asn Gly Glu Asp Ala Ile Lys Gln His Pro Phe Phe Lys Glu Ile Asp
            660                 665                 670

Trp Val Leu Leu Glu Gln Lys Lys Met Lys Pro Pro Phe Lys Pro Arg
        675                 680                 685

Ile Lys Thr Lys Arg Asp Val Asn Asn Phe Asp Gln Asp Phe Thr Arg
    690                 695                 700

Glu Glu Pro Ile Leu Thr Leu Val Asp Glu Ala Ile Val Lys Gln Ile
705                 710                 715                 720
```

Asn Gln Glu Glu Phe Lys Gly Phe Ser Tyr Phe Gly Glu Asp Leu Met
725 730 735

Pro

<210> SEQ ID NO 7
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 7

Glu Ala Val Ser Leu Lys Pro Thr
1 5

<210> SEQ ID NO 8
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 8

Asn Gly Leu Leu Lys Ile Lys
1 5

<210> SEQ ID NO 9
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 9

Leu Ala Val Phe His Asp Ala Pro Ile Gly Tyr
1 5 10

<210> SEQ ID NO 10
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 10

Asp Asp Phe Val Ala Asn Cys Thr Ile
1 5

<210> SEQ ID NO 11
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 11

Trp Ile Asp Leu Glu Pro Glu Gly Arg Val
1 5 10

<210> SEQ ID NO 12
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 12

His Ala Val Gly Pro Arg Pro Gln Thr Phe
1 5 10

<210> SEQ ID NO 13
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 13
aagatcaaaa tctgcgaggc c 21

<210> SEQ ID NO 14
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 14
aagatcgagc tggctgtctt t 21

<210> SEQ ID NO 15
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 15
aactacaagg tccctacctt c 21

<210> SEQ ID NO 16
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 16
aaaaagctca ttgctggtgc c 21

<210> SEQ ID NO 17
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 17
gcaattaaac agctggatt 19

<210> SEQ ID NO 18
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 18
uuaauuugaa cgugaaggac t 21

<210> SEQ ID NO 19
<211> LENGTH: 21
<212> TYPE: DNA

-continued

<213> ORGANISM: Artificial Sequence
<220> FEATURE:
<223> OTHER INFORMATION: Synthetically generated oligonucleotide

<400> SEQUENCE: 19
aucuugucga ugcauuucut g 21

<210> SEQ ID NO 20
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 20
ucaaaugaca aggccuuccg g 21

<210> SEQ ID NO 21
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 21
ttgcccaaca ccttgatgaa g 21

<210> SEQ ID NO 22
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 22
gcagcacgac uucuucaag 19

<210> SEQ ID NO 23
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 23
aactgtggtg attccgtgtt tggg 24

<210> SEQ ID NO 24
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 24
tctggctgtc ccaggaaatt ctgt 24

<210> SEQ ID NO 25
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 25
cctcaatgtg tcactctgtg caaggt 26

-continued

```
<210> SEQ ID NO 26
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 26

atgatgccag caagtgggag tttg                                          24


<210> SEQ ID NO 27
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 27

atttcttgat gccgaacgcc gatg                                          24


<210> SEQ ID NO 28
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 28

agacttaaac tgggcaagtc actcgg                                        26


<210> SEQ ID NO 29
<211> LENGTH: 6
<212> TYPE: DNA
<213> ORGANISM: Artificial Sequence
<220> FEATURE:
<223> OTHER INFORMATION: Synthetically generated oligonucleotide
      <220<
<221> NAME/KEY: misc_feature
<222> LOCATION: 2, 3
<223> OTHER INFORMATION: n = g, c, a or t

<400> SEQUENCE: 29

ggnngg                                                               6
```

METHODS OF MODULATING ANGIOGENESIS

CROSS-REFERENCE TO RELATED APPLICATIONS

This application is a continuation of pending International Application Number PCT/US2008/052350, filed on Jan. 29, 2008, which claims the benefit of priority of U.S. Ser. No. 60/898,085, filed Jan. 29, 2007, the contents of which are hereby incorporated by reference in their entirety.

FEDERALLY SPONSORED RESEARCH OR DEVELOPMENT

This invention was made with Government support under Grant No. NIDDK R01 DK53105 awarded by the National Institutes of Health. The U.S. Government has certain rights in the invention.

TECHNICAL FIELD

This invention relates to methods of modulating angiogenesis using compounds that specifically inhibit or enhance protein kinases.

BACKGROUND

Vascular endothelial growth factor (VEGF) has many important effects on the vasculature, including vasodilation, increased capillary permeability, vasculogenesis, and angiogenesis (1). Many of these biological actions of VEGF involve signaling mediated by nitric oxide (NO) (2), likely both by induction of gene expression and by enzymatic activation of endothelial NO synthase (eNOS) (3). Activation of eNOS by VEGF is mediated through several pathways, including an increase in intracellular concentrations of $Ca^{2+}$ ($[Ca^{2+}]_i$) and by phosphorylation of several residues of eNOS. Protein kinase Akt can directly phosphorylates eNOS on Ser1179 (the bovine homologue of human Ser1177), and this residue is considered one of the most important for regulation of eNOS activity by phosphorylation (4). Activation of eNOS by increased $[Ca^{2+}]_i$, is quick and lasts only a few minutes, whereas eNOS Ser1179 phosphorylation results in more sustained activation, lasting half an hour or longer (5). Certain growth factors and hormones, including VEGF, activate eNOS by both mechanisms (6). In contrast, activation of eNOS by insulin is largely dependent on eNOS Ser1179 phosphorylation and independent of $[Ca^{2+}]_i$ (6, 7).

Certain signaling pathways activated by VEGF is mediated by protein kinase C (PKC). VEGF increases PKC activity and PKCβ activation contributes to VEGF-stimulated endothelial cell proliferation (8) and increased vascular permeability (9). Consistent with these observations, inhibitors of PKC block phosphorylation of eNOS Ser1179 (10) and NO production (11) stimulated by VEGF in endothelial cells. Both insulin and VEGF increase eNOS Ser1179 phosphorylation through activation of PI3K and Akt (12, 13). Importantly, PKC activation by phorbol ester decreases insulin-stimulated PI3K activity (14), but inhibition of PI3K does not block PKC activation stimulated by VEGF (8, 15).

SUMMARY

The present invention is based on the discovery that PKCϵ plays a role in VEGF-induced NO production in endothelial cells, and therefore is a therapeutic target for disorders associated with angiogenesis.

In one aspect, the invention provides methods for inhibiting angiogenesis in a subject (i.e., a mammal, e.g., a human or non-human experimental animal or veterinary subject). The methods include administering to the subject a therapeutically effective amount of a composition comprising a specific inhibitor of protein kinase C epsilon (PKCϵ). A number of suitable inhibitors are known, including inhibitory nucleic acids, e.g., antisense, RNAi, ribozyme, or morpholino oligo. In some embodiments, the inhibitor is an antibody that binds specifically to PKCϵ, e.g., a monoclonal, polyclonal, humanized, chimeric, or monospecific antibody or antigen-binding fragment thereof. In some embodiments, the inhibitor is a small molecule or peptide inhibitor of PKCϵ, e.g., ϵV1-1, ϵV1-2, ϵV1-3, ϵV1-4, ϵV1-5 or ϵV1-6.

In one embodiment, the nucleic acid is a small interfering RNA (siRNA) (e.g., a double stranded siRNA) that targets PKCϵ (e.g., human PKCϵ). For example, the siRNA is a nucleic acid molecule comprising 16-30 nucleotides (16-30 nucleotides in each strand, in a double stranded siRNA) that are substantially identical (e.g., at least 80%, 85%, 90%, 95% 97%, 99%, or 100% identical) to a target region in a PKCϵ nucleic acid (e.g., PKCϵ mRNA). In various embodiments, the siRNA agents are chemically synthesized, transcribed in vitro, or expressed in vivo (e.g., by introduction of DNA encoding the siRNA). A double stranded siRNA can either have blunt ends or can have overhangs (e.g., overhangs of 1-4 nucleotides) from one or both 3' ends of the agent.

In various embodiments, the siRNA targets a region within nucleotides 200-250, 400-450, 900-980, or 1140-1190 of SEQ ID NO:1 (i.e., the siRNA is at least partially complementary to a sequence of an mRNA encoded by one of these regions). For example, the siRNA targets a sequence corresponding to nucleotides 223 to 244, 429 to 450, 942 to 963, or 1158 to 1179. These target sequences are as follows: 5'-AAGAT CAAAA TCTGC GAGGCC-3' (SEQ ID NO:13), 5'-AAGAT CGAGC TGGCTG TCTTT-3' (SEQ ID NO:14), 5'-AACTA CAAGG TCCCT ACCTTC-3' (SEQ ID NO:15), and 5'-AAAAA GCTCA TTGCT GGTGCC-3' (SEQ ID NO:16).

In various embodiments, the siRNA is an siRNA comprising a sequence that differs from the following sequence: UCAAAUGACAAGGCCUUCCgg (SEQ ID NO:20) by no more than 1, 2, 3, 4, or 5 nucleotides. In various embodiments, the siRNA targets the following sequence TTGCCCAACACCTTGATGAag (SEQ ID NO:21) (corresponding to nucleotides 1360-1382 of NM_001111120).

The methods described herein are particularly useful in the treatment of subjects who have or are at risk for an ocular disorder associated with abnormally increased angiogenesis, e.g., oxygen-induced retinopathy-of-prematurity, oxygen-induced retinopathy, or proliferative diabetic retinopathy. In these embodiments, the composition can be administered to the eye of the subject. In one embodiment, an siRNA (e.g., an siRNA described herein) is administered to the eye of the subject.

In some embodiments, the subject has a solid tumor; in these embodiments, the composition can be administered to or near the solid tumor.

In another aspect, the invention provides methods for enhancing angiogenesis in a tissue of a subject, e.g., an ischemic tissue. The methods include administering a therapeutically effective amount of a specific enhancer of PKCϵ to the tissue. In some embodiments, the enhancer is a PKCϵ polypeptide or nucleic acid encoding a PKCϵ polypeptide. In some embodiments, the tissue is an ischemic limb, e.g., a limb of a subject having diabetes mellitus, or cardiac tissue, e.g., in a subject having coronary artery disease.

In a further aspect, the invention provides methods for identifying candidate compounds for modulating, e.g., enhancing or inhibiting, angiogenesis in a tissue. The methods include providing a sample comprising PKCϵ; contacting the sample with a test compound; and evaluating an effect of the test compound on levels or activity of the PKCϵ in the sample.

A test compound that decreases levels or activity of PKCϵ in the sample is a candidate compound for inhibiting angiogenesis. In some embodiments, the test compound inhibits PKCϵ phosphorylation of a substrate, e.g., Akt, eNOS, or AMPK.

The methods can include evaluating PKCϵ-mediated downregulation of VEGFR2. In some embodiments, the test compound inhibits expression or activity of VEGFR2. In some embodiments, the sample comprises a cell expressing PKCϵ, and the test compound decreases levels of PKCϵ mRNA or protein in the cell. In some embodiments, the methods also include selecting a candidate compound that decreases levels or activity of PKCϵ in the sample; administering the candidate compound to a tissue; and evaluating angiogenesis in the tissue. A decrease in angiogenesis in the tissue indicates that the candidate compound is a candidate therapeutic agent for inhibiting angiogenesis in a tissue.

A test compound that increases levels or activity of PKCϵ in the sample is a candidate compound for enhancing angiogenesis. In some embodiments, the test compound enhances PKCϵ phosphorylation of a substrate, e.g., eNOS, Akt, or AMPK. In some embodiments, the sample comprises a cell expressing PKCϵ, and the test compound increases levels of PKCϵ mRNA or protein in the cell. In some embodiments, the methods also include selecting a candidate compound that increases levels or activity of PKCϵ in the sample; administering the candidate compound to a tissue; and evaluating angiogenesis in the tissue. An increase in angiogenesis in the tissue indicates that the candidate compound is a candidate therapeutic agent for enhancing angiogenesis in a tissue.

In a further aspect, the invention provides methods for treating peripheral or myocardial ischemia in a tissue. The methods include administering to the tissue a composition comprising a nucleic acid encoding PKCϵ, in an amount and under conditions sufficient to achieve therapeutic levels of PKCϵ in the tissue and enhance angiogenesis in the tissue, thereby treating the ischemia in the tissue.

In some embodiments, the nucleic acid encoding PKCϵ is in a viral delivery vector, e.g., an adenovirus, retrovirus, adeno-associated virus, or herpes simplex virus-1.

A therapeutically effective amount can slow, cure, heal, alleviate, relieve, alter, remedy, ameliorate, improve or affect the condition (e.g., an angiogenesis-related condition described herein), a symptom of the condition, or the predisposition toward the condition, e.g., by at least 10%.

The abbreviations used herein include $[Ca^{2+}]_i$, intracellular $Ca^{2+}$ concentration; DAG, diacylglycerol; eNOS, endothelial nitric oxide synthase; GFX, GF109203X; NO, nitric oxide; PKC, protein kinase C; PMA, phorbol-12-myristate-13-acetate; VEGF, vascular endothelial growth factor.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A depicts data from Western blot analysis of phospho-Akt (Thr308), phospho-Akt (Ser473), and Akt (n=5, * $p<0.05$). FIG. 1B depicts data from Western blot analysis of phospho-eNOS (Ser1179) and eNOS (n=4, * $p<0.05$).

FIGS. 1C and 1D depict data from Western blot analysis of phospho-Akt (Ser473) and Akt (n=5, * $p<0.05$).

FIG. 2A depicts phospho-Akt (Ser473), and Akt (n=4, * $p<0.05$), FIG. 2B depicts phospho-eNOS (Ser1179), and eNOS (n=5, * $p<0.05$), and FIG. 2C depicts phospho-Akt (Ser473), Akt, phospho-eNOS (Ser1179), and eNOS (n=4, * $p<0.05$) analyses.

FIG. 5A is a set of Western blots representing 3 independent experiments with similar results. Lane 11: no protein loaded. Lane 12: bovine brain lysate, used as a positive control. Lane 13: molecular weight standards. FIGS. 5B-5D are bar graphs representing protein levels in cells treated with siRNAs targeting PKCα, δ, or ϵ.

(FIG. 6A, n=5. b, FIG. 6B, n=3. * $p<0.05$).

DETAILED DESCRIPTION

Figure 1A:
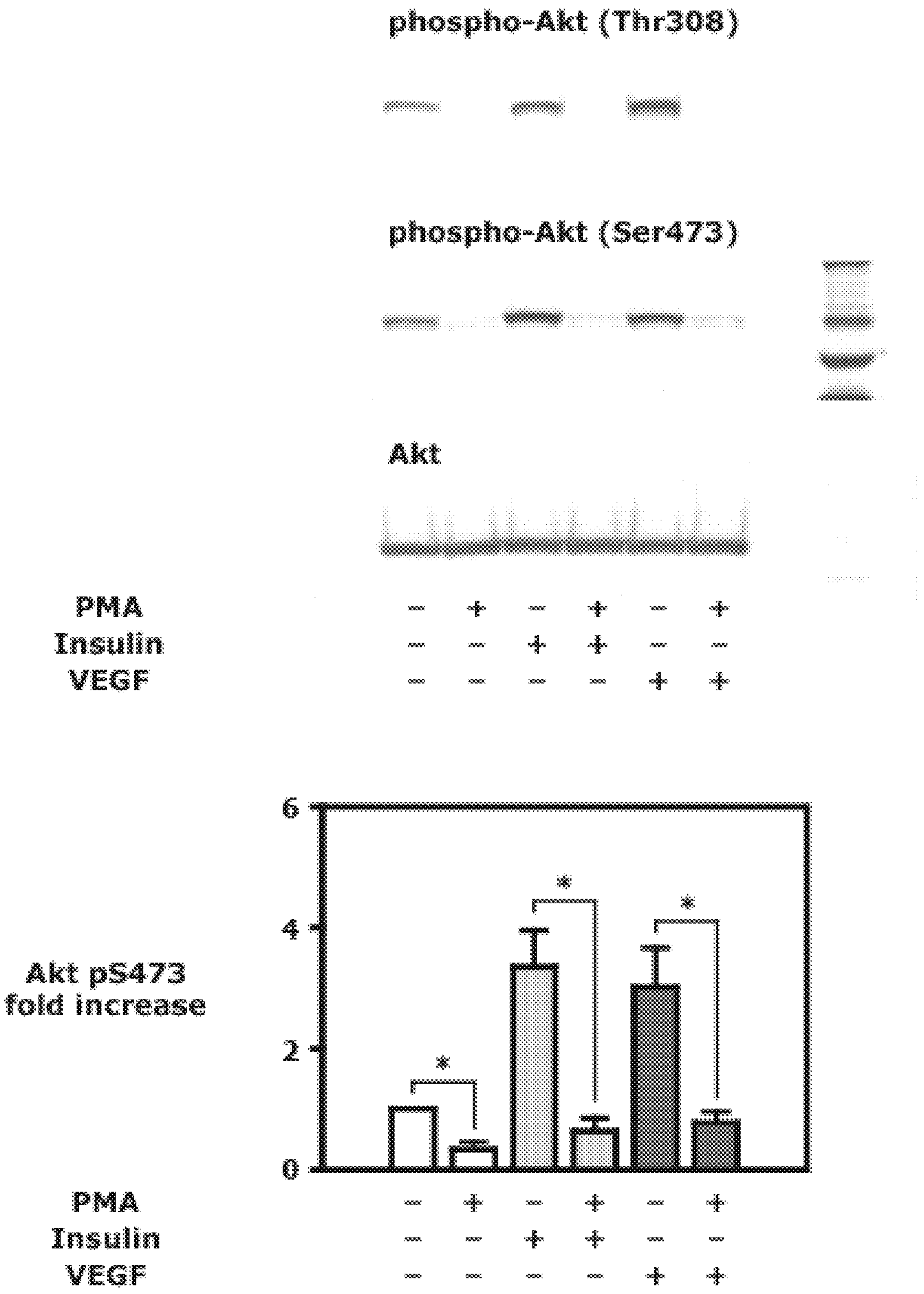
FIGS. 1A-D are sets of immunoblots and bar graphs depicting the effect of PMA on phosphorylation of Akt and eNOS stimulated by insulin or VEGF. Representative immunoblots are shown above mean data for the phospho-protein normalized to the control condition.

To clarify the differential effects of PKC activation on eNOS phosphorylation stimulated by either VEGF or insulin, the present inventors characterized the regulation of Akt Ser473 and eNOS Ser1179 phosphorylation in BAEC during PKC activation. The results showed that general PKC activation potently decreased Akt activation stimulated by both insulin and VEGF. Surprisingly, this was only associated with inhibition of eNOS Ser1179 phosphorylation stimulated by insulin, not by VEGF. Therefore the involvement of individual PKC isoforms in VEGF-stimulated Akt and eNOS phosphorylation was characterized using RNA interference (RNAi). The results show that PKCα negatively regulates VEGF-stimulated Akt phosphorylation. In contrast, PKCε is necessary for PI3K-mediated Akt and eNOS phosphorylation, and for NO synthase activation stimulated by VEGF, but not by insulin. PKCε contributes to VEGF-stimulated Erk activation by regulating Vascular Endothelial Growth Factor Receptor 2 (VEGFR2, also known as KDR) expression and activation, whereas PKCα has opposite effects. This discovery of PKCε's role in VEGF-induced biological effects in endothelial cells described herein identifies PKCε as a therapeutic target for disorders associated with angiogenesis. Differential manipulation of PKCε expression or activity may be used to modify (e.g., enhance or inhibit) angiogenesis in subjects that have, or are at risk for, conditions such as diabetic proliferative retinopathy, ischemic myocardium, or ischemic extremities.

Protein Kinase C—Epsilon Isoform

Protein kinase C (PKC) is a membrane-associated enzyme that is regulated by a number of factors, including membrane phospholipids, calcium, and membrane lipids such as diacylglycerols that are liberated in response to the activities of phospholipases (Bell et al. J. Biol. Chem., 1991, 266:4661-4664; Nishizuka, Science, 1992, 258:607-614. The protein kinase C isozymes, alpha, beta-1, beta-2 and gamma, require membrane phospholipid, calcium and diacylglycerol/phorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipid for their activation. PKC- and isozyme-specific (e.g., PKC specific) modulators are described, e.g., in Goekjian et al. Current Medicinal Chemistry, 1999, 6:877-903; Way et al., Trends Pharmacol Sci, 2000, 21:181-7, and in U.S. Pat. No. 5,843,935.

Basta et al. (1992) isolated cDNA corresponding to the epsilon form of protein kinase C. The human sequences are available in GenBank at Accession Nos. NM_005400.2 (nucleic acid) and NP_005391.1 (amino acid). At the amino acid level, the deduced human epsilon sequence showed 98 to 99% identity with the mouse and rat sequences. The mouse sequences are Acc. Nos. NM_011104.1 (nucleic acid) and NP_035234.1 (amino acid). The rat sequences are NM_017171.1 (nucleic acid) and NP_058867.1 (amino acid). Exemplary PKC epsilon nucleotide and amino acid sequences are shown in Table 1.

TABLE 1

PKC epsilon nucleotide and amino acid sequences

| Name; GenBank ® Acc. No. | Sequence |
|---|---|
| | (SEQ ID NO:1) |
| *Homo sapiens* protein kinase C, epsilon nucleotide sequence; NM_005400, GI:47157326 | GAACCCGGCGAGGAAATACATGCACTGGCTGAGAATCGCCCGCGCCAGGGCGCA<br>ACGCCACAAGGTGTAGGGAGTGTGCGGGGTGGGGCGAAAGGGGACCCAAGAGTC<br>CCTGTGGCTCGGAGTGCCGGGCCGTCGGTTCTTCATTCCTGCCCTCGGGGCAGA<br>CGGAGTGACCCCGGCCCCCACTCCCCGCCCCGACCATGGTAGTGTTCAATGGCC<br>TTCTTAAGATCAAAATCTGCGAGGCCGTGAGCTTGAAGCCCACAGCCTGGTCGC<br>TGCGCCATGCGGTGGGACCCCGGCCGCAGACTTTCCTTCTCGACCCCTACATTG<br>CCCTCAATGTGGACGACTCGCGCATCGGCCAAACGGCCACCAAGCAGAAGACCA<br>ACAGCCCGGCCTGGCACGACGAGTTCGTCACCGATGTGTGCAACGGACGCAAGA<br>TCGAGCTGGCTGTCTTTCACGATGCCCCCATAGGCTACGACGACTTCGTGGCCA<br>ACTGCACCATCCAGTTTGAGGAGCTGCTGCAGAACGGGAGCCGCCACTTCGAGG<br>ACTGGATTGATCTGGAGCCAGAAGGAAGAGTGTATGTGATCATCGATCTCTCAG<br>GGTCGTCGGGTGAAGCCCCTAAAGACAATGAAGAGCGTGTGTTCAGGGAACGCA<br>TGCGGCCGAGGAAGCGGCAGGGGGCCGTCAGGCGCAGGGTCCATCAGGTCAACG<br>GCCACAAGTTCATGGCCACCTATCTTCGGCAGCCCACCTACTGCTCCCATTGCA<br>GAGACTTCATCTGGGGTGTCATAGGAAAGCAGGGATACCAGTGTCAAGTCTGCA<br>CCTGCGTGGTCCACAAGCGGTGCCACGAGCTCATAATCACAAAGTGTGCTGGGT<br>TAAAGAAGCAGGAGACCCCCGACCAGGTGGGCTCCCAGCGGTTCAGCGTCAACA<br>TGCCCCACAAGTTCGGTATCCACAACTACAAGGTCCCTACCTTCTGCGATCACT<br>GTGGGTCCCTGCTCTGGGGACTCTTGCGGCAGGGTTTGCAGTGTAAAGTCTGCA<br>AAATGAATGTTCACCGTCGATGTGAGACCAACGTGGCTCCCAACTGTGGAGTGG |

TABLE 1-continued

PKC epsilon nucleotide and amino acid sequences

| Name; GenBank ® Acc. No. | Sequence |
| --- | --- |
| | ATGCCAGAGGAATCGCCAAAGTACTGGCCGACCTGGGCGTTACCCCAGACAAAA |
| | TCACCAACAGCGGCCAGAGAAGGAAAAAGCTCATTGCTGGTGCCGAGTCCCCGC |
| | AGCCTGCTTCTGGAAGCTCACCATCTGAGGAAGATCGATCCAAGTCAGCACCCA |
| | CCTCCCCTTGTGACCAGGAAATAAAAGAACTTGAGAACAACATTCGGAAAGCCT |
| | TGTCATTTGACAACCGAGGAGAGGAGCACCGGGCAGCATCGTCTCCTGATGGCC |
| | AGCTGATGAGCCCCGGTGAGAATGGCGAAGTCCGGCAAGGCCAGGCCAAGCGCC |
| | TGGGCCTGGATGAGTTCAACTTCATCAAGGTGTTGGGCAAAGGCAGCTTTGGCA |
| | AGGTCATGTTGGCAGAACTCAAGGGCAAAGATGAAGTATATGCTGTGAAGGTCT |
| | TAAAGAAGGACGTCATCCTTCAGGATGATGACGTGGACTGCACAATGACAGAGA |
| | AGAGGATTTTGGCTCTGGCACGGAAACACCCGTACCTTACCCAACTCTACTGCT |
| | GCTTCCAGACCAAGGACCGCCTCTTTTTCGTCATGGAATATGTAAATGGTGGAG |
| | ACCTCATGTTTCAGATTCAGCGCTCCCGAAAATTCGACGAGCCTCGTTCACGGT |
| | TCTATGCTGCAGAGGTCACATCGGCCCTCATGTTCCTCCACCAGCATGGAGTCA |
| | TCTACAGGGATTTGAAACTGGACAACATCCTTCTGGATGCAGAAGGTCACTGCA |
| | AGCTGGCTGACTTCGGGATGTGCAAGGAAGGGATTCTGAATGGTGTGACGACCA |
| | CCACGTTCTGTGGGACTCCTGACTACATAGCTCCTGAGATCCTGCAGGAGTTGG |
| | AGTATGGCCCCTCCGTGGACTGGTGGGCCCTGGGGGTGCTGATGTACGAGATGA |
| | TGGCTGGACAGCCTCCCTTTGAGGCCGACAATGAGGACGACCTATTTGAGTCCA |
| | TCCTCCATGACGACGTGCTGTACCCAGTCTGGCTCAGCAAGGAGGCTGTCAGCA |
| | TCTTGAAAGCTTTCATGACGAAGAATCCCCACAAGCGCCTGGGCTGTGTGGCAT |
| | CGCAGAATGGCGAGGACGCCATCAAGCAGCACCCATTCTTCAAAGAGATTGACT |
| | GGGTGCTCCTGGAGCAGAAGAAGATCAAGCCACCCTTCAAACCACGCATTAAAA |
| | CCAAAAGAGACGTCAATAATTTTGACCAAGACTTTACCCGGGAAGAGCCGGTAC |
| | TCACCCTTGTGGACGAAGCAATTGTAAAGCAGATCAACCAGGAGGAATTCAAAG |
| | GTTTCTCCTACTTTGGTGAAGACCTGATGCCCTGAGAGCCCACTGCAGTTGGAC |
| | TTTGCCGATGCTGCAAGAAGGGGTGCAGAGAAGACTCCTGTGTTGGAGACACTC |
| | AGCAGGTCTTGAACTACTTCTCCTCCTCGGAGCCCCAGTCCCATGTCCACTGTC |
| | TATTTATTGCATTCCCTTGCCCCAGGCCACCTCCTCCCCCTCCCACCTGGTGAC |
| | CAGAAGGCGCTCTCGGTTCTTGTCTCACCAGTAATGCAGACTCATTGGGTCAGC |
| | AATTAGCTGTATACACTGCCGTGTTTGGACCATTGGCAAGCCTGGTTCCACTCC |
| | TCAGGGGCTCCTGGCAGTGAAGCAACTTCAGTTCTTTTACTGCAAAGAACAGAA |
| | AAAAGAAAGAAAGCAAACAAGAAGACTCCGGCTCTGCTATCGGACACAGATCCT |
| | GATCCCTCTTGCTTCTTTTCCCTCCTGCACCGCAGCTTGCCATCCCTGCCCTTC |
| | TGTCCTGGAGAAGAGACTGGTGCTTCTCCGCACACACGAGGGAGGGCGCCCTTG |
| | AGGCATGCCCTCTGAGGGAGGGAGACCAGAGATGCAGGGATTGGCCAGCTGGGT |
| | TGGTTTGCTCTGGAATGGCTAACTCTTGCCTGCTTTGGTTTTAGCTTTTCAGCA |
| | TGCCAAAGTCATGTAAGTTTGTGTCTTGTGGAAGAAATCCTCTTTGTGGAAAAA |
| | GAAACAGGGTTTTGAACTCTGTTAACATTTGAAAAATATATTTTCAAATTCACT |
| | TTCTAATTGGCCAAAAGAGATGAGTTCCAGTCTGAATACAGGTAGATATTAAAG |
| | GGCTAATAAAAAATGAGAAACCGGTCGTCCAAGGTGGATGCTGTCAATGCCCGA |
| | GTGACACATGAGAGCTGTATGAATTGAGAGAAAAGGCAACAAGTAGCATTCTTC |
| | ATCATTCAAGTTCTACCTGGACACAAAGGCGAGGACCCTGGGGTTCCAACAAAG |
| | CTCAGCTCCCAGATTCTCTTTCCAGTTTCATCCTAAGTTCCTAGCATAAACACT |
| | ATTTATTTTCTGCAGCAGTGTGTTATTTTTGCGCACTTATACAAAATGGTAGTA |
| | CTACTGTGTTGTGGTTTTTAAACATTAAACATGTAAAGTTATATACGAAATATC |
| | TGCTTTTGGAATAAGCAGAATGAGGCTAAACATGGGTTATACAAAGGGTATCTG |
| | GAAACTGAAGAGCAACTTGTTAGAAAACTGACAATGTCGCAAGATGTACTCAGT |
| | TTTGTTTCTGTGTGACATGCAATGGCAACTCATGTGGACACTATTGAAGGGATG |
| | TGACATTACCTCCTGTAGATATGCTAACAGTGTTATTCTTTCATTTCCAAGGGT |
| | TCTCTGTGGCTTTGTGTATATGTTTCCCAGAGGTCATTTGATTACCTAATTTAC |
| | TGAACTGATTTAGCAGGGAATGGAATCCATTCCAACTATTGCACGTGGATTTCC |
| | CAGCTGCCCCTAAATATATATACTTGTGAGTGGCAAAGTGGCACTAATGAAGCT |
| | TTTGCCTTTTGTACATTTGAGATTTTTGTATATAGTGTTTGCTGCAAGGCCTGT |
| | GGAATTAATTCGTTGCATATAGAGGTATCAACTGCTGCATGTTCAGGCATATTA |
| | TAAAACTTTAGTCTATGAAAGAATAATTATAATAATGTCCAGGTGCAATACTCT |
| | GTAAGTCTATTGGTTCAAGTTACCGAGAGATAGGTGTGTTCCTTTATGGGGGAT |
| | GGGGGGGTGTGTTGGGGATTCTTTGTATTGTTTATTTCATTTTGGTTTATTTTA |
| | AAAGATGTAAACATATATTAAGCTATATTAAATCTCACATACAGTTCTTCTGTG |
| | CTCTATTATACCCTGATAGAGATGGGGGAGAGAAAGGAATGTTTTTGATGGTGG |
| | TTTCAAAGCTCGGACAGTAACTATCTTGAGCCCATTAGAGAGTCTGTGTCCATA |
| | TTTGCATCTGGCTGGTCATAGCCTTTGTTACTAATGATGACATTCAGTTCTCTT |
| | TTGTTTTTATTTTTTAAAAACTCAGGTGTAATTATTATCTGTTCTTAAGATAAT |
| | TGCAAATATTAAATATTATGATATATCAATTCATGTGTTTGGCATACCAGTGAA |
| | TGATGAAGAACATGAGATTAATTTAATTTATCTTCGGTAACTTGACATTCTGGA |
| | GAGAGACTATCTTCTGGAGTTGAGTACAAGCACAGAAACATCTTTACGGTGGCA |
| | TCATCTCATTTTTTAGGAAGACATGATAATACTGCCCATCATATTCATGTGTAA |
| | CTACTGTTCTTTCTTCTGCTTTCTTCACCATAATAAACTTTGGACAACCAAGCA |
| | AGCTCTAACCGCAATGCCAGATGGCCTTGTCCGAGGGCCTAGTGTTTGCACGGC |
| | AGTGGGAACTGGGCCTTTCCTACAGGACAACTGGCAAGTTTGCTGGGAAGTCAA |
| | ATAATACATTCCACCTGGCAGCTGAAGGCAGCCAGTCAGTCTGTCCCAGAAAGG |
| | GCCCTTTTCAGCACCCAAAGCTGGGCTGGCTGGGATGCCTCTGGCTGGTGAAGT |
| | TCTCACATAGGCTGATTTAAATCCAGCAAAGGTCTATAGAAAAAGGCTTGCGTG |
| | TTCGTTGAGTAATCATTGTTTCATTTTCATTTTTACGAGAGTTTGAAAATAGAC |
| | ACACTGTTAACACTTCTGCCAGTTTTTTCTGATCTTTCCAGCCCCACCCCCTTT |

TABLE 1-continued

PKC epsilon nucleotide and amino acid sequences

| Name; GenBank ® Acc. No. | Sequence |
|---|---|
| | CTCTTTCTCTCTCTCTCAAAGAAAAAAAAAATGGGAGTGCAAAAAAAACAAA |
| | GCCAAAAAATATATGAAGGATAGCTGTTCTTCTGTGTTCTCTCATTATGGACTT |
| | TGTGAAGTAGAAACATAATTTTTTTCCTCCAkAGGTGAAAAAACAATGCATTC |
| | TTGCTTTAAAAAAAAAAAAGAAGGCTAAAAAATTACCTCTTTTTAAATTATGTG |
| | CAAAATAATTCTGGCTAACTGTAAAATGTATTCAATTTTAGGATTTTTTTTTT |
| | TGTATTGTGATGCTTTATTTGTACATTTTTTTCCTTTCTGGATGTAATTTTAAT |
| | CTCTTGCCATTCATTAGTGTTATTTCATTGTAAACGTTATTGTGCCAAATGTAC |
| | TGTATTCAAAAGGATGTGAATGTGTATTGTTTCAGAACCTAATAAATACAATGA |
| | CGTTAAGTCTTAAAAAAAAAAAAAAAAAA |
| | (SEQ ID NO: 2) |
| *Homo sapiens* | MVVFNGLLKIKICEAVSLKPTAWSLRHAVGPRPQTFLLDPYIALNVDDSRIGQT |
| protein kinase | ATKQKTNSPAWHDEFVTDVCNGRKIELAVFHDAPIGYDDFVANCTIQFEELLQN |
| C, epsilon | GSRHFEDWIDLEPEGRVYVIIDLSGSSGEAPKDNEERVFRERMRPRKRQGAVRR |
| amino acid | RVHQVNGHKFMATYLRQPTYCSHCRDFIWGVIGKQGYQCQVCTCVVHKRCHELI |
| sequence; | ITKCAGLKKQETPDQVGSQRFSVNMPHKFGIHNYKVPTFCDHCGSLLWGLLRQG |
| NP_005391.1, | LQCKVCKMNVHRRCETNVAPNCGVDARGIAKVLADLGVTPDKITNSGQRRKKLI |
| GI:4885563 | AGAESPQPASGSSPSEEDRSKSAPTSPCDQEIKELENNIRKALSFDNRGEEHRA |
| | ASSPDGQLMSPGENGEVRQGQAKRLGLDEFNFIKVLGKGSFGKVMLAELKGKDE |
| | VYAVKVLKKDVILQDDDVDCTMTEKRILALARKHPYLTQLYCCFQTKDRLFFVM |
| | EYVNGGDLMFQIQRSRKFDEPRSRFYAAEVTSALMFLHQHGVIYRDLKLDNILL |
| | DAEGHCKLADFGMCKEGILNGVTTTTFCGTPDYIAPEILQELEYGPSVDWWALG |
| | VLMYEMMAGQPPFEADNEDDLFESILHDDVLYPVWLSKEAVSILKAFMTKNPHK |
| | RLGCVASQNGEDAIKQHPFFKEIDWVLLEQKKIKPPFKPRIKTKRDVNNFDQDF |
| | TREEPVLTLVDEAIVKQINQEEFKGFSYFGEDLMP |
| | (SEQ ID NO: 3) |
| *Mus musculus* | GAATTCACCATGGTAGTGTTCAATGGCCTTCTTAAGATCAAAATCTGCGAGGCG |
| protein kinase | GTGAGCTTGAAGCCCACAGCCTGGTCGCTGCGCCATGCGGTGGGACCCCGGCCA |
| C, epsilon | CAGACGTTCCTTTTGGACCCCTACATTGCCCTTAACGTGGACGACTCGCGCATC |
| nucleotide | GGCCAAACAGCCACCAAGCAAAAGACCAACAGCCCGGCCTGGCACGATGAGTTC |
| sequence; | GTCACCGATGTGTGCAATGGGCGCAAGATCGAGCTGGCTGTCTTTCACGACGCT |
| NM_011104.1, | CCTATCGGCTACGACGACTTCGTGGCCAACTGCACCATCCAGTTCGAGGAGCTG |
| GI:6755083 | CTGCAGAATGGGAGCCGTCACTTCGAGGACTGGATTGACCTGGAGCCAGAAGGA |
| | AAAGTGTACGTGATCATCGATCTCTCGGGATCATCGGGTGAAGCCCCTAAAGAC |
| | AATGAAGAACGAGTGTTCAGGGAGCGTATGCGGCCAAGGAAGCGGCAAGGGGCT |
| | GTCAGGCGCAGGGTCCACCAGGTCAATGGCCACAAGTTCATGGCCACCTACTTG |
| | CGGCAACCCACCTACTGCTCCCACTGCAGAGATTTCATCTGGGGTGTCATAGGA |
| | AAACAGGGATATCAATGTCAAGTTTGCACTTGCGTTGTCCACAAGCGATGTCAT |
| | GAGCTCATTATTACAAAGTGCGCTGGGCTGAAGAAACAGGAAACCCCTGACGAG |
| | GTGGGCTCCCAACGGTTCAGCGTCAACATGCCCCACAAGTTCGGGATCCACAAC |
| | TACAAGGTCCCCACGTTCTGTGACCACTGTGGGTCCCTGCTCTGGGGCCTCTTG |
| | CGGCAGGGCTTGCAGTGTAAAGTCTGCAAAATGAATGTTCACCGGCGATGTGAG |
| | ACCAATGTGGCTCCCAACTGTGGGGTAGACGCCAGAGGAATTGCCAAAGTGCTG |
| | GCTGACCTTGGTGTTACTCCAGACAAAATCACCAACAGTGGCCAAAGGAGGAAA |
| | AAGCTCGCTGCTGGTGCTGAGTCCCCACAGCCGGCTTCTGGAAACTCCCCATCT |
| | GAAGACGACCGATCCAAGTCAGCGCCCACCTCCCCTTGTGACCAGGAACTAAAA |
| | GAACTTGAAAACAACATTCGGAAGGCCTTGTCATTTGACAACCGAGGAGAGGAG |
| | CACCGAGCGTCGTCGGCCACCGATGGCCAGCTGGCAAGCCCCGGAGAGAACGGG |
| | GAAGTCCGGCCAGGCCAGGCCAAGCGCTTGGGGCTGGATGAGTTCAACTTCATC |
| | AAGGTGTTGGGCAAAGGCAGCTTTGGCAAGGTCATGTTGGCGGAACTCAAAGGC |
| | AAAGATGAAGTCTACGCTGTGAAGGTCTTGAAGAAGGACGTTATCCTACAAGAC |
| | GATGATGTGGACTGCACAATGACAGAGAAGAGGATTTTGGCTCTGGCTCGGAAA |
| | CACCCTTATCTAACCCAACTCTATTGCTGCTTCCAGACCAAGGACCGCCTCTTC |
| | TTCGTCATGGAATATGTAAATGGTGGAGACCTCATGTTCCAGATTCAGCGGTCC |
| | CGAAAATTTGATGAGCCTCGTTCTCGGTTCTATGCCGCAGAGGTCACATCAGCC |
| | CTCATGTTTCTCCACCAGCACGGAGTGATCTACAGGGATTTGAAACTGGACAAC |
| | ATCCTTCTAGATGCAGAAGGCCACTGCAAGCTGGCTGACTTTGGGATGTGCAAG |
| | GAAGGGATTATGAATGGTGTGACAACTACCACCTTCTGTGGGACTCCTGACTAC |
| | ATAGCTCCAGAGATCCTACAGGAGTTGGAGTACGGCCCCTCAGTGGACTGGTGG |
| | GCCCTGGGGGTGCTGATGTACGAGATGATGGCTGGGCAGCCCCCCTTTGAAGCT |
| | GACAACGAGGACGACTTGTTCGAATCCATCCTTCATGATGATGTTCTCTATCCT |
| | GTCTGGCTTAGCAAGGAAGCTGTCAGCATCCTGAAAGCTTTCATGACCAAGAAC |
| | CCGCACAAGCGCCTGGGCTGTGTGGCAGCGCAGAACGGGGAGGACGCCATCAAG |
| | CAACATCCATTCTTCAAGGAGATTGACTGGGTACTGCTGGAGCAGAAGAAAATC |
| | AAGCCCCCCTTCAAGCCGAGAATTAAAACCAAAAGAGATGTCAATAACTTTGAC |
| | CAAGACTTTACGCGGGAAGAGCCAATACTTACACTTGTGGATGAAGCAATCATT |
| | AAGCAGATCAACCAGGAAGAATTTAAAGGCTTCTCCTACTTTGGTGAAGACCTG |
| | ATGCCCTGAGAAACTGAATTC |
| | (SEQ ID NO: 4) |
| *Mus musculus* | MVVFNGLLKIKICEAVSLKPTAWSLRHAVGPRPQTFLLDPYIALNVDDSRIGQT |
| protein kinase | ATKQKTNSPAWHDEFVTDVCNGRKIELAVFHDAPIGYDDFVANCTIQFEELLQN |
| C, epsilon | GSRHFEDWIDLEPEGKVYVIIDLSGSSGEAPKDNEERVFRERMRPRKRQGAVRR |

TABLE 1-continued

PKC epsilon nucleotide and amino acid sequences

| Name; GenBank ® Acc. No. | Sequence |
|---|---|
| amino acid | RVHQVNGHKFMATYLRQPTYCSHCRDFIWGVIGKQGYQCQVCTCVVHKRCHELI |
| sequence; | ITKCAGLKKQETPDEVGSQRFSVNMPHKFGIHNYKVPTFCDHCGSLLWGLLRQG |
| NP_035234.1 | LQCKVCKMNVHRRCETNVAPNCGVDARGIAKVLADLGVTPDKITNSGQRRKKLA |
| GI:6755084 | AGAESPQPASGNSPSEDDRSKSAPTSPCDQELKELENNIRKALSFDNRGEEHRA |
| | SSATDGQLASPGENGEVRPGQAKRLGLDEFNFIKVLGKGSFGKVMLAELKGKDE |
| | VYAVKVLKKDVILQDDDVDCTMTEKRILALARKHPYLTQLYCCFQTKDRLFFVM |
| | EYVNGGDLMFQIQRSRKFDEPRSRFYAAEVTSALMFLHQHGVIYRDLKLDNILL |
| | DAEGHCKLADFGMCKEGIMNGVTTTTFCGTPDYIAPEILQELEYGPSVDWWALG |
| | VLMYEMMAGQPPFEADNEDDLFESILHDDVLYPVWLSKEAVSILKAFMTKNPHK |
| | RLGCVAAQNGEDAIKQHPFFKEIDWVLLEQKKIKPPFKPRIKTKRDVNNFDQDF |
| | TREEPILTLVDEAIIKQINQEEFKGFSYFGEDLMP |
| | (SEQ ID NO: 5) |
| *Rattus* | GAATTCCGGAATCCGGCGAGGAAATACATGCACTCGCTGAGAATCGCCGGCGCC |
| *norvegicus* | AGGACGCAGCGCCACAAGGTGTAGCGAGTGAGTGGGGTGGGGCAAGAGGGGACC |
| protein kinase | CAGGAGTCCCCCCAGGCTCCCAGCGCGCCTGCTCCTGCTCTTCAATCCTGCCCT |
| C, epsilon | CGGGGCGGACGGAGTGACCCCCGCCCCGACCATGGTAGTGTTCAATGGCCTTCT |
| nucleotide | TAAGATCAAAATCTGCGAGGCCGTGAGCTTGAAGCCCACAGCCTGGTCGCTGCG |
| sequence; | CCATGCGGTGGGACCCCGGCCCCAGACGTTCCTTCTGGACCCCTACATTGCCCT |
| NM_017171.1 | TAACGTGGACGACTCGCGCATCGGCCAAACAGCCACCAAGCAGAAGACCAACAG |
| GI:39930372 | TCCGGCCTGGCACGATGAGTTCGTCACTGATGTGTGCAATGGGCGCAAGATCGA |
| | GCTGGCTGTCTTTCACGATGCTCCTATCGGCTACGACGACTTCGTGGCCAACTG |
| | CACCATCCAGTTCGAGGAGCTGCTGCAGAATGGGAGCCGTCACTTCGAGGACTG |
| | GATTGATCTGGAGCCAGAAGGAAAAGTCTACGTGATCATCGATCTCTCGGGATC |
| | ATCGGGCGAAGCCCCTAAAGACAATGAAGAACGAGTGTTTAGGGAGCGGATGCG |
| | GCCAAGGAAGCGCCAAGGGGCTGTCAGGCGCAGGGTCCACCAGGTCAATGGCCA |
| | CAAGTTCATGGCCACCTACTTGCGGCAGCCCACCTACTGCTCCCACTGTAGGGA |
| | TTTCATCTGGGGTGTCATAGGAAAACAGGGATATCAATGTCAAGTTTGTACCTG |
| | CGTCGTCCACAAACGATGCCATGAGCTCATTATTACGAAGTGCGCTGGGCTAAA |
| | GAAACAGGAAACCCCTGACGAGGTGGGCTCCCAACGCTTCAGCGTCAACATGCC |
| | CCACAAGTTCGGGATCCACAACTACAAGGTCCCCACGTTCTGTGACCACTGTGG |
| | CTCCCTGCTCTGGGGCCTCTTGCGGCAGGGCCTGCAGTGTAAAGTCTGCAAAAT |
| | GAATGTTCACCGTCGATGCGAGACCAACGTGGCTCCCAATTGTGGGGTGGACGC |
| | CAGAGGAATTGCCAAGGTGCTGGCCGATCTTGGCGTTACTCCAGACAAAATCAC |
| | CAACAGTGGCCAGAGAAGGAAAAAGCTCGCTGCTGGTGCTGAGTCCCCACAGCC |
| | GGCTTCTGGAAACTCCCCATCAGAAGACGACCGATCCAAGTCAGCGCCCACCTC |
| | CCCTTGTGACCAGGAACTAAAAGAACTTGAAAACAACATCCGGAAGGCCTTGTC |
| | ATTTGACAACCGAGGAGAGGAGCACCGAGCCTCGTCGTCTACTGATGGCCAGCT |
| | GGCAAGCCCTGGCGAGAACGGTGAAGTCCGGCAAGGCCAGGCCAAGCGCTTGGG |
| | CCTGGATGAGTTCAACTTCATCAAGGTGTTAGGCAAAGGCAGCTTTGGCAAGGT |
| | CATGCTGGCCGAGCTCAAGGGTAAGGATGAAGTCTATGCTGTGAAGGTCTTAAA |
| | GAAGGACGTCATCCTGCAGGATGACGACGTGGACTGCACGATGACAGAGAAGAG |
| | GATTTTGGCTCTGGCGCGGAAACACCCTTATCTAACCCAACTCTATTGCTGCTT |
| | CCAGACCAAGGACCGGCTCTTCTTCGTCATGGAATATGTAAACGGTGGAGACCT |
| | CATGTTCCAGATTCAGCGGTCCCGAAAATTCGATGAGCCTCGTTCCGGGTTCTA |
| | TGCTGCCGAGGTCACATCTGCTCTCATGTTTCTCCACCAACATGGAGTGATCTA |
| | CAGGGATTTGAAACTGGACAACATCCTTCTAGATGCAGAAGGTCACTCCAAGCT |
| | GGCTGACTTTGGGATGTGCAAGGAAGGGATTCTGAATGGCGTGACAACTACCAC |
| | CTTCTGTGGGACTCCTGACTACATAGCTCCAGAGATCCTGCAGGAGTTGGAGTA |
| | CGGCCCCTCAGTGGACTGGTGGGCCCTGGGCGTGCTGATGTACGAGATGATGGC |
| | CGGGCAGCCCCCCTTTGAAGCTGACAACGAGGACGACTTGTTTGAATCCATCCT |
| | TCACGATGACGTTCTCTACCCTGTCTGGCTTAGCAAGGAGGCTGTCAGCATCCT |
| | GAAAGCTTTCATGACCAAGAACCCGCACAAGCGCCTGGGCTGCGTGGCAGCACA |
| | GAACGGGGAAGATGCCATCAAGCAACATCCATTCTTCAAGGAGATTGACTGGGT |
| | ACTGCTGGAGCAGAAGAAAATGAAGCCCCCCTTCAAGCCGAGAATTAAAACCAA |
| | GAGAGATGTCAATAACTTTGACCAAGACTTTACCCGGGAAGAGCCAATACTTAC |
| | ACTTGTGGATGAAGCAATCGTGAAGCAGATCAACCAGGAAGAATTCAAAGGCTT |
| | CTCCTACTTTGGTGAAGACCTGATGCCCTGAGAAACTGCTTCACATGGAGTTAG |
| | CTCACTGCAAGGAGGGTGTTGAGACAATCCCGTGTTGCAGAGGCTCAGAATGTC |
| | TCGAACTATTCGTCCTCCCCAGAGCCCCAGTCCCACATCTGCTCTCTTATTTAT |
| | TGCATCCCCTCATCCCAGGCCCTGTCCTTCCCCACCCTCCCAGTGACCAGAAGG |
| | CCCTCTTTGGTCCAGACTCACCAAGATCACAGATTTGAACTGCGTCTGCTCTGT |
| | GTGCAGTGCTAGGTCTGGAGTAGCCGTCCACCCACAACCCTGAAGCAGCCCGGA |
| | ATTC |
| | (SEQ ID NO: 6) |
| *Rattus* | MVVFNGLLKIKICEAVSLKPTAWSLRHAVGPRPQTFLLDPYIALNVDDSRIGQT |
| *norvegicus* | ATKQKTNSPAWHDEFVTDVCNGRKIELAVFHDAPIGYDDFVANCTIQFEELLQN |
| protein kinase | GSRHFEDWIDLEPEGKVYVIIDLSGSSGEAPKDNEERVFRERMRPRKRQGAVRR |
| C, epsilon | RVHQVNGHKFMATYLRQPTYCSHCRDFIWGVIGKQGYQCQVCTCVVHKRCHELI |
| amino acid | ITKCAGLKKQETPDEVGSQRFSVNMPHKFGIHNYKVPTFCDHCGSLLWGLLRQG |
| sequence; | LQCKVCKMNVHRRCETNVAPNCGVDARGIAKVLADLGVTPDKITNSGQRRKKLA |
| NP_058867.1, | AGAESPQPASGNSPSEDDRSKSAPTSPCDQELKELENNIRKALSFDNRGEEHRA |
| GI:39930373 | SSSTDGQLASPGENGEVRQGQAKRLGLDEFNFIKVLGKGSFGKVMLAELKGKDE |

TABLE 1-continued

| PKC epsilon nucleotide and amino acid sequences | |
|---|---|
| Name; GenBank ® Acc. No. | Sequence |
| | VYAVKVLKKDVILQDDDVDCTMTEKRILALARKHPYLTQLYCCFQTKDRLFFVM EYVNGGDLMFQIQRSRKFDEPRSGFYAAEVTSALMFLHQHGVIYRDLKLDNILL DAEGHSKLADFGMCKEGILNGVTTTTFCGTPDYIAPEILQELEYGPSVDWWALG VLMYEMMAGQPPFEADNEDDLFESILHDDVLYPVWLSKEAVSILKAFMTKNPHK RLGCVAAQNGEDAIKQHPFFKEIDWVLLEQKKMKPPFKPRIKTKRDVNNFDQDF TREEPILTLVDEAIVKQINQEEFKGFSYFGEDLMP |

PKC Epsilon (PKCϵ) Polypeptide, Peptide and Small Molecule Inhibitors and Enhancers There are a number of inhibitors and enhancers of PKCϵ that are known in the art and can be used in the methods described herein, including peptide and small molecule inhibitors, and antibodies and antigen-binding fragments thereof.

PKCϵ Polypeptides

The methods described herein can include administering a PKCϵ protein that is at least 85%, e.g., at least 90%, 95%, 97%, 98%, or 99% identical to the human PKCϵ sequence at GenBank Acc. No. NP_005391.1 The PKCϵ proteins suitable for use in the methods described herein can phosphorylate the same substrates as the native PKCϵ.

Inhibitory Peptides and Small Molecules

A number of peptide and small molecule inhibitors of PKCϵ are known in the art. For example, U.S. Pat. No. 5,783,405 describes a number of peptides that inhibit PKC isozymes. Of these, the ϵV1-1, ϵV1-2, ϵV1-3, ϵV1-4, ϵV1-5 and ϵV1-6 peptides are selective for PKCϵ and are preferred peptide inhibitors. Peptide ϵV1-2 is a particularly preferred inhibitory peptide; its amino acid sequence is EAVSLKPT (SEQ ID NO:7; available from Santa Cruz Biotechnology). The sequence of the ϵV1-1 peptide is NGLLKIK (SEQ ID NO:8). The sequence of the ϵV1-3 peptide is LAVFHDAPIGY (SEQ ID NO:9). The sequence of the ϵV1-4 peptide is DDFVANCTI (SEQ ID NO:10). The sequence of the ϵV1-5 peptide is WIDLEPEGRV (SEQ ID NO:11). The sequence of the ϵV1-6 peptide is HAVGPRPQTF (SEQ ID NO:12).

Small molecule inhibitors of PKC are described in U.S. Pat. Nos. 5,141,957, 5,204,370, 5,216,014, 5,270,310, 5,292,737, 5,344,841, 5,360,818, and 5,432,198. These molecules belong to the following classes: N,N'-Bis-(sulfonamido)-2-amino-4-iminonaphthalen-1-ones; N,N'-Bis-(amido)-2-amino-4-iminonaphthalen-1-ones; vicinal-substituted carbocyclics; 1,3-dioxane derivatives; 1,4-Bis-(amino-hydroxyalkylamino)-anthraquinones; furo-coumarinsulfonamides; Bis-(hydroxyalkylamino)-anthraquinones; and N-aminoalkyl amides. Due to their relative ease of administration (for instance, transdermal delivery or ingestion are often feasible for small molecules), small molecule inhibitors of PKCϵ are preferred in some embodiments.

PKCϵ Antibodies

The methods described herein can include the administration of an antibody or antigen binding fragment thereof that is specifically reactive with PKCϵ (i.e., does not substantially bind any other isoform of PKC). An antibody can be an antibody or a fragment thereof, e.g., an antigen binding portion thereof. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "antigen-binding fragment" of an antibody (or simply "antibody portion," or "fragment"), as used herein, refers to one or more fragments of a full-length antibody that retain the ability to specifically bind to an antigen (e.g., a polypeptide encoded by a nucleic acid of Group I or II). Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate nucleic acids, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

Anti-protein/anti-peptide antisera or monoclonal antibodies can be made as described herein by using standard protocols (See, for example, *Antibodies: A Laboratory Manual*, ed. by Harlow and Lane (Cold Spring Harbor Press: 1988)).

PKCϵ, or a portion or fragment thereof, can be used as an immunogen to generate antibodies that bind the component using standard techniques for polyclonal and monoclonal antibody preparation. The full-length component protein can be used or, alternatively, antigenic peptide fragments of the component can be used as immunogens.

Typically, a peptide is used to prepare antibodies by immunizing a suitable subject (e.g., rabbit, goat, mouse or other mammal) with the immunogen. An appropriate immunogenic preparation can contain, for example, a recombinant or chemically synthesized PKCϵ polypeptide or antigenic fragment thereof. See, e.g., U.S. Pat. No. 5,460,959; and co-pending U.S. applications U.S. Ser. Nos. 08/334,797; 08/231,439; 08/334,455; and 08/928,881, which are hereby expressly incorporated by, reference in their entirety. The nucleotide and amino acid sequences of PKCϵ are known as described herein. The preparation can further include an adjuvant, such as Freund's complete or incomplete adjuvant, or similar immunostimulatory agent. Immunization of a suitable subject with an immunogenic component or fragment preparation induces a polyclonal antibody response.

Additionally, antibodies produced by genetic engineering methods, such as chimeric and humanized monoclonal antibodies, comprising both human and non-human portions, which can be made using standard recombinant DNA techniques, can be used.

Such chimeric and humanized monoclonal antibodies can be produced by genetic engineering using standard DNA techniques known in the art, for example using methods described in Robinson et al., International Application No. PCT/US86/02269; Akira, et al., European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041-1043, 1988; Liu et al., PNAS 84:3439-3443, 1987; Liu et al., J. Immunol. 139:3521-3526, 1987; Sun et al. PNAS 84:214-218, 1987; Nishimura et al., Canc. Res. 47:999-1005, 1987; Wood et al., Nature 314:446-449, 1985; and Shaw et al., J. Natl. Cancer Inst. 80:1553-1559, 1988); Morrison, S. L., Science 229:1202-1207, 1985; Oi et al., BioTechniques 4:214, 1986; Winter U.S. Pat. No. 5,225,539; Jones et al., Nature 321:552-525, 1986; Verhoeyan et al., Science 239:1534, 1988; and Beidler et al., J. Immunol. 141: 4053-4060, 1988.

In addition, a human monoclonal antibody directed against PKCϵ can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. Pct publication WO 94/04667; Ditullio et al. PCT publication WO 95/17085; Lonberg, N. et al. (1994) Nature 368: 856-859; Green, L. L. et al. (1994) Nature Genet. 7:13-21; Morrison, S. L. et al. (1994) Proc. Natl. Acad. Sci. USA 81:6851-6855; Bruggeman et al. (1993) Year Immunol 7:33-40; Choi et al. (1993) Nature Genet. 4:117-123; Tuaillon et al. (1993) PNAS 90:3720-3724; Bruggeman et al. (1991) Eur J Immunol 21:1323-1326); Duchosal et al. PCT publication WO 93/05796; U.S. Pat. No. 5,411,749; McCune et al. (1988) Science 241:1632-1639), Kamel-Reid et al. (1988) Science 242:1706; Spanopoulou (1994) Genes & Development 8:1030-1042; Shinkai et al. (1992) Cell 68:855-868). A human antibody-transgenic mouse or an immune deficient mouse engrafted with human antibody-producing cells or tissue can be immunized with PKCϵ or an antigenic peptide thereof, and splenocytes from these immunized mice can then be used to create hybridomas. Methods of hybridoma production are well known.

Human monoclonal antibodies can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) J. Mol. Biol. 222:581-597; and Griffths et al. (1993) EMBO J 12:725-734. In addition, a combinatorial library of antibody variable regions can be generated by mutating a known human antibody. For example, a variable region of a human antibody known to bind a PKC, e.g., PKCβ, or Rb, can be mutated, by for example using randomly altered mutagenized oligonucleotides, to generate a library of mutated variable regions which can then be screened to bind to PKC, e.g., PKCβ, or Rb. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) Proc. Nat'l Acad. Sci. USA 89:4457-4461.

The immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) supra; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982. Once displayed on the surface of a display package (e.g., filamentous phage), the antibody library is screened to identify and isolate packages that express an antibody that binds PKCϵ. In a preferred embodiment, the primary screening of the library involves panning with an immobilized PKCε as described herein and display packages expressing antibodies that bind immobilized proteins described herein are selected.

A number of PKCε isoform specific antibodies are known in the art, including antibodies that are commercially available from BD Biosciences Pharmingen; Assay Designs, Inc.; GeneTex; Novus Biologicals; Spring Bioscience; and Upstate/Millipore.

PKCε Inhibitory Nucleic Acids

Inhibitory nucleic acids that reduce expression of PKCε can also be used. For example, small interfering RNAs (siRNAs), antisense, morpholino oligos, and ribozymes can all be used. Useful inhibitory nucleic acids include those that reduce the expression of PKCε by more than 10%. 20%, 30%, 40%, 50%, 60%, 70%, or 80% compared to cells which have not been incubated with the inhibitory nucleic acid.

Accordingly, the invention includes methods that include administering inhibitory nucleic acid molecules that are targeted to PKCε, e.g., antisense, siRNA, ribozymes, peptide nucleic acids, and aptamers.

PKCε siRNA Molecules

RNAi is a process whereby double-stranded RNA (dsRNA, also referred to herein as si RNAs or ds siRNAs, for double-stranded small interfering RNAs) induces the sequence-specific degradation of homologous mRNA in animals and plant cells (Hutvagner and Zamore, Curr. Opin. Genet. Dev.: 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, increase nuclease resistance, as well as engineered RNAi precursors. Various siRNA modifications are described in U.S. Pat. Pub. Nos. 20050176667, 20070197460, and references cited therein.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

A number of PKCε siRNAs are known in the art and disclosed herein. For example, PKCε SMARTpool® siRNA reagent is commercially available from Upstate/Millipore (Charlottesville, Va.). See also Park et al., J. Neurosci. 26: 8999-9005 (2006), and Mirandola et al., Blood 107(2):508-513 (2006). Double-strand siRNAs (dsRNA) were designed to target sequences corresponding to nt's 223 to 244, 429 to 450, 942 to 963, and 1158 to 1179 on human PKC mRNA (NM005400). The target sequences were as follows: 5'-AA-GAT CAAAA TCTGC GAGGCC-3' (SEQ ID NO:13), 5'-AAGAT CGAGC TGGCTG TCTTT-3' (SEQ ID NO:14), 5'-AACTA CAAGG TCCCT ACCTTC-3' (SEQ ID NO:15), and 5'-AAAAA GCTCA TTGCT GGTGCC-3' (SEQ ID NO:16).

PKCε Antisense

An "antisense" nucleic acid can include a nucleotide sequence that is complementary to a "sense" nucleic acid encoding a protein, e.g., complementary to the coding strand of a double-stranded cDNA molecule or complementary to a PKCε mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region (e.g., promoters and/or enhancers) to form triple helical structures that prevent transcription of the Spt5 gene in target cells. See generally, Helene, C. *Anticancer Drug Des.* 6:569-84 (1991); Helene, C. *Ann. N.Y. Acad. Sci.* 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

A number of PKCε antisense molecules are known in the art, see, e.g., U.S. Pat. No. 6,537,973.

PKCε Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a cDNA described herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-1418 (1993).

PKCε Aptamers

Aptamers are short oligonucleotide sequences which can specifically bind specific proteins. It has been demonstrated that different aptameric sequences can bind specifically to different proteins, for example, the sequence GGNNGG (SEQ ID NO:29) where N=guanosine (G), cytosine (C), adenosine (A) or thymidine (T) binds specifically to thrombin (Bock et al (1992) Nature 355: 564 566 and U.S. Pat. No. 5,582,981 (1996) Toole et al). Methods for selection and preparation of such RNA aptamers are known in the art (see, e.g., Famulok, Curr. Opin. Struct. Biol. 9:324 (1999); Herman and Patel, J. Science 287:820-825 (2000)); Kelly et al., J. Mol. Biol. 256:417 (1996); and Feigon et al., Chem. Biol. 3: 611 (1996)).

Methods of Treatment

The methods described herein can be used to modulate, e.g., increase or decrease, angiogenesis as needed in a subject.

For example, the methods described herein can include inhibiting PKCε activity or decreasing levels of PKCε mRNA or protein, and can be used to decrease angiogenesis in a subject who has a condition associated with abnormally high levels of angiogenesis, e.g., retinal neovascularization (e.g., oxygen-induced retinopathy-of-prematurity, oxygen-induced retinopathy, or diabetic retinopathy), or a solid tumor. Retinal neovascularization is a major cause of blindness and requires the activities of several signaling pathways and multiple cytokines As described herein, activation of PKCε enhances NO synthesis and thus the angiogenic process, and is involved in the signaling of vascular endothelial growth factor (VEGF). The potential functional consequences of PKCε-activation could include increased VEGF-induced endothelial cell proliferation.

Alternatively, the methods can include enhancing PKCε activity, or increasing levels of PKCε mRNA or protein, and can be used to increase angiogenesis in a subject who has a condition associated with undesirably low levels of angiogenesis, e.g., an ischemic limb (such as in a diabetic subject) or the cardiac tissue of a subject with coronary artery disease. An organ that is intended to be transplanted can also be treated using a method described herein, to increase vascularisation of the tissues after transplant.

Methods of Administration

PKCε inhibitors can be administered hourly, several times per day, daily or as often as needed, up to and including continuous administration via an infusion pump or other implantable device. Preferably, the administration interval will be in the range of 8 to 24 hours. The severity of the condition can and should be taken into account when determining appropriate intervals for PKCε inhibitor treatments. PKCε inhibitor treatments can continue over the course of several days, one month, several months, one year, several years or the duration of the patient's lifetime. Alternatively, PKCε inhibitors can be administered on a one-time only basis. PKCε inhibitors should be administered at levels sufficient to modulate angiogenesis in the body of the patient.

Inhibitor dosage will vary according to many parameters, including the nature of the inhibitor and the mode of administration. For example, for the εPKC-v1 peptide, a intracellular concentration of about 150 μg/ml inhibited PKCε translocation and downstream effects of PKCε activation (see, e.g., U.S. Pat. No. 5,783,405). Daily dosages in the range of about 1 μg/kg-100 mg/kg of body weight, e.g., about 1 μg/kg-1 mg/kg, e.g., about 10 μg/kg-1 mg/kg are contemplated for PKC inhibitors that are N,N'-Bis-(sulfonamido)-2-amino-4-iminonaphthalen-1-ones or N,N'-Bis-(amido)-2- amino-4-iminonaphthalen-1-ones. Daily dosages in the range of about 1 μg/kg-100 mg/kg of body weight, e.g., about 1 μg/kg-40 mg/kg, e.g., about 10 μg/kg-20 mg/kg are contemplated for PKC inhibitors that are vicinal-substituted carbocyclics. Daily dosages in the range of about 5-400 mg/kg of body weight, e.g., about 10-200 mg/kg, e.g., about 10-50 mg/kg are contemplated for PKC inhibitors that are 1,4-Bis-(amino-hydroxyalkylamino)-anthraquinones, Bis-(hydroxyalkylamino)-anthraquinones, or N-aminoalkyl amides. Daily dosages in the range of about 0.1-40 mg/kg of body weight, e.g., about 1-20 mg/kg, are contemplated for PKC inhibitors that are 1,3-dioxane derivatives. Daily dosages in the range of about 1-100 mg/kg of body weight are contemplated for PKC inhibitors that are furo-coumarinsulfonamides.

In the methods described herein, PKCε inhibitors or enhancers can be locally administered in or near the site where modulation of angiogenesis is desired. Such local administration can be, e.g., topical or by intradermal or subcutaneous injection. Systemic administration of a PKCε inhibitor or enhancer represents another embodiment of the invention. Oral and intravenous injection are preferred types of systemic administration. Local administration of PKCε inhibitors or enhancers is more preferable than systemic administration because local administration should effectively modulate angiogenesis with minimal deleterious side effects on PKCε activity in distant locations. The methods described herein are useful for treating mammals in general and humans in particular.

A preferred embodiment of the present invention is the administration of a pharmaceutically acceptable formulation of an inhibitor or enhancer of PKCε. A "pharmaceutically acceptable formulation" is one that is suitable for administering the PKCε inhibitor or enhancer in a manner that gives the desired results and does not also produce adverse side effects sufficient to convince a physician that the potential harm to a patient is greater than the potential benefit to that patient. The basic ingredient for an injectable formulation is a water vehicle. The water used will be of a purity meeting USP standards for sterile water for injection. Aqueous vehicles that are useful include sodium chloride (NaCl) solution, Ringer's solution, NaCl/dextrose solution, and the like. Water-miscible vehicles are also useful to effect full solubility of the PKCε inhibitor. Antimicrobial agents, buffers and antioxidants are useful, depending on the need.

In preparing PKCε inhibitor or enhancer compositions for this invention, one can follow the standard recommendations of well known pharmaceutical sources such as Remington: The Science and Practice of Pharmacy, 19th ed., (Mack Publishing, 1995). In general, the pharmaceutical composition of this invention is powder- or aqueous-based with added excipients that aid in the solubility of the PKCε inhibitor, the isotonicity of the composition, the chemical stability and the deterrence of microorganism growth. For oral administration, it is preferable to include substances that protect the PKCε inhibitor from degradation by digestive agents.

Administration of PKCε Polypeptide, Peptide and Small Molecule Inhibitors or Enhancers Because PKCε is an intracellular protein, the methods of treatment described herein will generally involve administration of pharmaceutically acceptable inhibitor or enhancer formulations capable of permeating the plasma membrane. Small, apolar molecules are often membrane permeable. The membrane permeability of other molecules can be enhanced by a variety of methods known to those of skill in the art, including dissolving them in hypotonic solutions, coupling them to transport proteins, and packaging them in micelles. Alternatively or in addition, antibodies, peptides and other compounds can be rendered membrane-permeant by the inclusion of a cell-penetrating peptide sequence that facilitates delivery of the peptide to the intracellular space, e.g., HIV-derived TAT peptide, penetratins, transportans, or hCT derived cell-penetrating peptides, see, e.g., Caron et al., (2001) Mol. Ther. 3(3):310-8; Langel, Cell-Penetrating Peptides Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49. Thus, the methods described herein can include the administration of a fusion protein comprising a PKCε polypeptide or active fragment thereof, or an antibody or antigen-binding fragment thereof, and a cell-penetrating peptide.

Administration of Inhibitory Nucleic Acid Molecules

The inhibitory nucleic acid molecules described herein can be administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, inhibitory nucleic acid molecules can be modified to target selected cells and then administered systemically. For systemic administration, inhibitory nucleic acid molecules can be modified such that they specifically bind to receptors or antigens expressed on a selected cell surface, e.g., by linking the inhibitory nucleic acid nucleic acid molecules to peptides or antibodies that bind to cell surface receptors or antigens. The inhibitory nucleic acid nucleic acid molecules can also be delivered to cells using the vectors described herein. To achieve sufficient intracellular concentrations of the inhibitory nucleic acid molecules, vector constructs in which the inhibitory nucleic acid nucleic acid molecule is placed under the control of a strong promoter can be used. Carriers such as liposomes and others that induce internalization will generally be used.

Gene Therapy

The methods described herein in which an increase in PKCε levels is desirable (for increasing angiogenesis, e.g., for the treatment of peripheral and myocardial ischemia, e.g., in tissues such as the limbs of diabetics and cardiac tissue in subjects with coronary artery disease) can include the administration of nucleic acids encoding PKCε. Suitable nucleic acids include the human sequences, available in GenBank at Accession Nos. NM_005400.2 (nucleic acid) and NP_005391.1 (amino acid). At the amino acid level, the deduced human epsilon sequence showed 98 to 99% identity with the mouse and rat sequences. The mouse sequences are Acc. Nos. NM_011104.1 (nucleic acid) and NP_035234.1 (amino acid). The rat sequences are NM_017171.1 (nucleic acid) and NP_058867.1 (amino acid).

The methods can include administering a nucleic acid that encodes a PKCε protein that is at least 85%, e.g., at least 90%, 95%, 97%, 98%, or 99% identical to the human PKCε sequence at GenBank Acc. No. NP_005391.1 The PKCε proteins suitable for use in the methods described herein can phosphorylate the same substrates as the native PKCε.

To determine the percent identity of two nucleic acid sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Such nucleic acids can be incorporated into gene constructs to be used as a part of a gene therapy protocol. Thus, the methods include the administration of expression vectors for in vivo transfection and expression of a PKCϵ as described herein in particular cell types so as to increase the levels of PKCϵ and thereby enhance angiogenesis in the target tissue. Expression constructs of such components may be administered in any biologically effective carrier, e.g. any formulation or composition capable of effectively delivering the component gene to cells, preferably adipose cells, in vivo. Approaches include insertion of the nucleic acid encoding PKCϵ in viral vectors including, but not limited to, recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramicidin S, artificial viral envelopes or other such intracellular carriers, as well as direct injection of the nucleic acid construct or $CaPO_4$ precipitation carried out in vivo. In general, the methods described herein will include the use of catheter mediated infusion of adenoviral particles directly into the affected arteries, e.g., the coronary arteries or arteries feeding an ischemic limb.

In some embodiments, in vivo introduction of nucleic acid into a cell is accomplished by use of a viral vector containing nucleic acid, e.g., a cDNA, encoding PKCϵ. Infection of cells with a viral vector has the advantage that a large proportion of the targeted cells can receive the nucleic acid. Additionally, molecules encoded within the viral vector, e.g., by a PKCϵ cDNA contained in the viral vector, are expressed efficiently in cells which have taken up viral vector nucleic acid.

Retrovirus vectors and adeno-associated virus vectors can be used as a recombinant nucleic acid delivery system for the transfer of exogenous genes in vivo, particularly into humans. These vectors provide efficient delivery of nucleic acids into cells, and the transferred nucleic acids are then generally stably integrated into the chromosomal DNA of the host. The development of specialized cell lines (termed “packaging cells”) which produce only replication-defective retroviruses has increased the utility of retroviruses for therapeutic purposes, and defective retroviruses are characterized for use in nucleic acid transfer for therapeutic purposes (for a review see Miller, Blood 76:271 (1990)). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel et al., (eds.) Greene Publishing Associates, (1989), Sections 9.10-9.14, and other standard laboratory manuals. Examples of suitable retroviruses include pLJ, pZIP, pWE and pEM, all of which are known to those skilled in the art. Examples of suitable packaging virus lines for preparing both ecotropic and amphotropic retroviral systems include *Crip, *Cre, *2 and *Am. Retroviruses have been used to introduce a variety of nucleic acids into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral nucleic acid delivery system useful in the present invention utilizes adenovirus-derived vectors. The genome of an adenovirus can be manipulated such that it encodes and expresses a protein of interest (e.g., PKCϵ) but is inactivated in terms of its ability to replicate in a normal lytic viral life cycle. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other nucleic acid delivery vectors (Berkner et al. cited supra; Haj-Ahmand and Graham (1986) J. Virol. 57:267).

Yet another viral vector system useful for delivery of a nucleic acid encoding PKCϵ is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Immunol. 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

In addition to viral transfer methods, such as those illustrated above, non-viral methods can also be employed to cause expression of PKC, e.g., PKCβ, or Rb in the tissue of a subject. Most nonviral methods of nucleic acid transfer rely on normal mechanisms used by mammalian cells for the uptake and intracellular transport of macromolecules. In preferred embodiments, non-viral nucleic acid delivery systems of the present invention rely on endocytic pathways for the uptake of the nucleic acid encoding PKCϵ by the targeted cell. Exemplary nucleic acid delivery systems of this type include liposomal derived systems, poly-lysine conjugates, and artificial viral envelopes. Other embodiments include plasmid injection systems such as are described in Meuli et al. (2001) J Invest Dermatol. 116(1):131-135; Cohen et al. (2000) Gene Ther 7(22):1896-905; or Tam et al. (2000) Gene Ther 7(21): 1867-74.

In some embodiments, a nucleic acid encoding PKCϵ is entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO91/06309; Japanese patent application 1047381; and European patent publication EP-A-43075).

In clinical settings, the nucleic acid delivery systems for the nucleic acid encoding PKCϵ can be introduced into a patient by any of a number of methods, each of which is familiar in the art. For instance, a pharmaceutical preparation of the nucleic acid delivery system can be introduced systemically, e.g., by intravenous injection, and specific transduction of the protein in the target cells occurs predominantly from specificity of transfection provided by the nucleic acid delivery vehicle, cell-type or tissue-type expression due to the transcriptional regulatory sequences controlling expression of the receptor gene, or a combination thereof. In some embodiments, initial delivery of the nucleic acid encoding PKCϵ is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057).

The pharmaceutical preparation of a nucleic acid construct can consist essentially of the nucleic acid delivery system in an acceptable diluent, or can comprise a slow release matrix in which the nucleic acid delivery vehicle is imbedded. Alternatively, where the complete nucleic acid delivery system can be produced intact from recombinant cells, e.g., as is the case for retroviral vectors, the pharmaceutical preparation can include one or more cells that produce the nucleic acid delivery system.

Methods of delivering a pro-angiogenic factor to an ischemic tissue are known in the art. For example, clinical trials on humans have demonstrated the safety and efficacy of delivering a nucleic acid encoding VEGF to ischemic myocardium and limbs. See, e.g., Yoon et al., Mol. Cell. Biochem. 264:63-74 (2004), describing protocols in which a adenoviral or plasmid vector encoding VEGF is introduced via thoracotomy or percutaneous intramyocardial delivery to the heart in coronary artery disease. In patients with critical limb ischemia, plasmid vector including a VEGF-encoding nucleic acid was delivered to a patent arterial site in an ischemic limb upstream from the occlusion or injected intramuscularly.

Rissanen et al., Advances in Genetics, 52:117-164 (2004) discuss optimal choices vascular growth factor, gene transfer vector, and route of administration in the context of treatment of myocardial and peripheral ischemia with VEGF gene therapy.

Kleiman et al., Am J Cardiol 2003; 92(suppl):9N-17N (2003) reviewed gene therapy methods for increasing angiogenesis using nucleic acids encoding VEGF, FGF, and Hypoxia-inducible factor-1α (HIF1α). Kleiman et al. cite Grines et al., Circulation 105:1291-1297 (2002), which describes a clinical trial in which a single intracoronary infusion through subselective catheters of adenovirus type 5 expressing human FGF-4 resulted in 87% first-pass uptake of the vector by the heart. See also Grines et al., J. Am. Coll. Cardiol. (42)8:1339-47 (2003), further confirmation that gene therapy methods are safe and effective in increasing angiogenesis in the myocardium.

Methods of Screening

Additional inhibitors of PKCϵ useful in the methods described herein can be identified using assays known in the art. Thus, the invention provides methods for identifying compounds, e.g., small organic or inorganic molecules (e.g., those with a molecular weight of less than 1,000 Da), oligopeptides, oligonucleotides, or carbohydrates, capable of specifically modulating (i.e., reducing or increasing) PKCϵ expression levels or activity.

Test Compounds

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules, e.g., as exemplified by Obrecht and Villalgordo, *Solid-Supported Combinatorial and Parallel Synthesis of Small-Molecular-Weight Compound Libraries*, Pergamon-Elsevier Science Limited (1998). Such methods include the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, β-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides.

In some embodiments, test compounds and libraries thereof can be obtained by systematically altering the structure of a first test compound. Taking a small molecule as an example, e.g., a first small molecule is selected that is, e.g., structurally similar to a known natural binding partner of PKCϵ, or has been identified as capable of binding PKCϵ. For example, in one embodiment, a general library of small molecules is screened, e.g., using the methods described herein, to select a fist test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" (e.g., test compounds that demonstrate the ability to modulate levels or activity of PKCϵ) in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in the methods of treating and preventing disorders described herein. Thus, the invention also includes compounds identified as "hits" by a method described herein, and methods for their administration and use in the treatment, prevention, or delay of development or progression of a disease described herein.

Assays for PKCϵ Activity or Levels

Exemplary assays, include, but are not limited to, those that measure PKCϵ mRNA or protein levels, PKCϵ activation, intracellular translocation, binding to intracellular receptors (e.g., RACKs) or catalytic activity of PKCϵ.

As one example, the kinase activity of PKCϵ can be assayed using at least partially purified PKCϵ, e.g., recombinant PKCϵ, in a reconstituted phospholipid environment with radioactive ATP as the phosphate donor and eNOS protein or a short peptide including one or more eNOS phosphorylation sites as the substrate (see, e.g., Kitano et al., Meth. Enzymol. 124:349-352 (1986); Messing et al., J. Biol. Chem. 266: 23428-23432 (1991)). Rapid, highly sensitive chemiluminescent assays that measure protein kinase activity at physiological concentrations and can be automated and/or used in high-throughput screening are also known in the art, see, e.g., Lehel et al., Anal. Biochem. 244:340-346 (1997); other assays are known that use PKC in isolated membranes and a selective peptide substrate that is derived from the MARCKS protein (see, e.g., Chakravarthy et al., Anal. Biochem. 196: 144-150 (1991)).

In some embodiments, the assay includes measuring increases in intracellular concentrations of $Ca^{2+}$ ($[Ca^{2+}]_i$).

Inhibitors that affect the intracellular translocation of PKCϵ can be identified by assays in which the intracellular localization of PKCϵ is determined by fractionation (see, e.g., Messing et al., (1991), supra), immunohistochemistry (U.S. Pat. Nos. 5,783,405 and 6,255,057), or fluorescent imaging, e.g., in live or fixed cells. To identify an inhibitor of PKCϵ, the assays should be performed with PKCϵ.

Methods of evaluating the effect of a compound on PKCϵ mRNA or protein levels are well known in the art, including, e.g., Northern and Western blotting using PKCϵspecific probes and antibodies. See, e.g., *Current Protocols in Molecular Biology* and *Current Protocols in Protein Science*, both from John Wiley & Sons, Inc., for detailed protocols.

In some embodiments, the screening methods described herein can include adding VEGF to a cell and determining whether a PKCϵ-specific modulator can enhance or inhibit an effect of VEGF in the cell, e.g., enhance or inhibit an increase in intracellular concentrations of Ca2+ ([Ca2+]i), phosphorylation of one or more residues of eNOS, and NO production or signalling.

As described in the Examples herein, PKCϵ inhibition results in downregulation of VEGFR2 (also known as KDR). This effect is highly specific to PKCϵ. Thus, screening methods can include assays in which VEGFR2 expression or activity is evaluated. VEGFR2 expression can be evaluated, e.g., using real-time PCR analysis of cultured endothelial cells. In some embodiments, a compound is first identified as a PKCe inhibitor, then tested for its effect on VEGFR2 expression or activity. In other embodiments, a compound identified as an inhibitor of VEGFR2 is analyzed to determine its specificity for PKCϵ.

The selectivity of PKCϵ modulators identified by a method described herein can be determined by comparing the effect of the compound on PKCϵ with its effect on other PKC isozymes; the methods described herein can include performing such a comparison and selecting those compounds that act selectively on PKCϵ (i.e., do not significantly affect levels and/or activity of other PKC isoforms). Selective PKCϵ modulators are advantageous for treating conditions, e.g., because they can cause fewer side effects than modulators that cross react with other PKC isoforms.

PKCϵ modulators can be evaluated in animal models. Agents that enhance PKCϵexpression or activity in vitro can be tested in models suitable for examining the promotion of angiogenesis (e.g., promotion of neovascularization in ischemic tissues, such as ischemic limbs or myocardial tissue). Such models are known in the art. See, e.g., Yoon et al., Mol. Cell. Biochem. 264:63-74 (2004), and references cited therein. See also Rissanen et al., Advances in Genetics, 52:117-164 (2004); Kleiman et al., Am J Cardiol 2003; 92(suppl):9N-17N (2003); Grines et al., Circulation 105: 1291-1297 (2002); and Grines et al., J. Am. Coll. Cardiol. (42)8:1339-47 (2003).

Agents that inhibit PKCϵ expression or activity in vitro can be tested in models suitable for investigating inhibition of angiogenesis (e.g., in solid tumor models, and models for retinopathy). These are known in the art, and are reviewed in Norrby, J. Cell. Mol. Med., 10(3):588-612 (2006)(which also refers to models for examining pro-angiogenic agents).

EXAMPLES

The invention is further described in the following examples, which do not limit the scope of the invention described in the claims.

Materials

GF109203X (GFX), wortmannin, H89, and KN-93 were obtained from Calbiochem (San Diego, Calif.). Ruboxistaurin (LY333531) was a gift from Eli Lilly (Indianapolis, Ind.). VEGF-A165 was obtained from R & D Systems (Minneapolis, Minn.). All other materials were purchased from Sigma (St. Louis, Mo.), except when otherwise specified.

Cell Culture

Bovine aortic endothelial cells (BAEC) were isolated by scraping the luminal side of a calf aorta with a cover glass and transferring the harvested material to a 100 mm cell culture dish. The primary culture and subcultures were grown in Dulbecco's modified Eagle medium (DMEM) with 5.5 mM glucose, 10% (v/v) horse serum, 25 mM HEPES, 100 U/ml penicillin, and 100 μg/ml streptomycin in collagen I-coated dishes (BioCoat, BD BioSciences). Purity of the cultures was validated by the presence of typical "cobblestone" morphology during phase-contrast microscopy (16) and by the ability of cells to take up acetylated LDL (DiI AcLDL, Molecular Probes, Eugene, Oreg.). Cultures used for experiments were plated in 6-well plates (9.5 $cm^2$ wells), except for PKC translocation assays (see below). The cells were serum-starved for 16 hours before stimulation by replacing growth medium with DMEM containing 0.1% (w/v) bovine serum albumin. At the time of stimulation, cultures were typically 3 days old and confluent. GF109203X (GFX) (Calbiochem, San Diego, Calif.), wortmannin (Calbiochem), phorbol-12-myristate-13-acetate (PMA) (Sigma, St. Louis, Mo.), bovine insulin (Sigma), and VEGF-$A_{165}$ (R & D Systems, Minneapolis, Minn.) were added directly to the culture medium when indicated, using an identical volume of solvent as control.

Cell Fractionation

Cytosol and membrane fractions were prepared as described previously (17). For each condition, three 15 cm plates (each 151 $cm^2$) were used. After stimulation, the plates were washed twice in ice-cold PBS and once in a hypertonic lysis buffer (Buffer A) containing Tris (pH 7.5, 20 mM), sucrose (300 mM), EDTA (2 mM), EGTA (0.5 mM), DTT (1 mM), leupeptin (10 μg/ml), and PMSF (1 mM). Each set of 3 plates were then scraped in a combined volume of 3 ml of hypertonic buffer, homogenized in a glass Dounce homogenizer, and centrifuged at 1,000×g for 10 minutes. The supernatant was ultracentrifuged at 100,000×g for 30 minutes, and the ensuing supernatant was taken aside and used as the cytosolic fraction. The pellet was washed once in Buffer B (Buffer A without sucrose), then homogenized in 2.7 ml Buffer B in a glass Dounce homogenizer, and finally lysed by adding 0.3 ml Triton X-100 to a final concentration of 1% (v/v) and rotated for 30 minutes. After ultracentrifugation at 100,000×g for 30 minutes, the supernatant was taken aside and used as the membrane fraction. By using similar volumes for the initial lysis and for the membrane pellet, protein abundance in the cytosol and membrane fraction approximately represent their relative expression in the intact cell. Protein concentration was measured in both fractions with the bicinchoninic acid (BCA) assay, and samples were normalized for protein concentration and assayed by electrophoresis and Western blotting as described below.

siRNA Design and Transfection siRNAs were synthesized as 21-nucleotide oligoribonucleotides with a 19 basepair duplex region and two deoxynucleotide overhangs on the 3'-terminus of each strand. Nucleotide (nt) 424-916 in contig 547130 of the cow whole genome shotgun sequence (gi:53111763) showed 93% homology with human AMPKα1. The target sequence 5'-GCAATTAAACAGCTGGATT-3' (SEQ ID NO:17)(nt 885-903 in contig 547130) was chosen by Invitrogen's BLOCK-iT™ RNAi designer (available on the world wide web at rnaidesigner.invitrogen.com/sirna/). Subsequently, the predicted sequence of bovine AMPKα1 has been published and contains the same sequence (gi:61873865).

Target sequences were chosen by the online tool on the world wide web at dharmacon.com/sirna/Default.aspx (Dharmacon, Lafayette, Colo.), based on an algorithm described previously (Teynolds et al. Nat. Biotechnol., 22(3): 326-330, 2004). The overhangs on the antisense (guide) siRNA strand were complementary to the target sequence, whereas the overhang on the sense siRNA strand was always dTdT. The 5' to 3' sequence of the guide strand of each siRNA were as follows, with deoxynucleotide overhangs in lowercase letters: PKCα, UUAAUUUGAACGUGAAGGAct (SEQ ID NO:18); PKCδ, AUCUUGUCGAUGCAUUUCUtg (SEQ ID NO:19); PKCϵ, UCAAAUGACAAGGCCUUCCgg (SEQ ID NO:20). A second PKCϵ siRNA was used in experiments with results presented in FIG. 12 and had the following guide strand 5' to 3' sequence: TTGCCCAACACCTTGATGAag (SEQ ID NO:21). The two PKCϵ siRNAs thus targeted different regions in PKCϵ mRNA, nt 1224-1242 and 1360-1382, respectively (Accession NM_001111120).

As a negative control, an siRNA was designed to target enhanced green fluorescent protein (eGFP), which is absent in the cow genome. The eGFP target sequence was 5'-GCAGCACGACUUCUUCAAG-3' (SEQ ID NO:22)(nt 852-870 in gi:1377914), which previously has been shown to efficiently knock-down eGFP (18). Selecting a negative control by this strategy has been employed and recommended by Tuschl's group (19) and has the advantage, compared to an siRNA with a scrambled sequence, that the control siRNA is known to induce the RNA interference machinery. For each of these siRNAs, non-target sequence homology contained 14 identical nucleotides or less when the cow genome was searched with BLAST.

Double-stranded siRNA was synthesized by Ambion (Austin, Tex.) with symmetric 3' dTdT-overhangs (19). Bovine aortic endothelial cells (BAEC) were cultured as described above; briefly, the BAEC were isolated by scraping the luminal side of a calf aorta with a cover glass and transferring the harvested material to a 10 cm cell culture dish. Antibiotics were omitted in the DMEM. Twenty-four hours after plating, when the culture was half-confluent, BAEC were transfected with siRNA (final concentration 100 nM) using Lipofectamine-2000 (Invitrogen, Carlsbad, Calif.) (final concentration 0.125% v/v). The medium was changed after 5 hours. Cultures were used for experiments 72 hours after transfection, preceded by 24 hours of serum-starvation in DMEM with 0.1% (w/v) BSA.

Western Blotting and Immunoprecipitation

Cultures were washed twice with ice-cold PBS and lysed in a buffer containing Tris (20 mM, pH 7.5), Triton X-100 (1% v/v), sodium pyrophosphate (2.5 mM); NaF (10 mM), NaCl (140 mM), EDTA (1 mM), EGTA (1 mM), β-glycerophosphate (1 mM), $Na_3VO_4$ (1 mM), leupeptin (1 μg/ml=2 μM), aprotinin (1 μg/ml=15 pM), and phenylmethylsulfonylfluoride (1 mM). Protein concentration was measured by the Bradford method and samples reduced in modified Laemmli buffer (Invitrogen) and heated at 70° C. for 10 minutes. Equal sample volume and protein mass and reduced samples were separated on precast minigels (NuPAGE tris-acetate gels, Invitrogen) and electrotransferred to nitrocellulose.

For VEGFR2 and VEGFR1 immunoprecipitation, approximately 1 mg of protein was immunoprecipitated with 20 μg polyclonal antibody (Santa Cruz Biotechnology, Santa Cruz, Calif.) and washed 3 times with lysis buffer. Whole cell lysate or immunoprecipitates were reduced by addition of modified Laemmli buffer (Invitrogen) and heating to 70° C. for 10 minutes. Samples were then separated on precast minigels (NuPAGE tris-acetate gels, Invitrogen) and electrotransferred to a nitrocellulose membrane. Primary antibodies for Western blotting were specific for PKCα, β1, β2, δ, θ, and ϵ (Santa Cruz), glyceraldehyde-3-phosphate dehydrogenase (GAPDH) (Abcam, Cambridge, Mass.), platelet/endothelial cell adhesion molecule (PECAM-1), phosphorylated and phospho-unspecific forms of Akt, eNOS (Cell Signaling Technology, Beverly, Mass.), phospho-tyrosine (Upstate, Lake Placid, N.Y.), VEGFR2 (Upstate catalogue number 05-554), and VEGFR1 (Santa Cruz catalogue number sc-316 and sc-9029, Upstate catalogue number 05-696).

Primary antibody targets were visualized by incubation with horseradish peroxidase-linked secondary antibodies, enhanced chemiluminescence (Amersham Biosciences (currently GE Healthcare), Piscataway, N.J.), and exposure to X-ray film (Kodak, New Haven, Conn.). The film was scanned and signal intensity of protein bands quantitated with ImageQuant software (version 5.1, Molecular Dynamics/Amersham Biosciences/GE Healthcare, Piscataway, N.J.). The intensity of phospho-specific immunoblot was normalized to the intensity of the unstimulated condition and of the nonphospho-specific protein.

Intracellular NO Synthase Activity Assay

NO synthase activity was assayed in intact BAEC culture as previously described (20) with modifications. One hour before the assay, the medium was exchanged with 0.4 ml DMEM without L-arginine (US Biological, Marblehead, Mass., cat. no. D9800-06), but with BSA 0.1%. Then, 0.1 ml of $^3$H-L-arginine (Perkin Elmer, Wellesley, Mass.) mixed with unlabeled L-arginine was added for 30 minutes, yielding a final L-arginine concentration and specific activity of 100 μM and 100 μCi/ml, respectively. VEGF (final concentration 1 nM) was added for 10 minutes as indicated. Cultures were washed twice in ice-cold PBS containing L-arginine 5 mM and EDTA 5 mM. Cells were then lysed in 1 ml of ice-cold buffer containing Tris (pH 7.5, 20 mM), Triton X-100 (1% v/v), sodium acetate (20 mM, pH 5.5), EDTA (2 mM), and EGTA (2 mM). 100 μl was taken aside for measurement of protein concentration, whereas the remainder of the sample was applied to AG 50W X8 resin, 200-400 mesh (Bio-Rad, Hercules, Calif.) (in columns of 1 ml resin precipitate after conversion to the $Na^+$ form), binding $^3$H-L-arginine to the resin by ion exchange and thus separating it from $^3$H-L-citrulline collected in the flow-through, the radioactivity of which was measured by fluid scintillation.

DNA Synthesis

For measurement of DNA synthesis, cells were trypsin-treated 2 days after transfection with siRNA, and 10,000 cells were added to each well (0.32 $cm^2$) of 96-well plates in serum-free DMEM with 0.1% BSA, with or without VEGF 1 nM. After 16 hours, cells were labeled with 5-bromo-2'-deoxyuridine (BrdU) according to the manufacturer's instructions (Roche Applied Science, Penzberg, Germany). In short, the medium was replaced with medium containing 10 μM BrdU. After an additional 8 hours, cells were fixed and incubated with anti-BrdU antibody conjugated with peroxidase. After washing, a solution of tetramethyl-benzidine was added, and the color reaction quantitated by measuring the difference between the optical density at 370 and 492 nm.

Real-Time PCR

The RNeasy Plus Mini Kit (QIAGEN, Valencia, Calif.) was used to lyse BAEC, remove genomic DNA, and isolate RNA. Reverse transcription of 1 μg RNA was performed with the High-Capacity cDNA Archive Kit (Applied Biosystems, Foster City, Calif.). Real-time TaqMan PCR (Applied Biosystems) was performed using 25 ng cDNA as template and with primers and probe for the target and for 18S ribosomal RNA (Applied Biosystems) in the same reaction volume. Target mRNA normalized to 18S RNA was calculated with the $\Delta\Delta C_T$ method. Primers and probes were designed using the online tool published by Integrated DNA Technologies on the world wide web at scitools.idtdna.com/Scitools/Applications/Primerquest. Their sequences were: VEGFR2 forward primer, 5'-AAC TgT ggT gAT TCC gTg TTT ggg-3' (SEQ ID NO:23); VEGFR2 reverse primer, 5'-TCT ggC TgT CCC Agg AAA TTC TgT-3' (SEQ ID NO:24); VEGFR2 probe (spans exon 4 and 5), 5'-CCT CAA TgT gTC ACT CTg TgC AAg gT-3' (SEQ ID NO:25); VEGFR1 forward primer, 5'-ATg ATg CCA gCA AgT ggg AgT TTg-3' (SEQ ID NO:26); VEGFR1 reverse primer, 5'-ATT TCT TgA TgC CgA ACg CCg ATg-3' (SEQ ID NO:27); VEGFR1 probe (spans exon 3 and 4), 5'-AgA CTT AAA CTg ggC AAg TCA CTC gg-3' (SEQ ID NO:28).

Statistical Analysis Comparisons were made using paired or unpaired t-test, as appropriate, with $p<0.05$ considered statistically significant. In text and graphs, data are presented as the mean±standard error of the mean.

Example 1

PMA, a DAG analogue which activates conventional and novel PKC isoforms (21), inhibits insulin-stimulated IRS-2 associated PI3K activity in BAEC (14). Furthermore, both insulin and VEGF can activate PI3K followed by activation of Akt, which directly phosphorylates eNOS at Ser1779 (4, 12, 22, 23).

BAEC were stimulated with insulin (100 nM, 5 minutes) or VEGF (1 nM, 5 minutes) after pretreatment with PMA (100 nM, 30 minutes) or vehicle as a control (DMSO, 0.2% (v/v)). Akt and eNOS phosphorylation in the BAEC was examined. The data are shown in FIG. 1. In some experiments (FIGS. 1C and 1D), BAEC were also incubated with GFX (1 μM) or vehicle (DMSO 0.2%) 60 minutes before insulin or VEGF stimulation.

Stimulation with insulin (100 nM, 5 minutes) or VEGF (1 nM, 5 minutes) increased phosphorylation of Akt at Ser473 and Thr308 (FIG. 1*a*). Specifically, Akt Ser473 phosphorylation was increased by 3.7±0.7-fold after insulin stimulation and by 2.9±0.8-fold after VEGF stimulation (FIG. 1*a*). To characterize the effect of PKC activation on both insulin- and VEGF-stimulated Akt/eNOS signaling, BAEC were incubated with PMA (100 nM, 30 minutes). Akt Ser473 and Thr308 phosphorylation were greatly decreased after pre-incubation with PMA, both at basal and after either insulin or VEGF stimulation (FIG. 1*a*). Thus, addition of PMA decreased Akt Ser473 phosphorylation by 59±12% in the basal state (p=0.02), and by 81±4% and 79±4% after insulin- and VEGF-stimulation, respectively, to below basal levels.

Figure 1B:
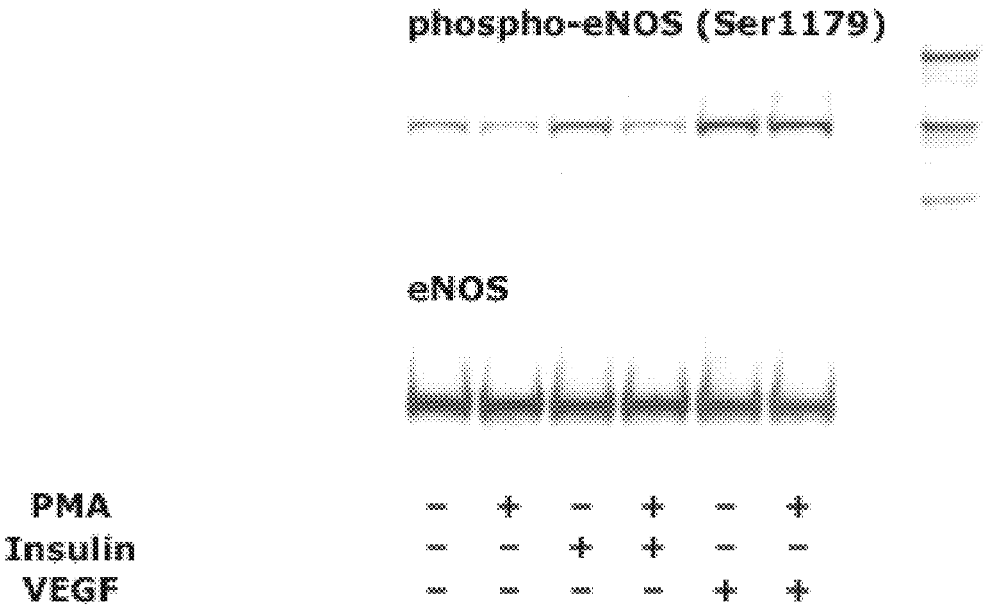
Figure 1B:
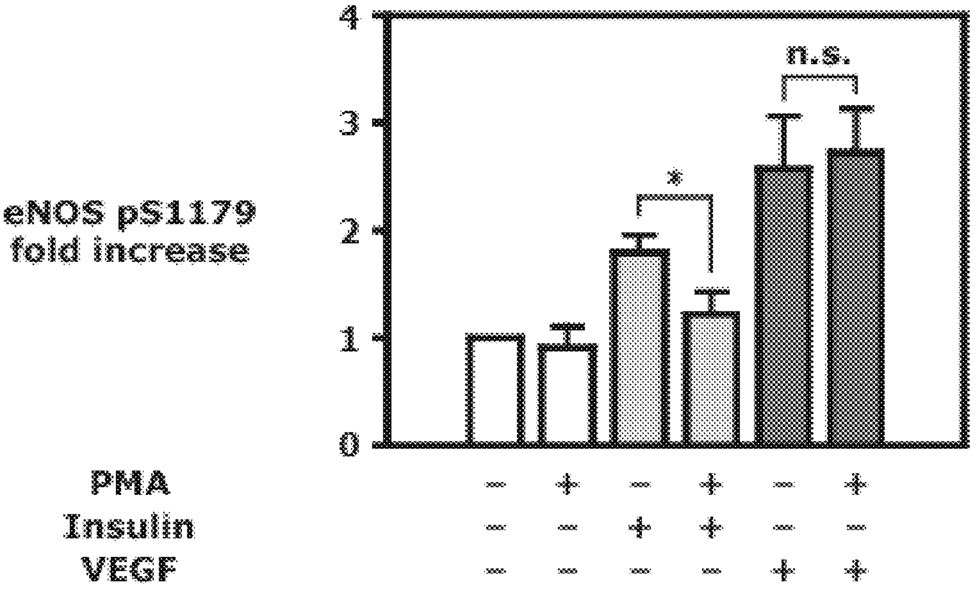
Figure 1C:
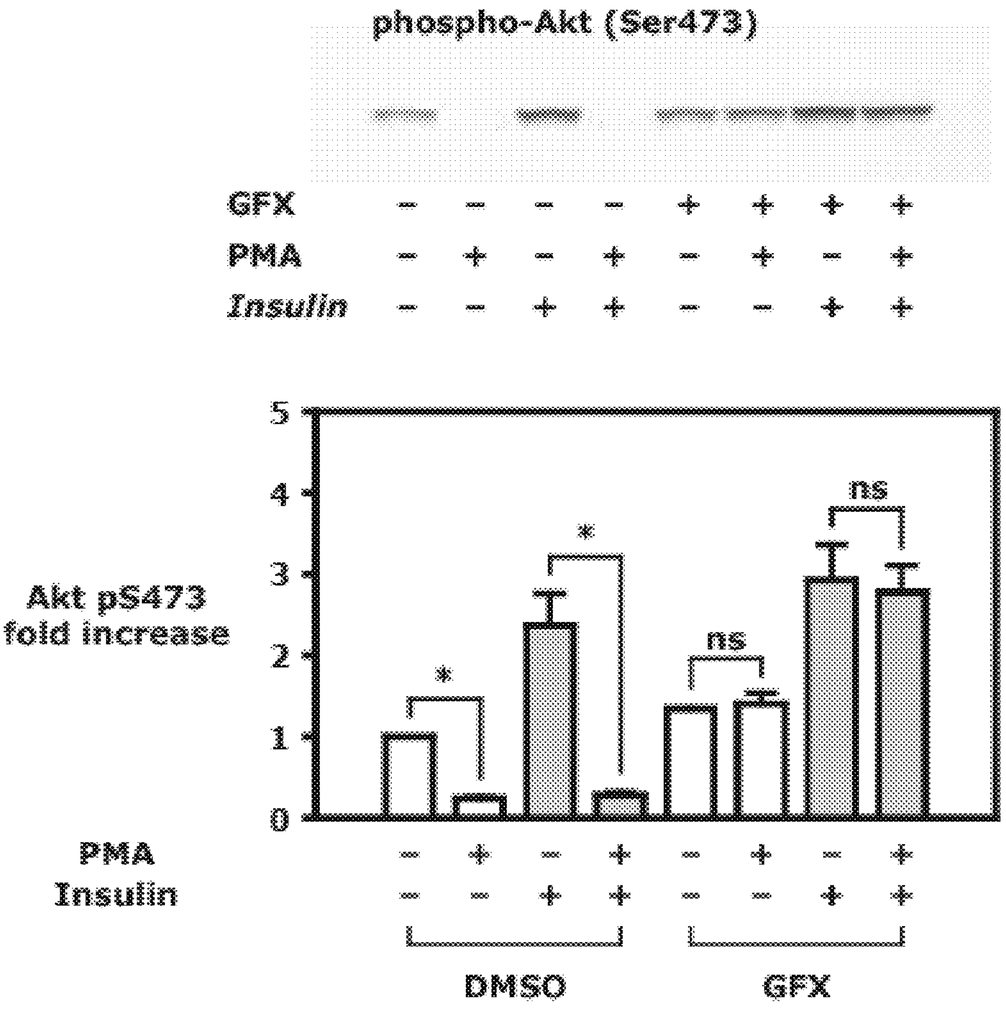

As expected, phosphorylation of eNOS Ser1179 after stimulation with insulin was inhibited in parallel with the decrease in Akt phosphorylation by the addition of PMA. eNOS phosphorylation increased by 1.8±0.2-fold during insulin stimulation, but increased only by 1.2±0.2-fold when insulin was preceded by PMA (FIG. 1*b*, p=0.01). Surprisingly, VEGF-stimulated eNOS Ser1179 phosphorylation was unchanged after pre-incubation with PMA (FIG. 1*b*): eNOS phosphorylation was increased 2.6±0.5-fold during VEGF stimulation and 2.7±0.4-fold when VEGF was preceded by PMA.

Thus, unlike insulin, VEGF was able to increase eNOS Ser1179 phosphorylation even during pronounced inhibition of Akt by PMA.

Figure 1D:
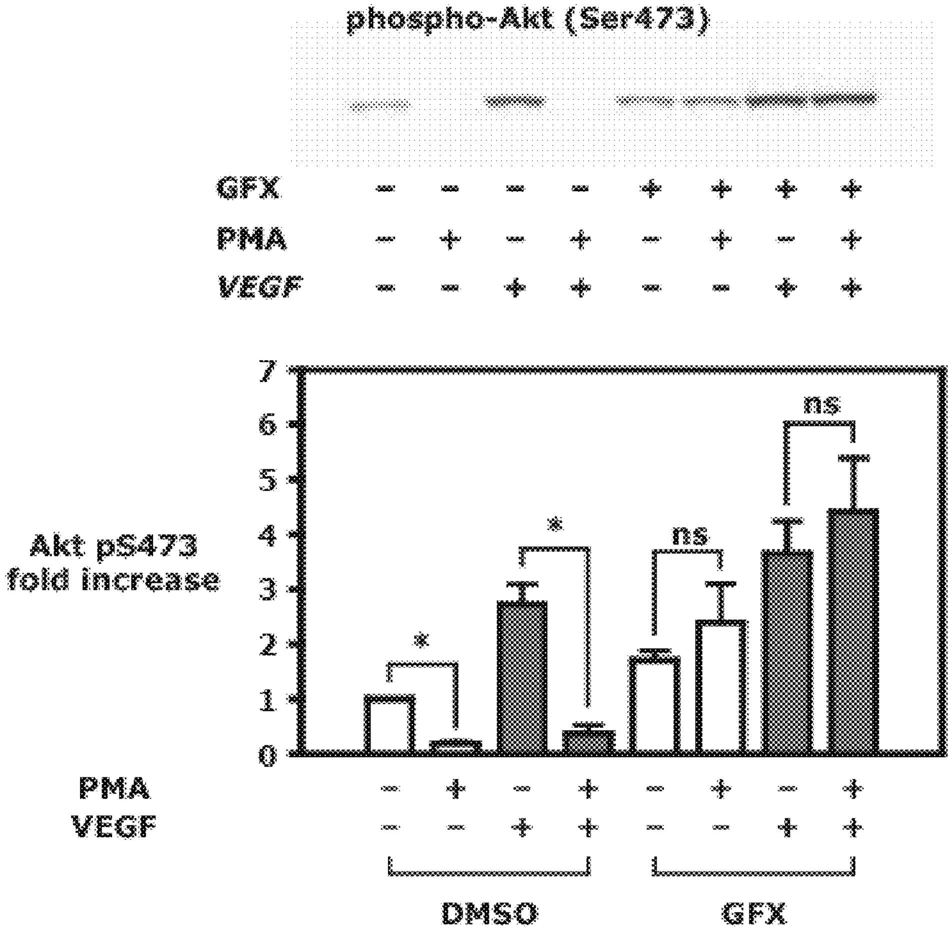

To confirm that the actions of PMA were caused by PKC activation, BAEC were stimulated with PMA after pre-incubation with GFX, a general PKC inhibitor (24) (1 μM, 30 minutes pre-incubation). GFX completely prevented the effects of PMA on Akt and eNOS phosphorylation with or without stimulation with insulin (FIG. 1*c*) or VEGF (FIG. 1*d*).

Example 2

Since inhibition of Akt by PMA likely involves inhibition of PI3K (14), the actions of PMA were compared with wortmannin, an irreversible inhibitor of PI3K. BAEC were stimulated with insulin (100 nM, 5 minutes) or VEGF (1 nM, 5 minutes) after pretreatment with wortmannin (100 nM, 30 minutes before insulin or VEGF stimulation) or vehicle (DMSO 0.2% (v/v)). The data are shown in FIG. 2. In some experiments (FIG. 2C), BAEC were incubated with wortmannin (60 minutes before VEGF stimulation) or DMSO, then with PMA (30 minutes before VEGF stimulation) or DMSO.

Figure 2A:
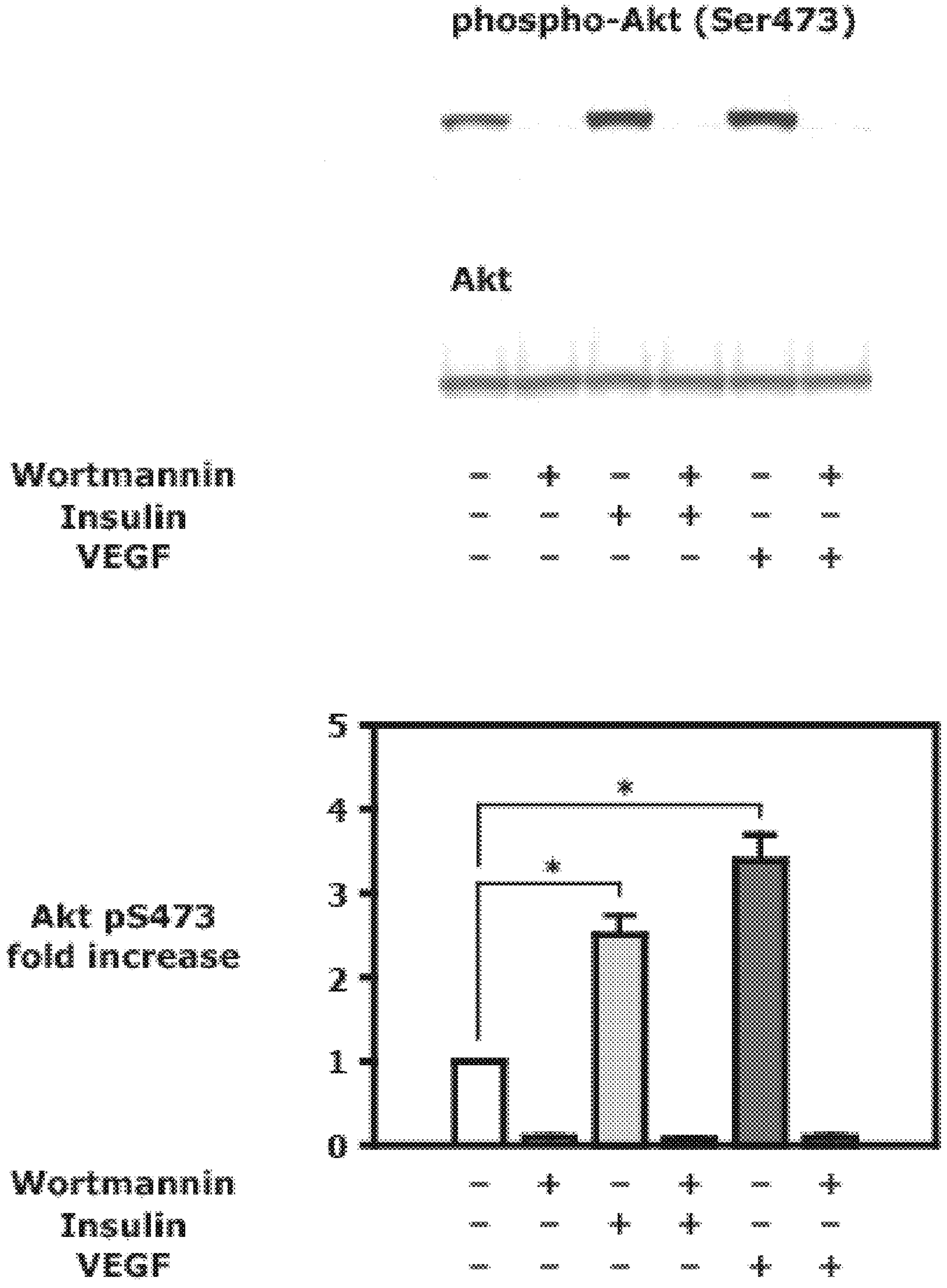
FIGS. 2A-C are sets of immunoblots and bar graphs depicting phosphorylation of Akt Ser473 and of eNOS Ser1179 stimulated by insulin or VEGF during PI3K inhibition and PKC activation. Representative immunoblots are shown above mean data of the phospho-protein normalized to the control condition.
Figure 2B:
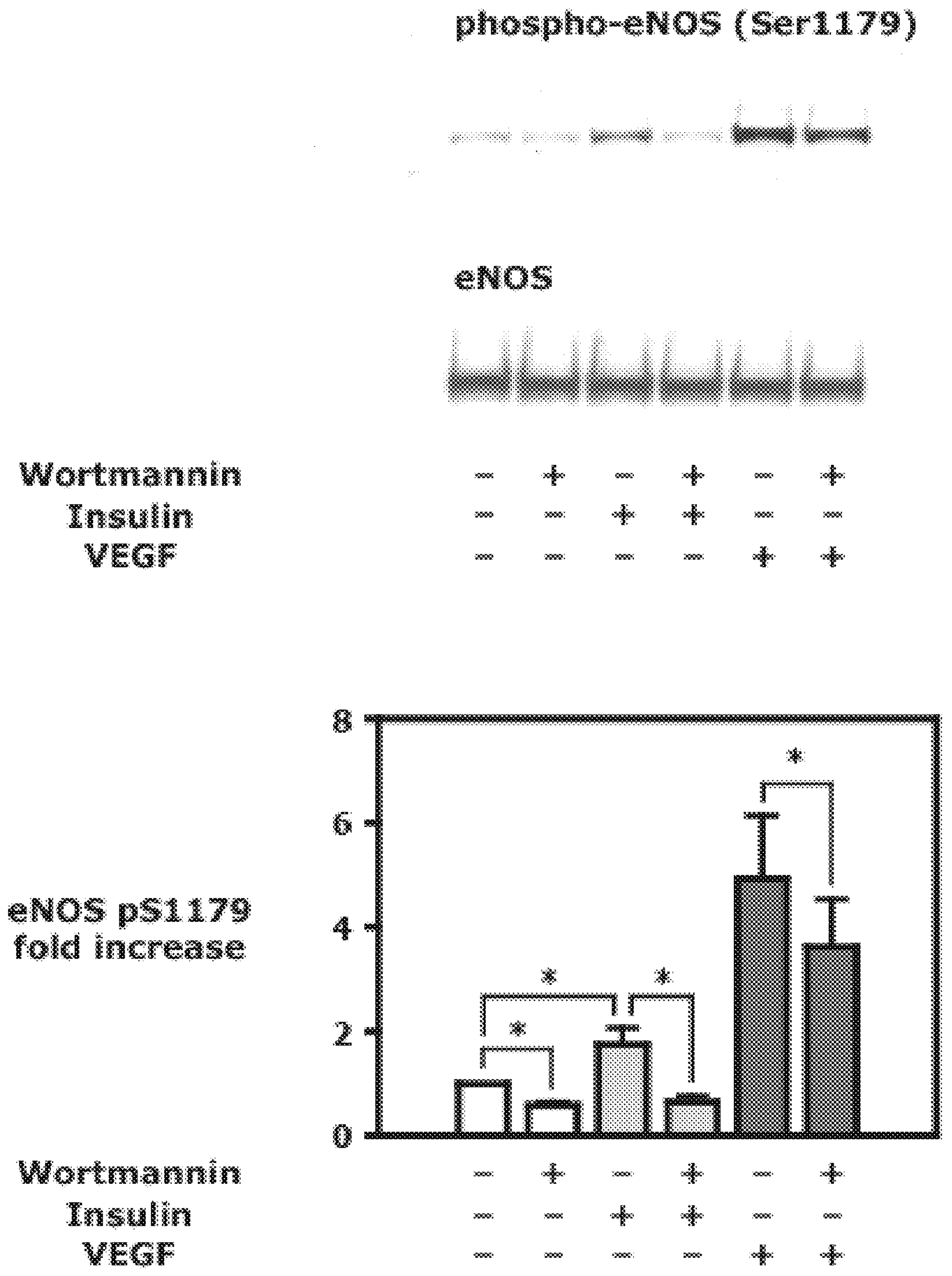
Figure 2C:
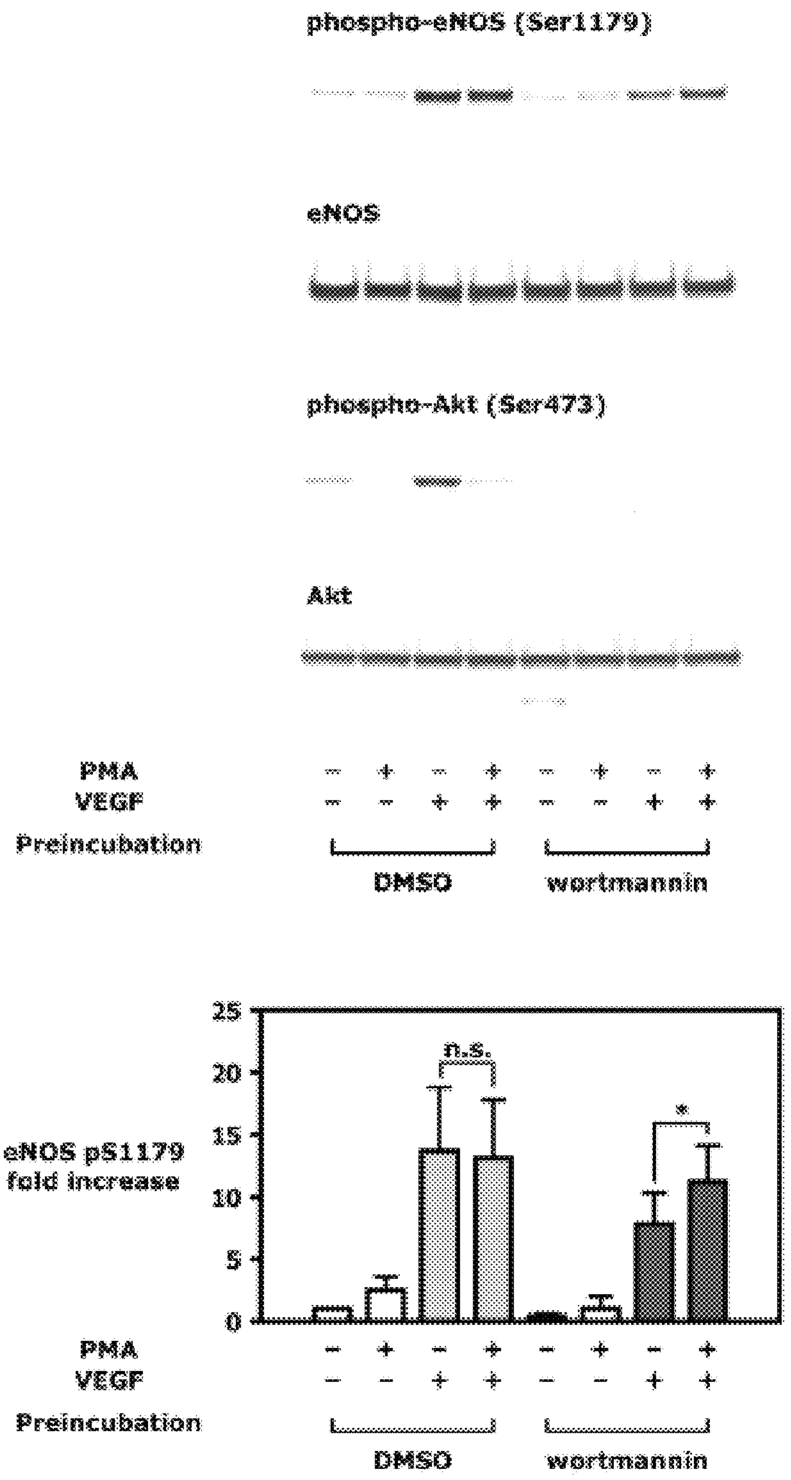

When BAEC were pre-incubated with wortmannin (100 nM, 30 minutes pre-incubation), Akt Ser473 phosphorylation decreased to barely detectable levels in the unstimulated condition as well as after stimulation with either insulin or VEGF (FIG. 2*a*). Furthermore, wortmannin pre-incubation inhibited eNOS Ser1179 phosphorylation after insulin or VEGF stimulation (FIG. 2*b*). Specifically, wortmannin decreased eNOS phosphorylation to 63±1% of basal, completely inhibited insulin-stimulated eNOS phosphorylation to below the basal level, and partly inhibited VEGF-stimulated eNOS phosphorylation (by 30±9%, FIG. 2*b*).

Thus, without additional PKC activation, eNOS Ser1179 phosphorylation is entirely dependent on PI3K when stimulated by insulin, and partly dependent on PI3K when stimulated by VEGF.

Since both insulin- and VEGF-stimulated Akt phosphorylation are potently inhibited by PKC activation with PMA, but only VEGF-stimulated eNOS Ser1179 phosphorylation is maintained in this situation, it is likely that PKC activation can promote eNOS Ser1179 phosphorylation by a pathway independent of PI3K and Akt. To evaluate PI3K-independent pathways, BAEC were pretreated with wortmannin. Pre-incubation with wortmannin caused a partial inhibition of VEGF-stimulated eNOS Ser1179 phosphorylation (FIG. 2*c*), as described above (FIG. 2*b*). Interestingly, in the presence of wortmannin, PMA paradoxically caused a 50±9% increase in VEGF-stimulated eNOS Ser1179 phosphorylation (FIG. 2*c*).

Thus, PKC activation, possibly through different isoforms, can both positively and negatively affect eNOS Ser1179 phosphorylation.

Example 3

It has been reported by various groups that PKCα, β1, β2, δ, θ, ϵ, and ζ are expressed in endothelial cells from different species and in different vascular beds (25, 26). As a DAG analog, PMA activates conventional and novel PKC isoforms (21). Therefore the presence of conventional and novel PKCα, β1, β2, δ, and θ was characterized.

Figure 3:
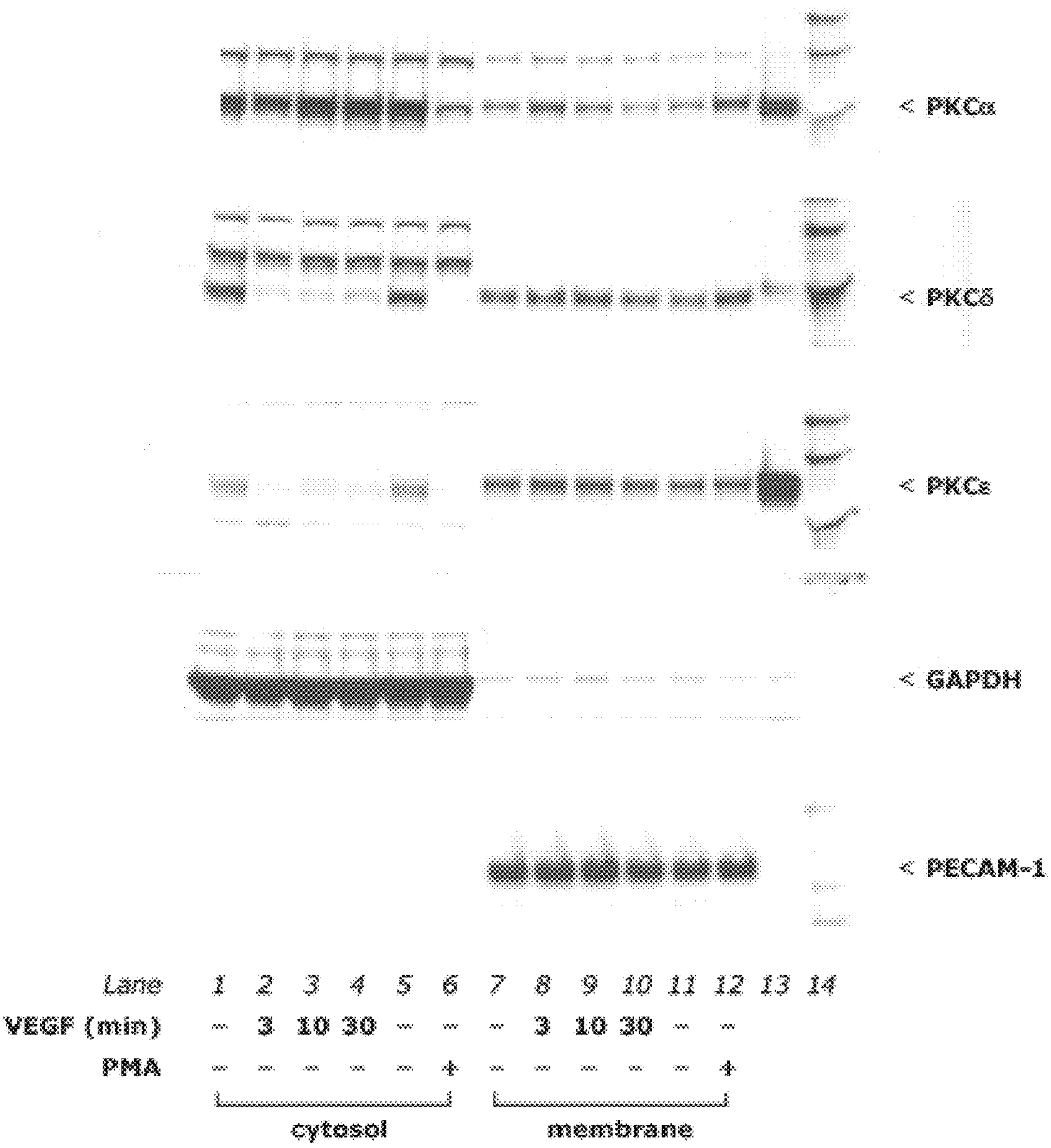
FIG. 3 is a set of immunoblots in which membrane translocation of PKC isoforms was analyzed. Lane 13: bovine brain lysate, used as a positive control. Lane 14: molecular weight standards. "B", bovine brain lysate, used as a positive control. "M", molecular weight marker.

BAEC were stimulated with VEGF (1 nM; 3, 10, or 30 minutes) or PMA (100 nM, 10 minutes). Immunoblots of PKCα, δ, and ϵ protein in cytosol and membrane fractions, separated by ultracentrifugation are shown in FIG. 3. PKCα, δ, and ϵ protein was detected in whole cell lysate and after immunoblotting of cytosol and membrane fractions of BAEC lysate (FIG. 3). Real-time PCR with primers targeting the sequence common to PKCβ1 and β2 gave clear amplification using RNA isolated from bovine brain and PKCβ1 and β2 protein was detected in bovine brain lysate. However, PKCβ mRNA was not detected in RNA isolated from BAEC and PKCβ1 or β2 protein was not detected in whole BAEC lysate (results not shown). PKCθ protein was not detected in whole BAEC lysate either (results not shown). Both VEGF and PMA stimulated translocation of PKCα, δ, and ϵ from cytosol to membrane fractions (FIG. 3). Similar results were obtained in 3 independent experiments.

Figure 4:
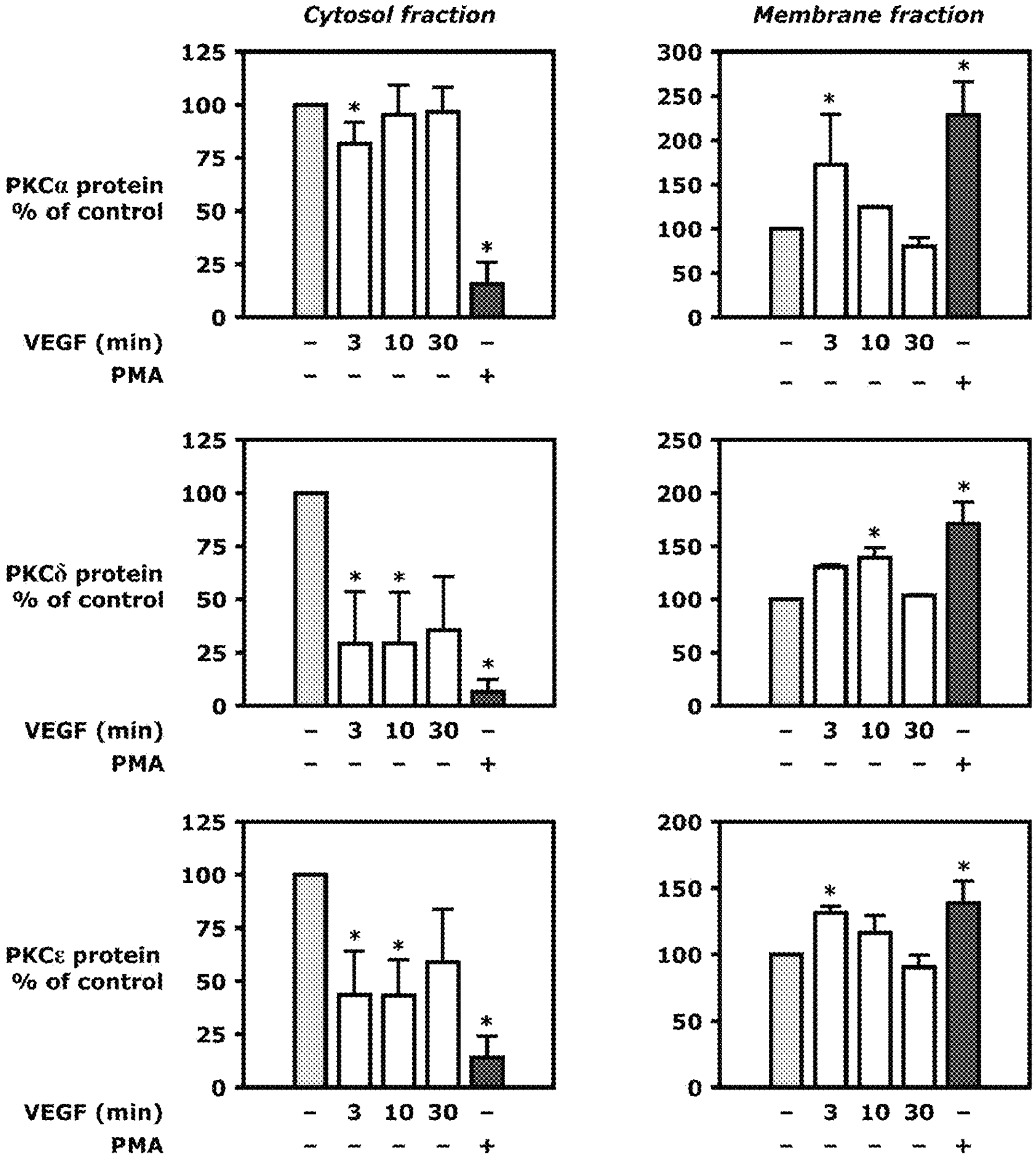
FIG. 4 is a set of bar graphs in which membrane translocation of PKC isoform was analyzed. Data from densitometry analysis of immunoblots of PKC isoforms in membrane and cytosol fractions are shown (mean data of three independent experiments ("*", $p<0.05$)).
Figure 5A:
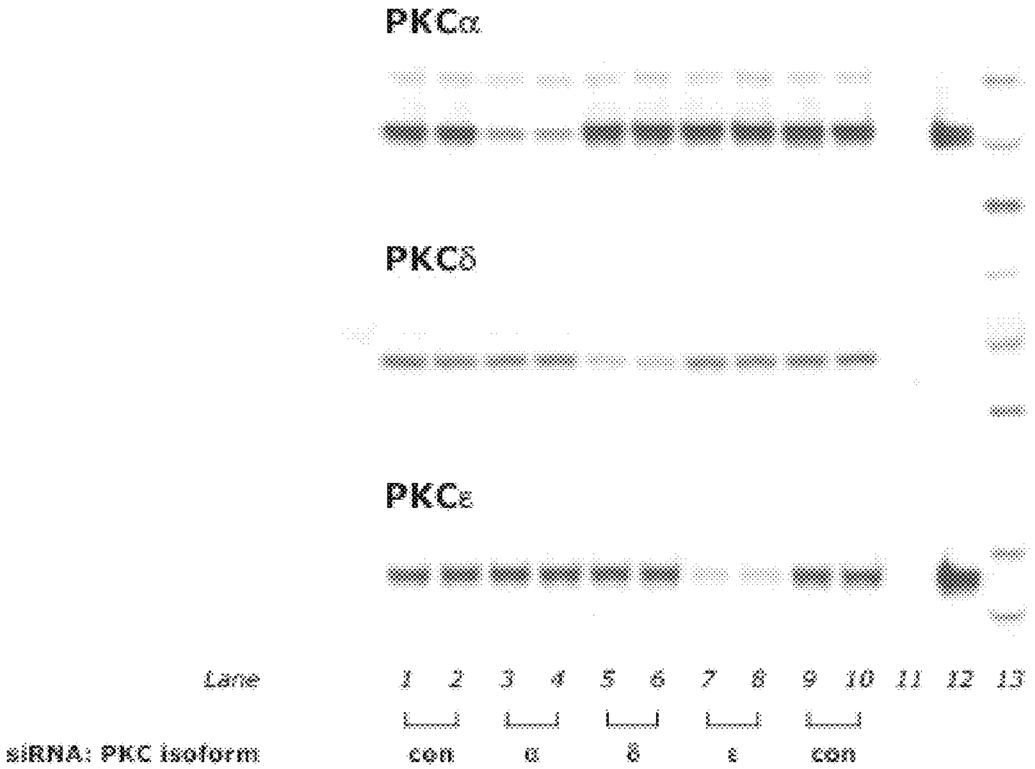
FIGS. 5A-D are a set of immunoblots and bar graphs in which siRNA-mediated knockdown of PKC isoforms in bovine aortic endothelial cells (BAEC) was analyzed. Data from BAEC transfected with siRNA targeting a gene not present in mammalian cells (con); or targeting PKCα, δ, or ϵ, are shown.
Figure 5B:
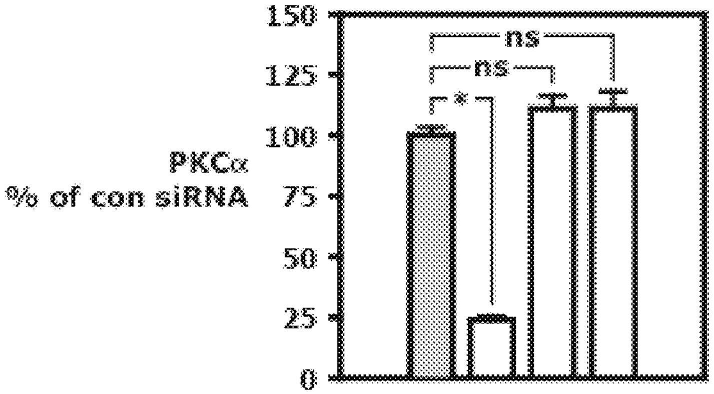
Figure 5C:
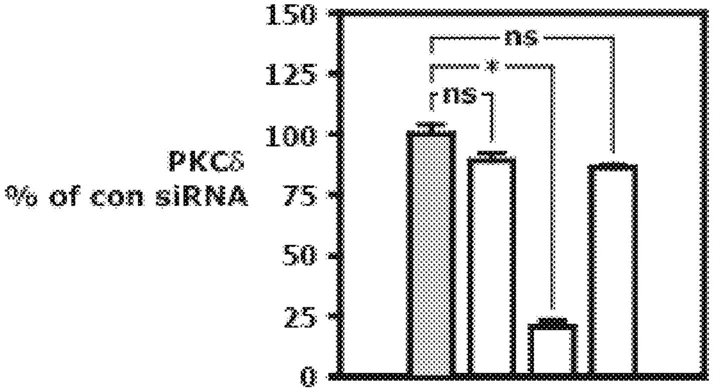
Figure 5D:
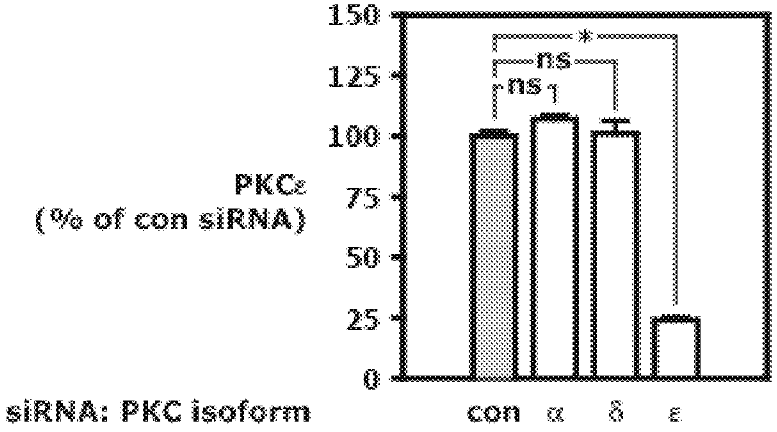

The cytosol expression of each PKC isoform decreased at 3 minutes, the earliest time point studied (FIG. 3). In parallel, the membrane expression for each isoform increased with a maximum at 3 or 10 minutes (FIG. 3). The maximal decrease in cytosol expression was 18±10, 29±25, and 57±21% for PKCα, δ, and ϵ, respectively (all at 3 minutes), whereas the maximal increase in membrane expression was 72±57, 39±10, and 31±5%, respectively (at 3, 10, and 3 minutes, respectively) (FIG. 4, $p<0.05$). In these preparations, the efficacy of cell fractionation was shown by immunoblotting of the cytosolic protein glyceraldehyde-3-phosphate dehydrogenase (GAPDH) and the membrane protein platelet/endothelial cell adhesion molecule-1/CD31 (PECAM-1), with only trace amounts of GAPDH and PECAM-1 in the membrane and cytosol fraction, respectively (FIG. 3).

Thus, PKCϵ is present and active in BAEC.

Example 4

In order to specifically inhibit individual PKC isoforms, siRNA targeting bovine PKCα, δ, and ϵ were designed as described above. BAEC were transfected with siRNA targeting a gene not present in mammalian cells (con); or targeting PKCα, δ, or ϵ. Cells were lysed 3 days after transfection and after 16 hours of serum starvation. Transfection of BAEC with PKC siRNAs downregulated PKCα, δ, and ϵ protein levels by 76±3, 89±3, and 76±2%, respectively (FIGS. 5*a-d*, $p<0.005$). Importantly, each siRNA only changed the expression of the targeted isoform and not any of the two other isoforms (FIG. 5).

Akt and eNOS phosphorylation in siRNA-transfected, VEGF treated (1 nM, 5 minutes) BAEC was examined. PKCα knockdown did not change unstimulated Akt phosphorylation, but increased VEGF-stimulated Akt phosphorylation (1.7±0.1-fold increase during control siRNA condition, 2.3-fold during the PKCα siRNA condition, FIG. 6*a*, $p<0.05$ compared to the control siRNA condition). PKCδ knockdown did not change unstimulated or VEGF-stimulated Akt phosphorylation (FIG. 6*a*, $p=0.7$ compared to the control siRNA condition).

Figure 6A:
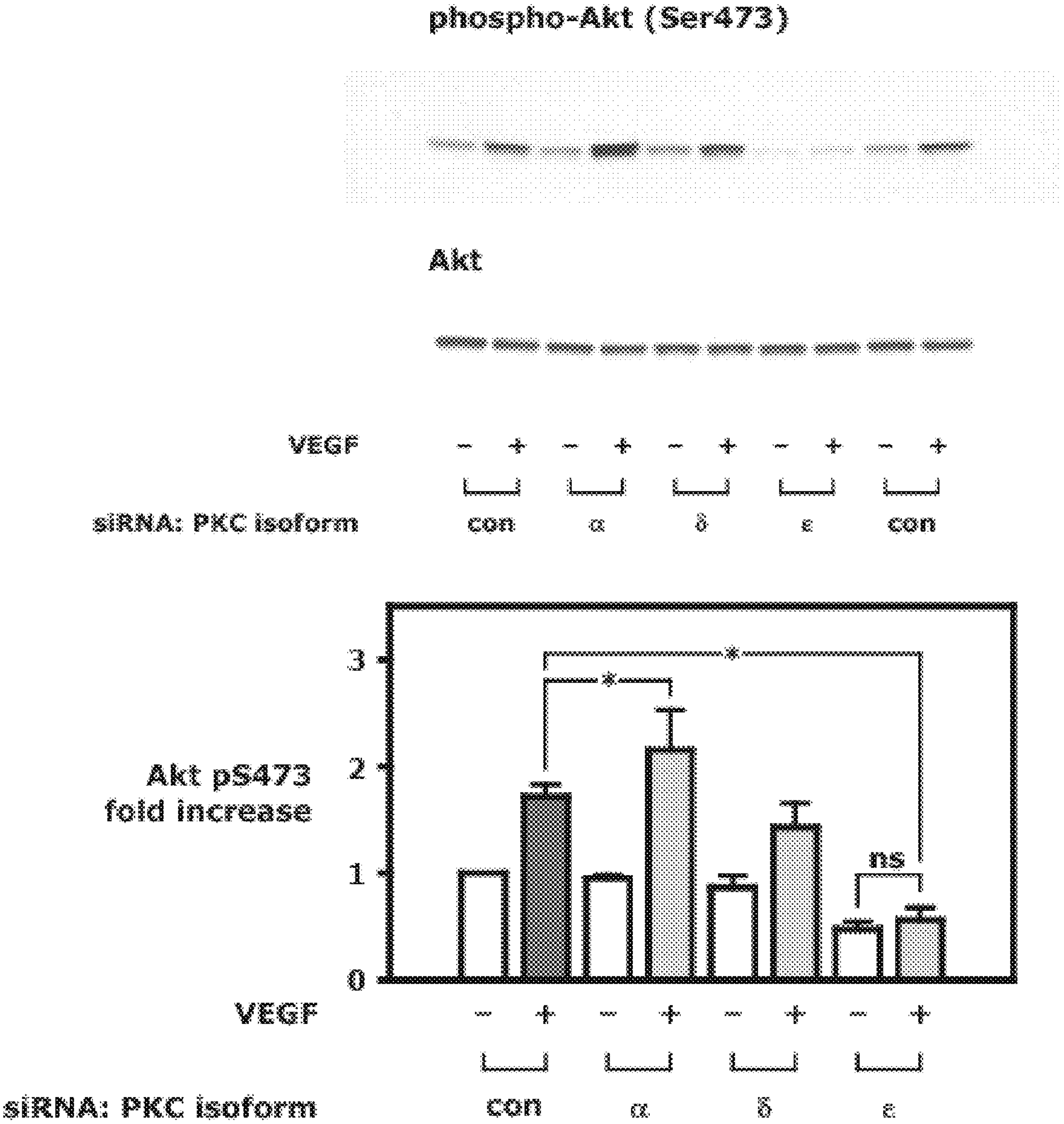
FIGS. 6A-B are sets of immunoblots and bar graphs in which phosphorylation of Akt (FIG. 6A) and eNOS (FIG. 6B) by VEGF during siRNA-mediated knockdown of PKC isoforms were analyzed. Representative immunoblots are shown above mean data of the phospho-protein normalized to the control condition.

Unexpectedly, PKCϵ knockdown decreased unstimulated Aid phosphorylation (by 53±7%, FIG. 6*a*), and completely inhibited VEGF-stimulated Akt phosphorylation (1.1±0.2-fold increase during PKCϵ siRNA, FIG. 6*a*, $p=0.4$).

Figure 6B:
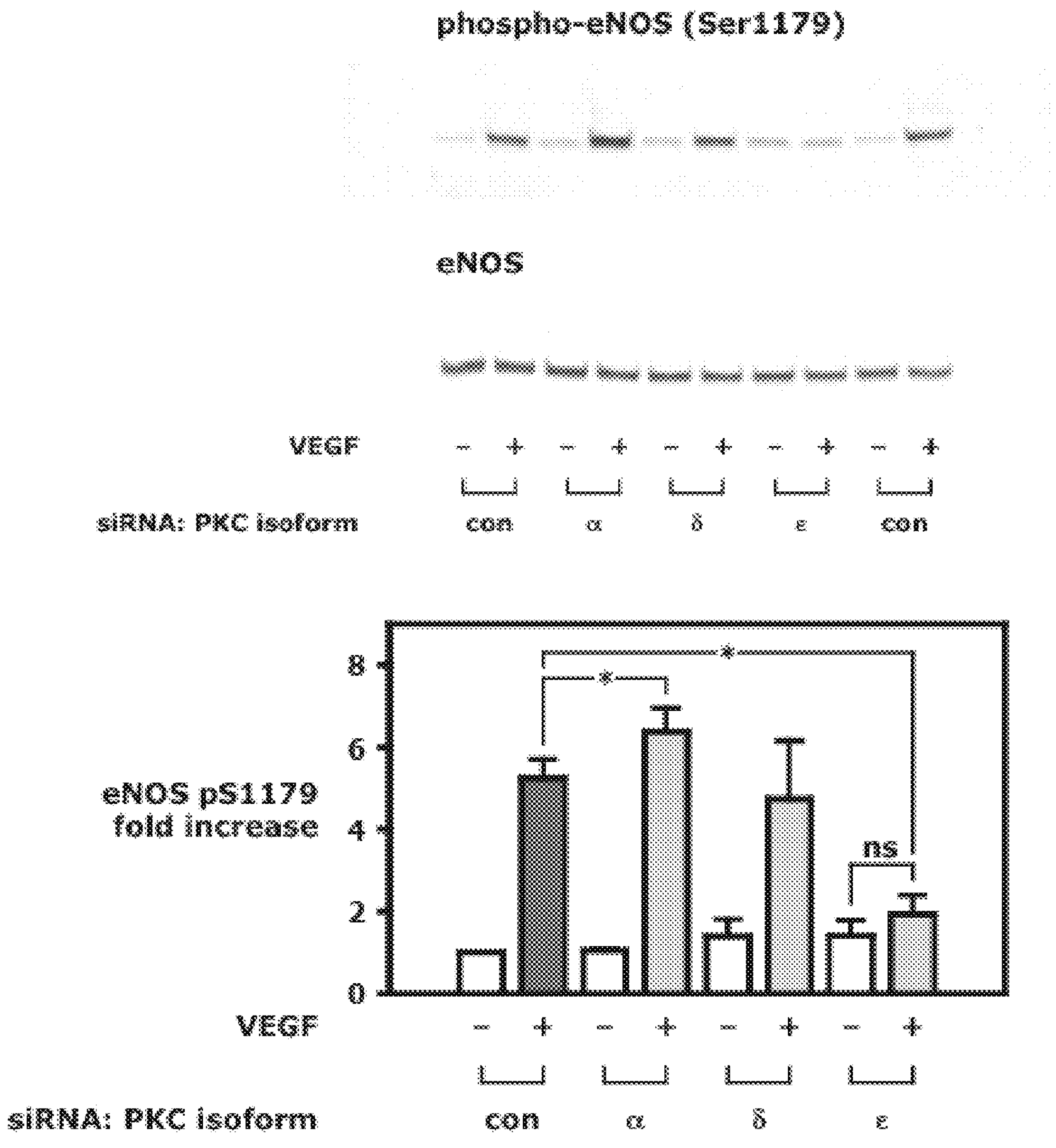

Basal levels of eNOS Ser1179 phosphorylation was unchanged by PKCα knockdown (FIG. 6*b*), but increased by PKCδ and ϵ knockdown, although this change was not statistically significant (to 139±42% and 141±37%, respectively, of the level during the control siRNA condition, FIG. 6*b*). The effect of PKCα, δ, and ϵ knockdown on VEGF-stimulated eNOS phosphorylation paralleled the effects on Akt phosphorylation. Thus, VEGF-stimulated eNOS phosphorylation was increased during PKCα knockdown, unchanged during PKCδ knockdown, and completely prevented by PKCϵ knockdown (5.2±0.5, p=6.1±0.1, 4.2±0.3, and 1.7±0.3-fold increase in the control, PKCα siRNA condition, PKCδ, and PKCϵ siRNA conditions, respectively; $p=0.02$ and $p=0.2$ when comparing the control siRNA condition to PKCα and δ, respectively; $p=0.4$ for the VEGF stimulation during the PKCϵ siRNA condition (FIG. 6*b*)).

Figure 8:
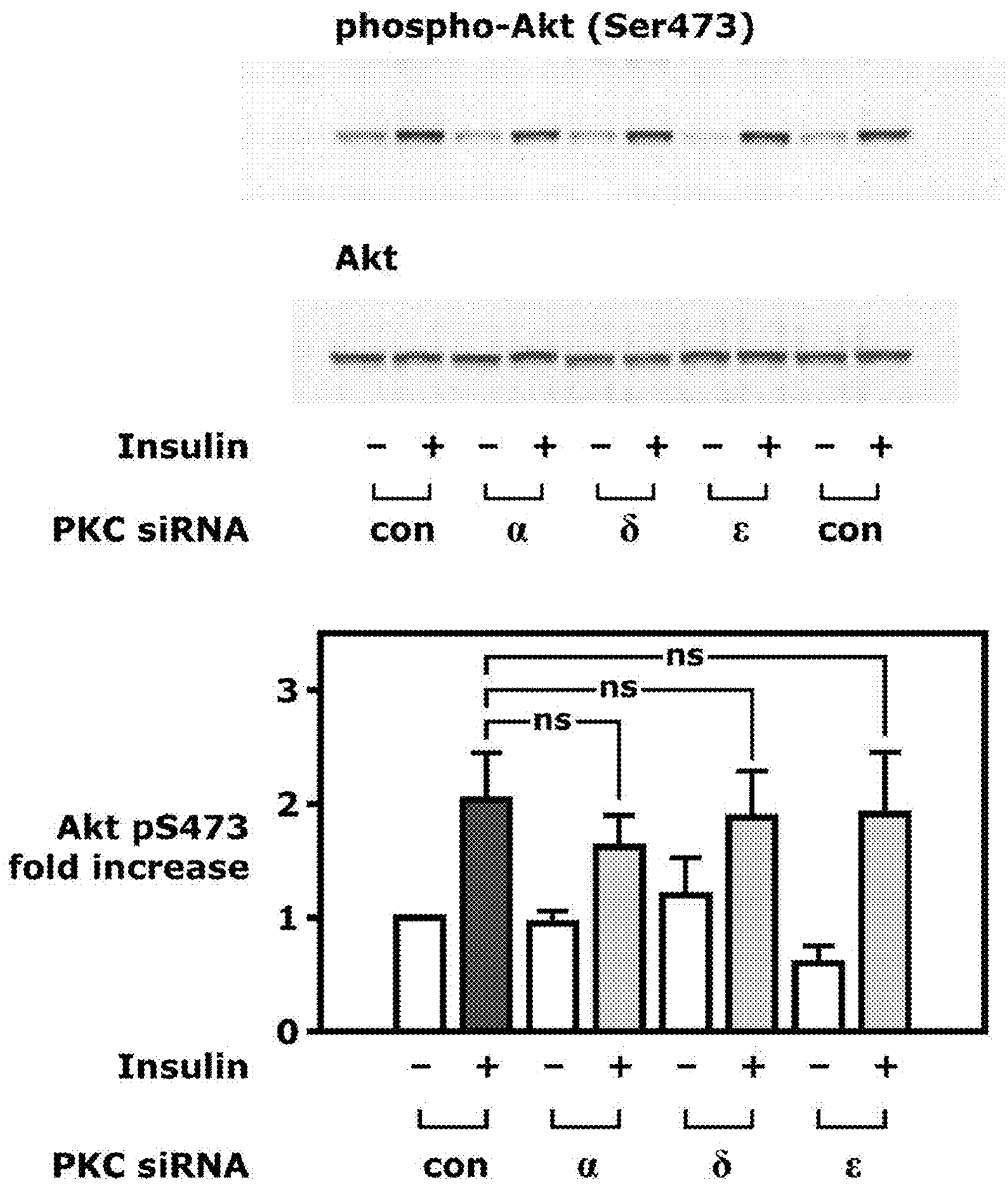
FIG. 8 is a set of immunoblots and a bar graph in which phosphorylation of Akt and eNOS by insulin during siRNA-mediated knockdown of PKC isoforms was analyzed. Representative immunoblots are shown above mean data of the phospho-protein normalized to the control condition (n=3; "*", p<0.05).

Phosphorylation in insulin stimulated cells was also examined. BAEC were transfected with siRNA, grown, and serum-starved as described in above. Cultures were then stimulated with insulin (100 nM, 5 minutes). PKCα, δ, or ϵ knockdown did not change Akt phosphorylation stimulated by insulin (FIG. 8) or insulin-like growth factor (data not shown). Thus, downregulation of PKC isoforms selectively affected VEGF signaling.

Figure 7:
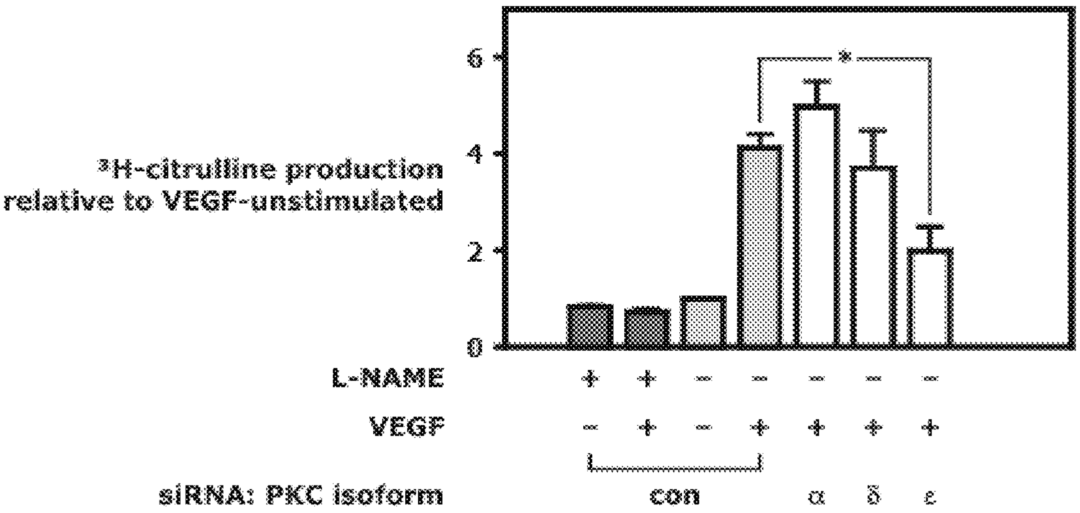
FIG. 7 is a bar graph depicting NO synthase activity in intact in BAEC with siRNA-mediated knockdown of PKC isoforms. BAEC were transfected with siRNA targeting a gene not present in mammalian cells (con); or targeting PKCα, δ, or ϵ. NO synthase activity was measured as the radioactivity of $^{3}$H-L-citrulline in the cell lysate (n=4; *, $p<0.05$).

In turn, changes in VEGF-stimulated NO synthase activity, measured in intact cell cultures by conversion of $^3$H-L-arginine to $^3$H-L-citrulline, largely paralleled eNOS phosphorylation. Thus, PKCα knockdown increased (by 15±3%) and PKCϵ knockdown decreased (by 50±7%) VEGF-stimulated NO synthase activity (FIG. 7). Although PKCδ knockdown did not significantly affect VEGF-stimulated eNOS phosphorylation (FIG. 6*b*), it decreased NOS activity (by 17±6% p=0.02).

NO synthase activity in siRNA transfected cells was examined. BAEC were transfected with siRNA targeting a gene not present in mammalian cells (control); or targeting PKCα, δ, or ϵ. Three days after transfection, 16 hours after the beginning of serum starvation, 3 hours after the beginning of L-arginine starvation, and 30 minutes after addition of L-NAME (as indicated on FIG. 7), cells were incubated with $^3$H-L-arginine and VEGF (1 nM, 10 minutes) for 10 minutes. PKCϵ knockdown completely prevented eNOS phosphorylation (FIG. 6*b*), but only partly prevented NO synthase activity (FIG. 7), suggesting that eNOS activity is regulated both by phosphorylation and $[Ca^{2+}]_i$ changes. Accordingly, incubation of BAEC in a buffer without $Ca^{2+}$ prior to the activity assay completely prevented VEGF-stimulated NO synthase activity (FIG. 7).

Figure 9:
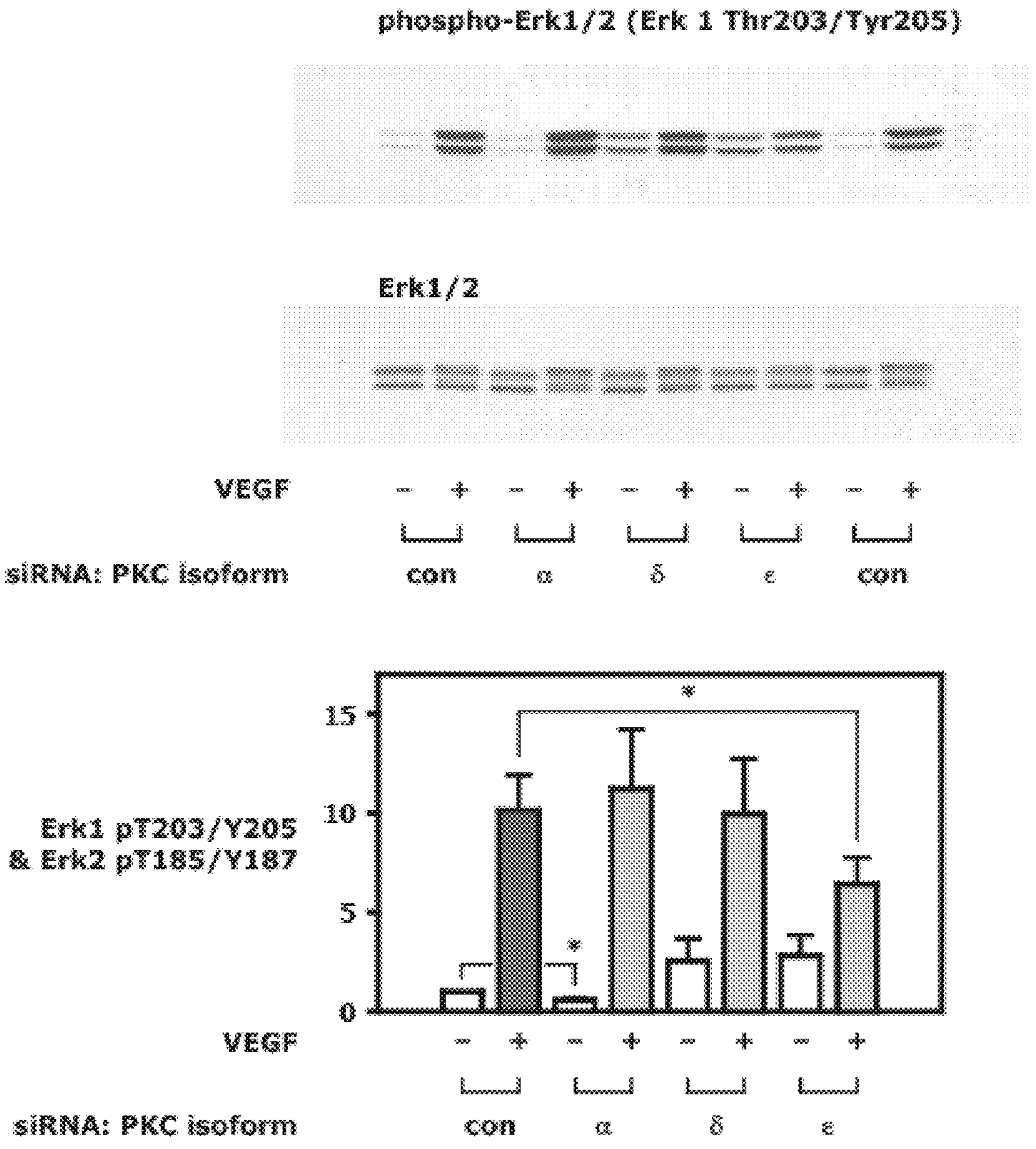
FIG. 9 is a set of immunoblots and a bar graph in which Erk1/2 phosphorylation stimulated by VEGF in BAEC with siRNA-mediated knockdown of PKC isoforms was examined. BAEC were transfected with siRNA targeting a gene not present in mammalian cells (con); or targeting PKCα, δ, or ε. Representative immunoblots are shown above mean data for the phospho-protein normalized to the control condition (n=3; *, p<0.05).

The involvement of PKCϵ in VEGF signaling was not confined to Akt-eNOS signaling. Erk1/2 phosphorylation of BAEC with siRNA knockdown of PKC isoforms was examined. Three days after transfection and 16 hours of serum starvation, cells were stimulated with VEGF (1 nM, 5 minutes). VEGF increased phosphorylation of Erk1/2 by 10±1.8-fold after transfection of BAEC with control siRNA (at residues Thr202 and Tyr204 in Erk1/p44 MAPK, homologous to Thr203/Tyr205 in the bovine sequence) (FIG. 9). However, PKCϵ knockdown decreased VEGF-stimulated phosphorylation of Erk1/2 (2.7±0.9-fold in the PKCϵ siRNA condition, p=0.01 compared to the control siRNA condition, FIG. 9). During PKCα knockdown, unstimulated Erk1/2 phosphorylation was decreased to 55±17% of the level during the control siRNA condition (p<0.05, FIG. 9). The absolute level of Erk phosphorylation was not changed by PKCα knockdown, but because of the decrease in phosphorylation in the unstimulated condition, the relative increase was larger (19.8±2.1-fold between VEGF-unstimulated and -stimulated conditions during PKCα knockdown). Unstimulated Erk1/2 phosphorylation was increased during PKCδ and ϵ knockdown, but this was not statistically significant (FIG. 9). PKCδ and ϵ knockdown did not change VEGF-stimulated Erk1/2 phosphorylation (FIG. 9). A mobility shift of both the Erk1 and Erk2 bands are visible in all VEGF-stimulated conditions.

PKCϵ appears to mediate several VEGF-activated signaling pathways and functions in endothelial cells. These results demonstrate that PKCϵ is essential for VEGF-stimulated phosphorylation of Akt and eNOS and activation of eNOS in endothelial cells. These results further suggest that PKCϵ is involved in mediating VEGF-stimulated eNOS activation through both Akt-dependent and -independent pathways, since the reduction of PKCϵ by siRNA completely inhibited Akt and eNOS phosphorylation in parallel.

In contrast, wortmannin, which specifically inhibits PI3K, decreased Akt phosphorylation fully, but only caused partial inhibition of eNOS phosphorylation at Ser1179. These data indicate that the phosphorylation of eNOS at Ser1179 and its activation by VEGF is only partially mediated by the PI3K/Akt pathway.

The role of PKCϵ as a mediator of VEGF signaling may be more general than the regulation of Akt and eNOS, since PKCϵ knockdown also significantly inhibited VEGF-stimulated Erk1/2 phosphorylation and DNA synthesis. Unlike the effect on Akt and eNOS phosphorylation, VEGF-stimulated Erk1/2 activation was only partially inhibited by PKCϵ knockdown. This indicates that there are separate pathways involved in the growth-promoting actions of VEGF that may not require activation of PKCϵ. Another potential signaling pathway used by VEGF to phosphorylate and activate eNOS is via the AMPK pathway, as suggested in previous publications (27-30). In preliminary experiments, PKCϵ also mediates VEGF-induced AMPK activation.

These findings suggest that PKCϵ is activated early in the VEGF signaling cascade, and thus is a candidate therapeutic target for modulation of angiogenesis and other VEGF-induced growth processes.

Example 5

Figure 10:
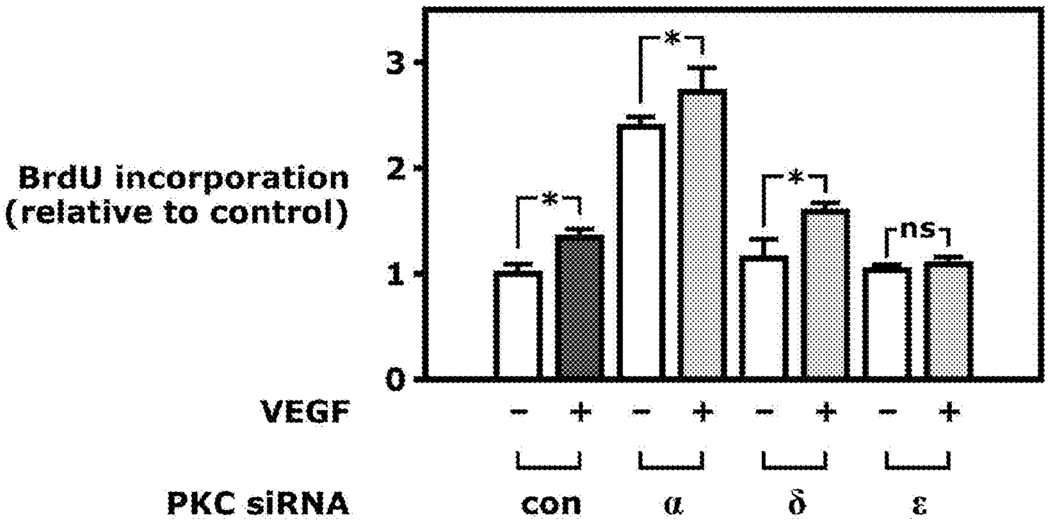
FIG. 10 is a bar graph depicting relative BrdU stimulated by VEGF in BAEC with siRNA-mediated knockdown of PKC isoforms.

To evaluate cellular function known to be regulated by Erk signaling, DNA synthesis was measured by BrdU incorporation assays. PKCα knockdown increased BrdU incorporation without VEGF stimulation to 239% of the control value (p<0.001, FIG. 10), but the unstimulated BrdU incorporation did not change during PKCδ or ϵ knockdown. VEGF increased BrdU incorporation by 34% in the control siRNA condition (p<0.01, FIG. 10) and by 14% and 39% during PKCα and δ knockdown (p<0.05, FIG. 10). In contrast, PKCϵ knockdown completely inhibited VEGF-stimulated BrdU incorporation (FIG. 10).

The findings that Akt and Erk signal transduction, which are usually considered to have limited cross-talk, were both affected by PKCϵ knockdown, pointed to a role for PKCϵ early in VEGF signal transduction. Therefore, VEGFR2 activation, which is responsible for most known actions of VEGF, including activation of eNOS, was examined. BAEC were transfected with siRNA, grown, and serum-starved, then stimulated with VEGF (1 nM, 5 minutes). Immunoprecipitation was performed with a VEGFR2 antibody followed by immunoblotting with a phospho-tyrosine antibody or VEGFR2 antibody.

Figure 11:
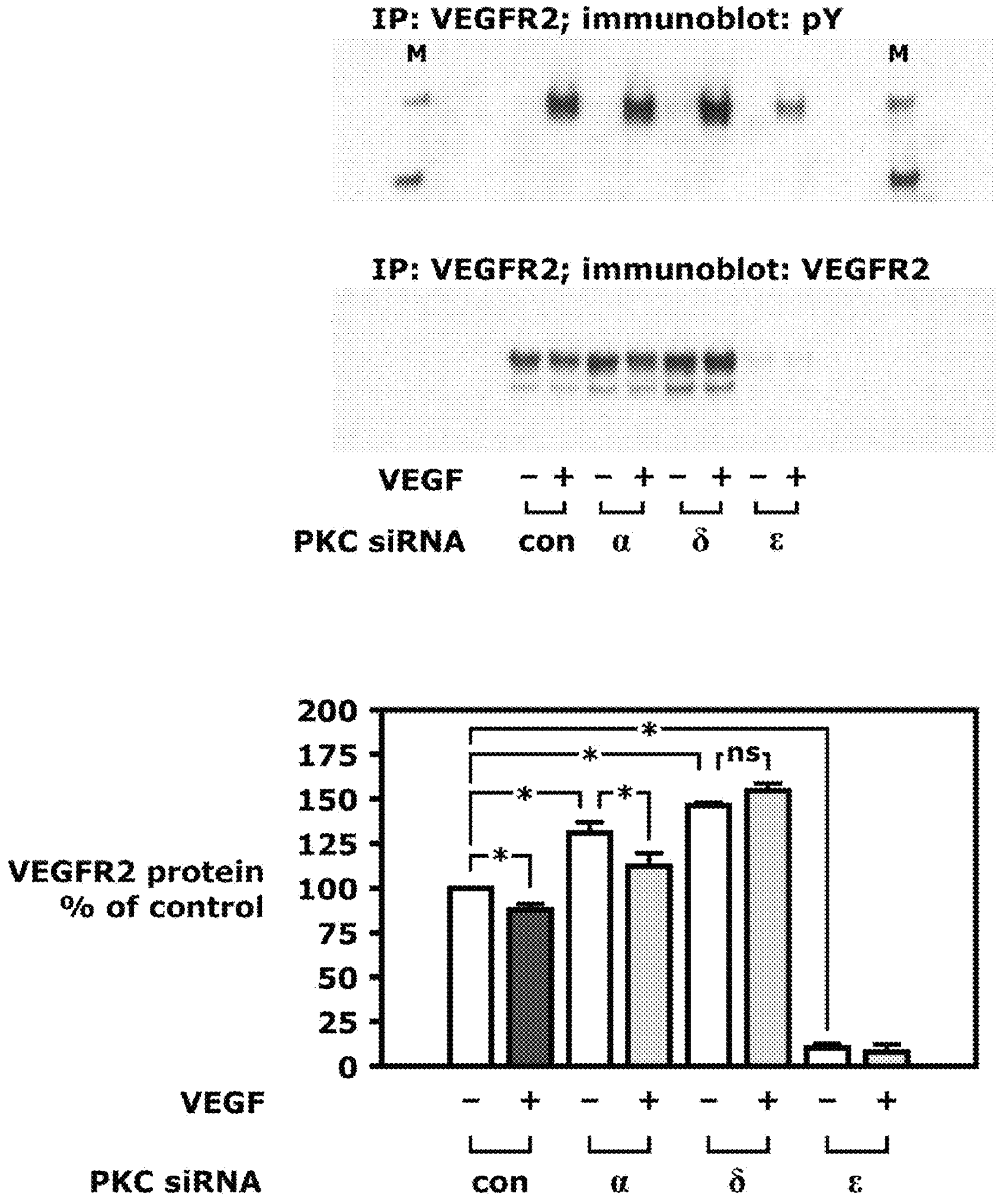
FIG. 11 is a set of immunoblots and a bar graph depicting analysis of tyrosine phosphorylation and protein expression of VEGFR2 in BAEC during siRNA-mediated knockdown of PKC isoforms. Representative immunoblots are shown above a graph of mean densitometry data from VEGFR2 immunoblots (4-7 independent experiments; "*", p<0.05).

PKCϵ knockdown decreased VEGF-stimulated VEGFR2 tyrosine phosphorylation by 81±6% compared to transfection with control siRNA (p<0.001, FIG. 11), whereas PKCα and δ knockdown increased tyrosine phosphorylation by 38±18 and 33±12%, respectively (p<0.05, FIG. 11). These changes reflected changes in VEGFR2 protein expression. PKCϵ knockdown caused a dramatic reduction in VEGFR2 protein to only 10±2% of the control value (p<0.001, FIG. 11). In contrast, PKCα and δ increased VEGFR2 protein by 31±6 and 46±2%, respectively (p<0.05, FIG. 11). VEGF stimulation caused a 12±3% decrease in VEGFR2 protein in cells transfected with control siRNA, likely representing ligand-stimulated downregulation of the receptor (p<0.05, FIG. 11). A VEGF-stimulated decreased in VEGFR2 protein (by 17±3%) was preserved during PKCα knockdown, but not detectable during PKCδ or ϵ knockdown.

Figure 12A:
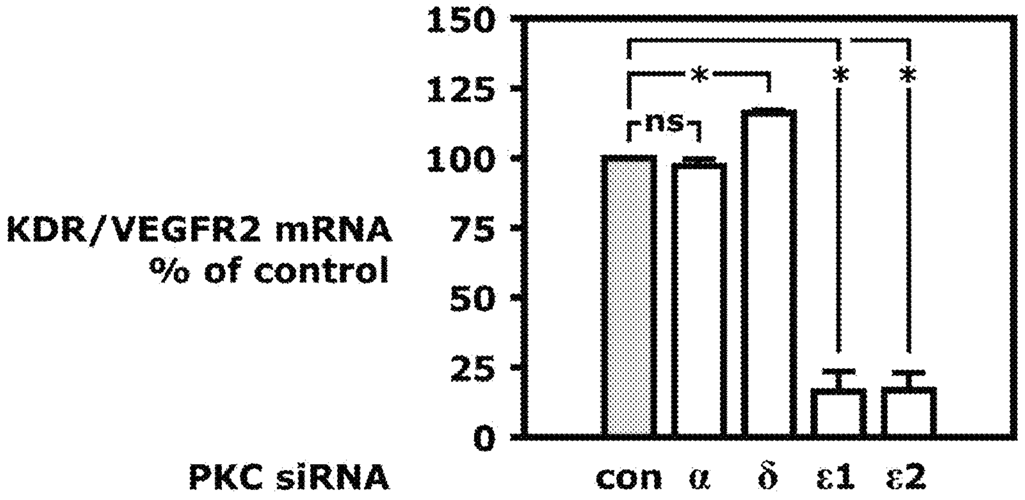
FIGS. 12A and 12B are bar graphs of relative levels of VEGFR2 and VEGFR1 mRNA expression in BAEC during siRNA-mediated knockdown of PKC isoforms. VEGFR2 (FIG. 12A) or VEGFR1 (FIG. 12B) mRNA was measured in cell lysate by real-time PCR (n=3; "*", p<0.05).

In VEGFR2 immunoblots (FIG. 11), the less intense, slower migrating (200 kDa) band may represent an intermediary, cytosolic form, whereas the more intense, upper (230 kDa) band may represent the fully N-glycosylated receptor expressed at the cell surface (Takahashi et al., Oncogene, 14(17):2079-2089, 1997). Of note, PKCε knockdown reduced both bands, suggesting that it affects transcription, translation, or early post-translational modification rather than promoting internalization and degradation of the surface-bound receptor (Wang et al., J. Biol. Chem., 275(21): 15905-15911, 2000). Therefore, VEGFR2 mRNA expression was measured with real-time PCR during knockdown of PKCα, δ, and ε. A second siRNA targeting a different region of PKCε mRNA was used to minimize the possibility that the effect on VEGFR2 expression was due to an off-target effect. Compared with the control siRNA condition, VEGFR2 mRNA expression decreased by 84±7 and 83±6% during PKCε knockdown with the original and additional siRNA, respectively (FIG. 12*a*, p<0.001). Thus, PKCε appears to regulate VEGFR2 at the mRNA level. PKCα knockdown had no significant effect, whereas PKCδ increased VEGFR2 mRNA by 16±1% (FIG. 12*a*, p<0.001).

Figure 12B:
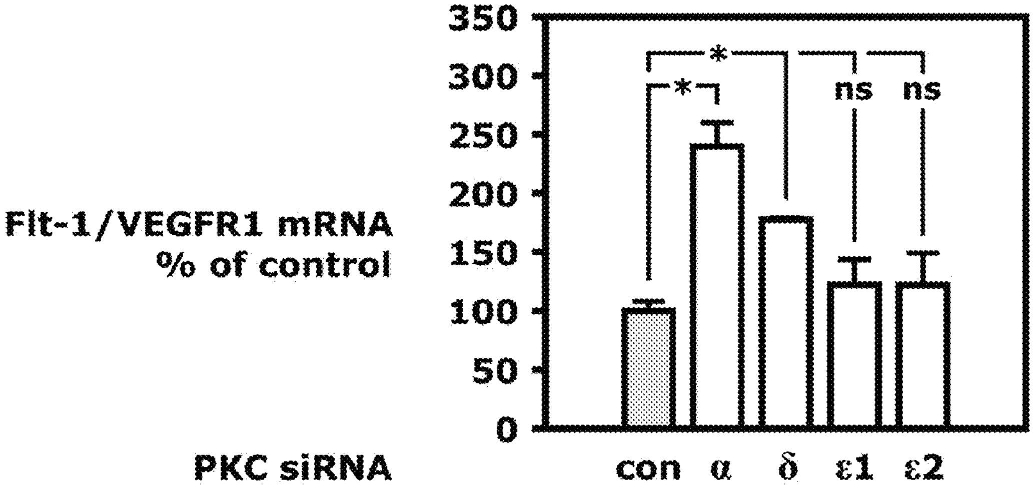

Next, VEGFR1 and VEGFR2 expression was examined. BAEC were transfected with siRNA, including the PKCε siRNA used in the previous experiments (abbreviated "ε1" here) and a second PKCε ("ε2"), grown, and serum-starved. VEGFR2 (a) or VEGFR1 (b) mRNA was measured in cell lysate by real-time PCR VEGF signal transduction during PKC knockdown could change because VEGFR2 expression results in a secondary change in VEGFR1/Fms-like tyrosine kinase-1 (Flt-1) expression. Indeed, PKCα and PKCδ knockdown increased VEGFR1 mRNA expression to 240±20 and 178±1% of the control siRNA condition, respectively (FIG. 12*b*, p<0.01). However, VEGFR1 mRNA did not change significantly during PKCε knockdown with either of the two siRNAs (FIG. 12*b*). VEGFR1 protein or VEGFR1-mediated signal transduction was not detected by Western blotting in these cells. VEGFR1 protein was not detectable in whole cell lysate (using two different commercially available antibodies) and VEGFR1 or phosphotyrosine was not detectable in immunoprecipitates with VEGFR1 antibody with or without stimulation with VEGF; furthermore, placental growth factor, which activates VEGFR1 but not VEGFR2, did not increase phosphorylation of eNOS, Akt, Erk, or p38 (data not shown). Thus, VEGFR1 protein is likely expressed at a very low level compared to VEGFR2 in BAEC. Changes seen in VEGF signal transduction during PKCα and δ knockdown could be influenced by upregulation of VEGFR1, but there is no indication that changes in VEGF signaling during PKCε knockdown can be attributed to changes in VEGFR1 mRNA expression.

References

1. Hoeben A, Landuyt B, Highley M S, Wildiers H, Van Oosterom A T, De Bruijn E A. Vascular endothelial growth factor and angiogenesis. Pharmacol Rev 2004; 56(4):549-80.

2. Matsumoto T, Claesson-Welsh L. VEGF receptor signal transduction. Sci STKE 2001; 2001(112):RE21.

3. Zachary I. Signaling mechanisms mediating vascular protective actions of vascular endothelial growth factor. Am J Physiol Cell Physiol 2001; 280(6):C1375-86.

4. Fulton D, Gratton J P, McCabe T J, Fontana J, Fujio Y, Walsh K, Franke T F, Papapetropoulos A, Sessa W C. Regulation of endothelium-derived nitric oxide production by the protein kinase Akt. Nature 1999; 399(6736):597-601.

5. Brouet A, Sonveaux P, Dessy C, Balligand J L, Feron O. Hsp90 ensures the transition from the early Ca2+-dependent to the late phosphorylation-dependent activation of the endothelial nitric-oxide synthase in vascular endothelial growth factor-exposed endothelial cells. J Biol Chem 2001; 276(35): 32663-9. Epub 2001 Jun. 25.

6. Takahashi S, Mendelsohn M E. Synergistic activation of endothelial nitric-oxide synthase (eNOS) by HSP90 and Akt: calcium-independent eNOS activation involves formation of an HSP90-Akt-CaM-bound eNOS complex. J Biol Chem 2003; 278(33):30821-7.

7. Montagnani M, Chen H, Barr V A, Quon M J. Insulin-stimulated activation of eNOS is independent of Ca2+ but requires phosphorylation by Akt at Ser(1179). J Biol Chem 2001; 276(32):30392-8.

8. Xia P, Aiello L P, Ishii H, Jiang Z Y, Park D J, Robinson G S, Takagi H, Newsome W P, Jirousek M R, King G L. Characterization of vascular endothelial growth factor's effect on the activation of protein kinase C, its isoforms, and endothelial cell growth. J Clin Invest 1996; 98(9):2018-26.

9. Aiello L P, Bursell S E, Clermont A, Duh E, Ishii H, Takagi C, Mori F, Ciulla T A, Ways K, Jirousek M, Smith L E, King G L. Vascular endothelial growth factor-induced retinal permeability is mediated by protein kinase C in vivo and suppressed by an orally effective beta-isoform-selective inhibitor. Diabetes 1997; 46(9):1473-80.

10. Kou R, Greif D, Michel T. Dephosphorylation of endothelial nitric-oxide synthase by vascular endothelial growth factor. Implications for the vascular responses to cyclosporin A. J Biol Chem 2002; 277(33):29669-73.

11. He H, Venema V J, Gu X, Venema R C, Marrero M B, Caldwell R B. Vascular endothelial growth factor signals endothelial cell production of nitric oxide and prostacyclin through flk-1/KDR activation of c-Src. J Biol Chem 1999; 274(35):25130-5.

12. Michell B J, Griffiths J E, Mitchelhill K I, Rodriguez-Crespo I, Tiganis T, Bozinovski S, de Montellano P R, Kemp B E, Pearson R B. The Akt kinase signals directly to endothelial nitric oxide synthase. Curr Biol 1999; 9(15):845-8.

13. Boo Y C, Sorescu G, Boyd N, Shiojima I, Walsh K, Du J, Jo H. Shear stress stimulates phosphorylation of endothelial nitric-oxide synthase at Ser1179 by Akt-independent mechanisms: role of protein kinase A. J Biol Chem 2002; 277(5):3388-96.

14. Kuboki K, Jiang Z Y, Takahara N, Ha S W, Igarashi M, Yamauchi T, Feener E P, Herbert T P, Rhodes C J, King G L. Regulation of endothelial constitutive nitric oxide synthase gene expression in endothelial cells and in vivo: a specific vascular action of insulin. Circulation 2000; 101(6):676-681.

15. Wu L W, Mayo L D, Dunbar J D, Kessler K M, Baerwald M R, Jaffe E A, Wang D, Warren R S, Donner D B. Utilization of distinct signaling pathways by receptors for vascular endothelial cell growth factor and other mitogens in the induction of endothelial cell proliferation. J Biol Chem 2000; 275(7):5096-103.

16. Jaffe E A, Nachman R L, Becker C G, Minick C R. Culture of human endothelial cells derived from umbilical veins. Identification by morphologic and immunologic criteria. J Clin Invest 1973; 52(11):2745-56.

17. Inoguchi T, Battan R, Handler E, Sportsman J R, Heath W, King G L. Preferential elevation of protein kinase C isoform beta II and diacylglycerol levels in the aorta and heart of diabetic rats: differential reversibility to glycemic control by islet cell transplantation. Proc Natl Acad Sci USA 1992; 89(22):11059-63.

18. Chiu Y L, Rana T M. RNAi in human cells: basic structural and functional features of small interfering RNA. Mol Cell 2002; 10(3):549-61.

19. Elbashir S M, Harborth J, Weber K, Tuschl T. Analysis of gene function in somatic mammalian cells using small interfering RNAs. Methods 2002; 26(2).

20. Igarashi J, Michel T. Agonist-modulated targeting of the EDG-1 receptor to plasmalemmal caveolae. eNOS activation by sphingosine 1-phosphate and the role of caveolin-1 in sphingolipid signal transduction. J Biol Chem 2000; 275 (41):32363-70.

21. Rask-Madsen C, King G L. Proatherosclerotic mechanisms involving protein kinase C in diabetes and insulin resistance. Arterioscler Thromb Vasc Biol 2005; 25(3):487-96.

22. Dimmeler S, Fleming I, Fisslthaler B, Hermann C, Busse R, Zeiher A M. Activation of nitric oxide synthase in endothelial cells by Akt-dependent phosphorylation. Nature 1999; 399(6736):601-605.

23. Gallis B, Corthals G L, Goodlett D R, Ueba H, Kim F, Presnell S R, Figeys D, Harrison D G, Berk B C, Aebersold R, Corson M A. Identification of flow-dependent endothelial nitric-oxide synthase phosphorylation sites by mass spectrometry and regulation of phosphorylation and nitric oxide production by the phosphatidylinositol 3-kinase inhibitor LY294002. J Biol Chem 1999; 274(42):30101-8.

24. Way K J, Chou E, King G L. Identification of PKC-isoform-specific biological actions using pharmacological approaches. Trends Pharmacol Sci 2000; 21(5):181-7.

25. Wellner M, Maasch C, Kupprion C, Lindschau C, Luft F C, Haller H. The proliferative effect of vascular endothelial growth factor requires protein kinase C-alpha and protein kinase C-zeta. Arterioscler Thromb Vasc Biol 1999; 19(1): 178-85.

26. Mason J C, Steinberg R, Lidington E A, Kinderlerer A R, Ohba M, Haskard D O. Decay-accelerating factor induction on vascular endothelium by vascular endothelial growth factor (VEGF) is mediated via a VEGF receptor-2 (VEGF-R2)- and protein kinase C-alpha/epsilon (PKCalpha/epsilon)-dependent cytoprotective signaling pathway and is inhibited by cyclosporin A. J Biol Chem 2004; 279(40):41611-8.

27. Chen Z P, Mitchelhill K I, Michell B J, Stapleton D, Rodriguez-Crespo I, Witters L A, Power D A, Ortiz de Montellano P R, Kemp B E. AMP-activated protein kinase phosphorylation of endothelial NO synthase. FEBS Lett 1999; 443(3):285-9.

28. Zou M H, Hou X Y, Shi C M, Nagata D, Walsh K, Cohen R A. Modulation by peroxynitrite of Akt- and AMP-activated kinase-dependent Ser1179 phosphorylation of endothelial nitric oxide synthase. J Biol Chem 2002; 277(36):32552-7.

29. Nagata D, Mogi M, Walsh K. AMP-activated protein kinase (AMPK) signaling in endothelial cells is essential for angiogenesis in response to hypoxic stress. J Biol Chem 2003; 278(33):31000-6.

30. Morrow V A, Foufelle F, Connell J M, Petrie J R, Gould G W, Salt I P. Direct activation of AMP-activated protein kinase stimulates nitric-oxide synthesis in human aortic endothelial cells. J Biol Chem 2003; 278(34):31629-39.

31. Littler C M, Wehling C A, Wick M J, Fagan K A, Cool C D, Messing R O, Dempsey E C. Divergent contractile and structural responses of the murine PKC-epsilon null pulmonary circulation to chronic hypoxia. Am J Physiol Lung Cell Mol Physiol 2005; 289(6):L1083-93.

32. Song C, Vondriska T M, Wang G W, Klein J B, Cao X, Zhang J, Kang Y J, D'Souza S, Ping P. Molecular conformation dictates signaling module formation: example of PKCepsilon and Src tyrosine kinase. Am J Physiol Heart Circ Physiol 2002; 282(3):H1166-71.

33. Ping P, Song C, Zhang J, Guo Y, Cao X, Li R C, Wu W, Vondriska T M, Pass J M, Tang X L, Pierce W M, Bolli R. Formation of protein kinase C(epsilon)-Lck signaling modules confers cardioprotection. J Clin Invest 2002; 109(4):499-507.

34. Pedram A, Razandi M, Levin E R. Deciphering vascular endothelial cell growth factor/vascular permeability factor signaling to vascular permeability. Inhibition by atrial natriuretic peptide. J Biol Chem 2002; 277(46):44385-98.

35. Zhang J, Baines C P, Zong C, Cardwell E M, Wang G, Vondriska T M, Ping P. Functional proteomic analysis of a three-tier PKCepsilon-Akt-eNOS signaling module in cardiac protection. Am J Physiol Heart Circ Physiol 2005; 288 (2):H954-61.

36. Naruse K, Rask-Madsen C, Takahara N, Ha S W, Suzuma K, Way K J, Jacobs J R, Clermont A C, Ueki K, Ohshiro Y, Zhang J, Goldfine A B, King G L. Activation of vascular protein kinase C-beta inhibits Akt-dependent endothelial nitric oxide synthase function in obesity-associated insulin resistance. Diabetes 2006; 55(3):691-8.

37. Xia P, Aiello L P, Ishii H, Jiang Z Y, Park D J, Robinson G S, Takagi H, Newsome W P, Jirousek M R, King G L. Characterization of vascular endothelial growth factor's effect on the activation of protein kinase C, its isoforms, and endothelial cell growth. J Clin Invest 1996; 98(9):2018-26.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting angiogenesis in a subject, the method comprising administering to a subject having an ocular condition associated with an abnormally high level of angiogenesis, a therapeutically effective amount of a composition comprising an siRNA inhibitor that specifically inhibits protein kinase C epsilon (PKCϵ), the siRNA comprising a sequence that differs from SEQ ID NO:20 by no more than 1, 2, 3, 4, or 5 nucleotides.

2. The method of claim 1, wherein the subject has oxygen-induced retinopathy-of-prematurity, oxygen-induced retinopathy, or proliferative diabetic retinopathy.

3. The method of claim 2, wherein the composition is administered to the eye of the subject.

* * * * *